United States Patent
Ruoslahti et al.

(10) Patent No.: US 6,232,287 B1
(45) Date of Patent: May 15, 2001

(54) MOLECULES THAT HOME TO VARIOUS SELECTED ORGANS OR TISSUES

(75) Inventors: Erkki Ruoslahti, Rancho Santa Fe; Renata Pasqualini, Solana Beach, both of CA (US); Wadih Arap, Houston, TX (US)

(73) Assignee: The Burnham Institute, La Jolla, CA (US)

( * ) Notice: Subject to any disclaimer, the term of this patent is extended or adjusted under 35 U.S.C. 154(b) by 0 days.

(21) Appl. No.: 09/042,107

(22) Filed: Mar. 13, 1998

(51) Int. Cl.[7] .......................... A61K 38/02; A61K 38/08; C07K 2/00; C07K 7/06; G01N 33/68
(52) U.S. Cl. ......................... 514/2; 424/9.1; 424/9.341; 436/63; 436/64; 436/501; 514/16; 530/300; 530/329; 530/345; 530/350
(58) Field of Search ............................ 424/9.341, 9.411, 424/9.1; 436/501.63, 64.86; 530/300, 329, 345, 350; 514/2, 16

(56) References Cited

U.S. PATENT DOCUMENTS

| | | | |
|---|---|---|---|
| 5,622,699 | 4/1997 | Ruoslahti | 424/93.6 |
| 5,824,490 | * 10/1998 | Coffey et al. | 435/7.23 |
| 6,068,829 | * 5/2000 | Ruoslahti et al. | 424/9.1 |

FOREIGN PATENT DOCUMENTS

| | | |
|---|---|---|
| WO 97/26918 | 7/1997 | (WO) . |
| 98/03873 | * 1/1998 | (WO) . |

OTHER PUBLICATIONS

Calvo et al. Identification, Primary Structure, and Distribution . . . J. Biol. Chem. vol. 268, No. 25, pp. 18929–18935, Sep. 5, 1993.*

Carter et al., "Prostate–specific membrane antigen is a hydrolase with substrate and pharmacologic characteristics of a neuropeptidase," *Proc. Natl. Acad. Sci. USA*, 93:749–753 (1996).

Daher and Beaini, "Prostate–specific antigen and new related markers for prostate cancer," *Clinical Chemistry Laboratory Medicine* 36: 671–81 (1998).

Dowling and Tannock, "Systemic treatment for prostate cancer," *Cancer Treatment Review* 24:283–301 (1998).

Folkman J., "Angiogenesis in cancer, vascular, rheumatoid and other disease," *Nature Medicine* 1:27–31 (1995).

Jacobson et al., "Identification of endothelial cell–surface proteins as targets for diagnosis and treatment of disease," *Nature Medicine* 2:482–484 (1996).

Jain R., "Vascular and interstitial barriers to delivery of therapeutic agents in tumors," *Cancer and Metastasis Reviews* 9:253–266 (1990).

Liu et al., "Monoclonal Antibodies to the Extracellular Domain of Prostate–specific Membrane Antigen Also React with Tumor Vascular Endothelium," *Cancer Research*, 57:3629–3634 (1997).

Sciavolino and Abate–Shen, "Molecular biology of prostate development and prostate cancer," *Ann Medicine* 30:357–68 (1998).

Vogel G., "Peptide–Guided Cancer Drugs Show Promise in Mice," *Science* 279:323–324 (1998).

* cited by examiner

*Primary Examiner*—Jeffrey E. Russel
(74) *Attorney, Agent, or Firm*—Campbell & Flores LLP

(57) ABSTRACT

The present invention provides molecules that selectively home to various normal organs or tissues, including to lung, pancreas, skin, retina, prostate, ovary, lymph node, adrenal gland, liver or gut; and provides molecules that selectively home to tumor bearing organs or tissues, including to pancreas bearing a pancreatic tumor or to lung bearing a lung tumor. The invention also provides conjugates, comprising an organ or tissue homing molecule linked to a moiety. Such a moiety can be, for example, a therapeutic agent or a detectable agent. In addition, the invention provides methods of using an organ homing molecule of the invention to identify a particular organ or tissue by contacting the organ or tissue with a molecule of the invention. The invention also provides methods to diagnose or treat a pathology of the lung, pancreas, skin, retina, prostate, ovary, lymph node, adrenal gland, liver or gut by administering to a subject having or suspected of having a pathology a molecule that homes to the selected organ or tissue. The invention further provides methods of identifying a target molecule in lung, pancreas, skin, retina, prostate, ovary, lymph node, adrenal gland, liver or gut.

105 Claims, 4 Drawing Sheets

US 6,232,287 B1

MOLECULES THAT HOME TO VARIOUS SELECTED ORGANS OR TISSUES

This invention was made with government support under grant numbers CA 74238 and CA 30199 awarded by the National Institutes of Health.

BACKGROUND OF THE INVENTION

1. Field of the Invention

The present invention relates generally to the fields of molecular medicine and drug delivery and, more specifically, to molecules that home to a specific organ or tissue.

2. Background Information

Although the effect of a particular pathology often is manifest throughout the body of the afflicted person, generally, the underlying pathology may affect only a single organ or tissue. It is rare, however, that a drug or other treatment will target only the diseased organ or tissue. More commonly, treatment results in undesirable side effects due, for example, to generalized toxic effects throughout the patient's body. It would be desirable to selectively target organs or tissues, for example, for treatment of diseases associated with the target organ or tissue. In particular, targeting of an organ or tissue can be useful for directing the expression of a gene to a certain organ or tissue because incorporation of a foreign gene into nontargeted cells can cause unwanted side effects such as malignant transformation.

Most therapeutic substances are delivered to the target organ or tissue through the circulation. The endothelium, which lines the internal surfaces of blood vessels, is the first cell type encountered by a circulating therapeutic substance in the target organ or tissue. These cells provide a target for selectively directing therapies to an organ or tissue.

Endothelium can have distinct morphologies and biochemical markers in different tissues. The blood vessels of the lymphatic system, for example, express various adhesion proteins that serve to guide lymphocyte homing. For example, endothelial cells present in lymph nodes express a cell surface marker that is a ligand for L-selectin and endothelial cells in Peyer's patch venules express a ligand for the $\alpha_4\beta_7$ integrin. These ligands are involved in specific lymphocyte homing to their respective lymphoid organs. Thus, linking a drug to L-selectin or to the $\alpha_4\beta_7$ integrin may provide a means for targeting the drug to diseased lymph nodes or Peyer's patches, respectively, provided that these molecules do not bind to similar ligands present in a significant number of other organs or tissues.

Although the homing molecules present in the blood vessels of non-lymphoid tissues have not been clearly defined, certain observations of lymphocyte circulation suggest that organ and tissue specific endothelial markers exist. Similarly, the homing or metastasis of particular types of tumor cells to specific organs or tissues further suggests that organ and tissue specific markers may exist. Thus, a need exists to identify molecules that can bind to such organ or tissue specific markers and, therefore, can home to the organ or tissue. The present invention satisfies this need and provides related advantages as well.

SUMMARY OF THE INVENTION

The present invention provides molecules that selectively home to various normal organs or tissues, including to lung, skin, pancreas, retina, prostate, ovary, lymph node, adrenal gland, liver or gut. For example, the invention provides lung homing peptides such as those containing a GFE motif, including the peptides CGFECVRQCPERC (SEQ ID NO: 1) and CGFELETC (SEQ ID NO: 2); skin homing peptides such as CVALCREACGEGC (SEQ ID NO: 3); pancreas homing peptides such as the peptide SWCEPGWCR (SEQ ID NO: 4); and retina homing peptides such as those containing an RDV motif, including the peptides CSCFRDVCC (SEQ ID NO: 5) and CRDVVSVIC (SEQ ID NO: 6).

The invention also provides conjugates, comprising an organ or tissue homing molecule linked to a moiety. Such a moiety can be a therapeutic agent such as a toxin, an agent that inhibits cell death, an agent that alters the production or activity of a deleterious or beneficial substance by a cell, or an agent that alters proliferation of a cell exposed to the agent. A moiety also can be a detectable agent such as a radionuclide, or a tag such as a chambered microdevice or an insoluble chromatography support. Such conjugates of the invention are useful for directing the moiety to a selected organ or tissue.

The invention also provides methods of using an organ homing molecule of the invention to diagnose or treat a pathology of the lung, skin, pancreas, retina, prostate, ovary, lymph node, adrenal gland, liver or gut by administering a molecule that homes to the selected organ or tissue to a subject having or suspected of having a pathology. For example, a pathology of lung, skin, pancreas, retina, prostate, ovary, lymph node, adrenal gland, liver or gut can be treated by administering to a subject having the pathology a conjugate comprising an appropriate organ homing molecule linked to a therapeutic agent. Similarly, a method of identifying a selected organ or tissue or diagnosing a pathology in a selected organ by administering to a subject a conjugate comprising an appropriate organ homing molecule linked to a detectable agent.

The invention further provides methods of identifying a target molecule in lung, pancreas, skin, retina, prostate, ovary, lymph node, adrenal gland, liver or gut by-detecting selective binding of the target molecule to a lung, skin, pancreas, retina, prostate, ovary, lymph node, adrenal gland, liver or gut homing molecule, respectively. For example, a peptide that selectively homes to lung can be attached to a solid matrix, a sample of lung can be obtained and passed over the affinity matrix under conditions that allow specific binding of the target molecule, and the target molecule can be collected and identified. Thus, the invention also provides a target molecule, which binds an organ homing molecule, particularly a lung, skin, pancreas, retina, prostate, ovary, lymph node, adrenal gland, liver or gut homing molecule. Such a target molecule can be useful, for example, for raising an antibody specific for the target molecule.

BRIEF DESCRIPTION OF THE DRAWINGS

FIG. 2B, CGFELETC, SEQ ID NO: 2, "GFE-2"); skin (FIG. 2C, CVALCREACGEGC, SEQ ID NO: 3) or pancreas (FIG. 2D, SWCEPGWCR, SEQ ID NO: 4) were individually amplified, injected into mice and recovered (Example I. The amount of phage displaying a selected peptide that was recovered per gram of lung, skin or pancreas or control kidney or brain was determined. The amount of unselected (control) phage recovered from lung, skin, pancreas, kidney or brain also was determined. Bars indicate standard error of the mean from triplicate platings.

In FIG. 3A, 100 µg or 500 µg of GST-CGFECVRQCPERC (SEQ ID NO: 1, "GFE-1") or 500 µg GST was coinjected into mice with $10^9$ transducing units of the individually amplified phage displaying the lung homing sequence CGFECVRQCPERC (SEQ ID NO: 1). The recovery of phage after 5 minutes of circulation from lung and kidney was determined, with bars indicating standard error of the mean from triplicate platings.

In FIG. 3B, $10^9$ transducing units of individually amplified phage displaying either the lung homing peptides CGFECVRQCPERC (SEQ ID NO: 1, "GFE-1") or CGFELETC (SEQ ID NO: 2, "GFE-2") or the skin homing peptide CVALCREACGEGC (SEQ ID NO: 3) were coinjected into mice with 500 µg of the cognate GST-fusion peptide. Control mice (not shown) were injected with the selected phage and 500 µg of GST. The percentage of inhibition of selected phage homing to lung or skin in the presence of the cognate GST-fusion peptide compared to GST is shown.

DETAILED DESCRIPTION OF THE INVENTION

Figure 1:
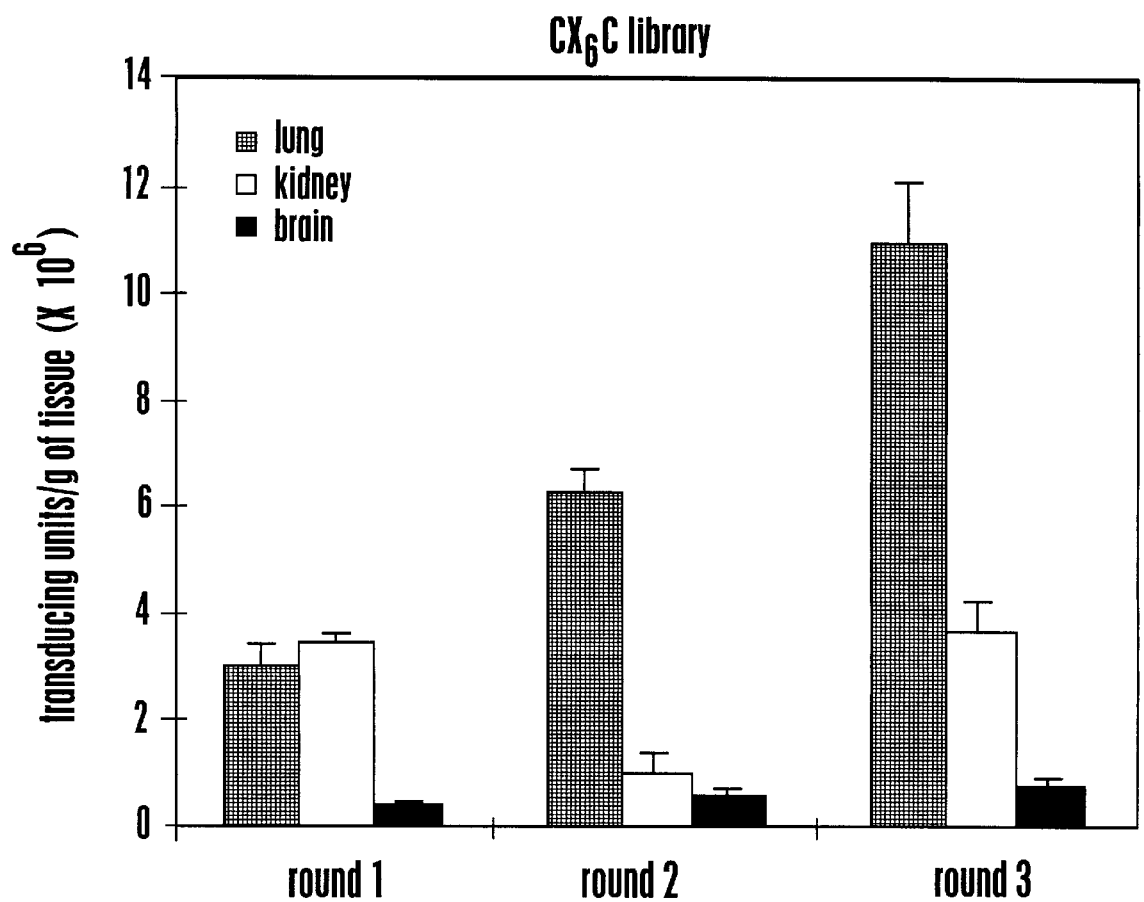
FIG. 1 shows the results of three rounds of in vivo panning of a $CX_6C$ (SEQ ID NO: 26) library for identifying molecules that home to lung. Phage recovered from the lung five minutes after injection of $10^{10}$ transducing units into the tail vein of mice were amplified and reinjected in two consecutive rounds. The number of phage recovered per gram of lung, kidney or brain is indicated for each round, with bars representing standard error of the mean from triplicate platings.
Figure 2A:
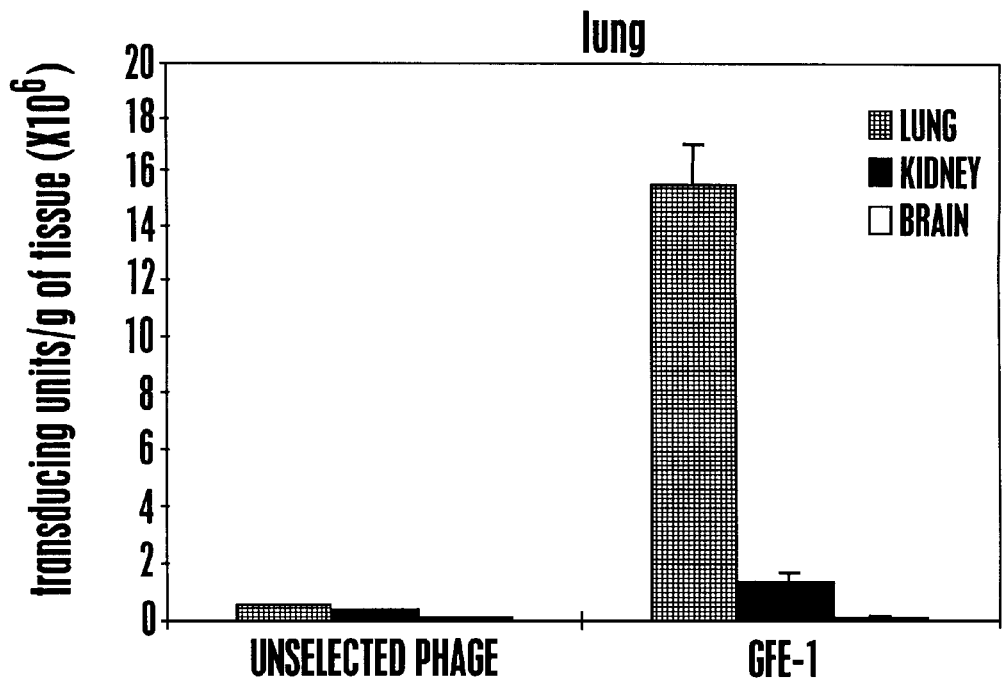
FIGS. 2A to 2D show the selectivity of phage displaying a lung (FIGS. 2A and 2B), skin (FIG. 2C) or pancreas (FIG. 2D) homing peptides. Selected phage expressing peptides that home to lung (FIG. 2A, CGFECVRQCPERC, SEQ ID NO: 1, "GFE-1"
Figure 2B:
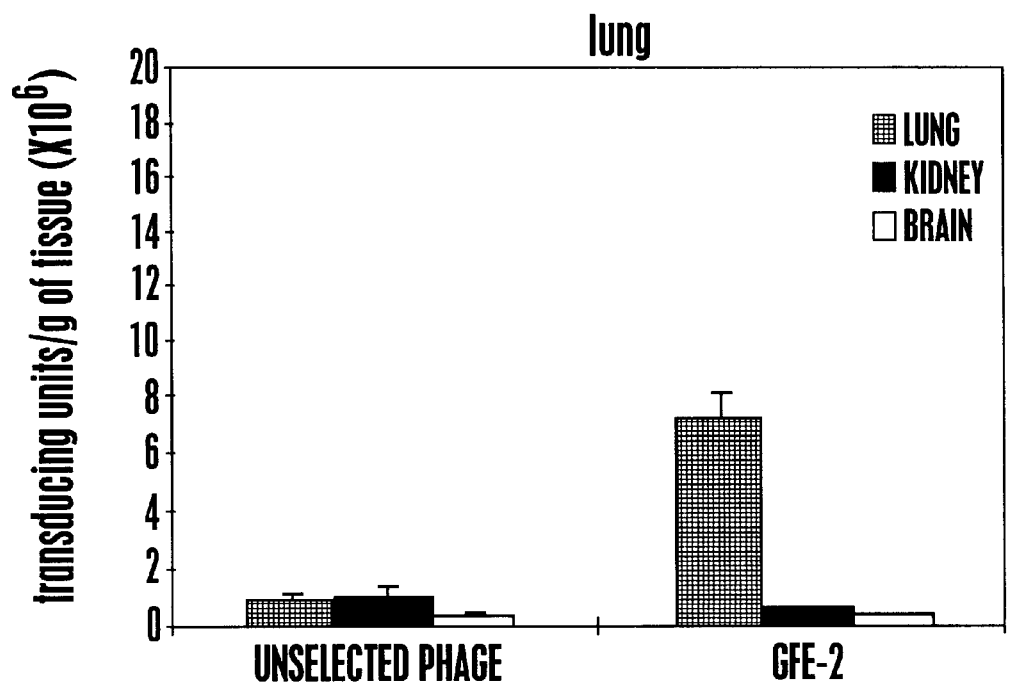
Figure 2C:
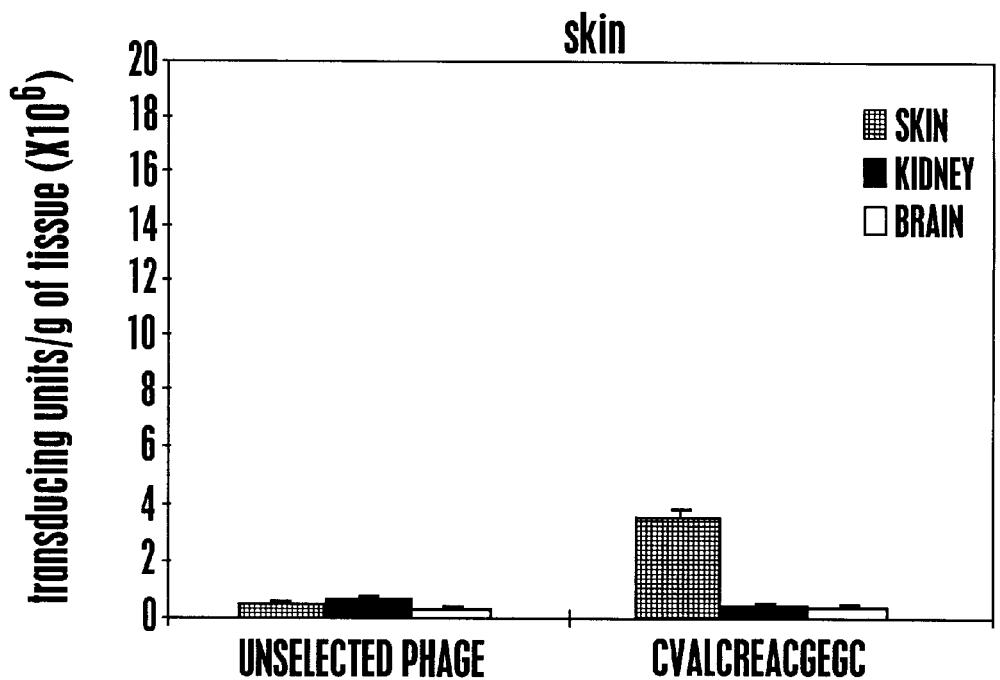
Figure 2D:
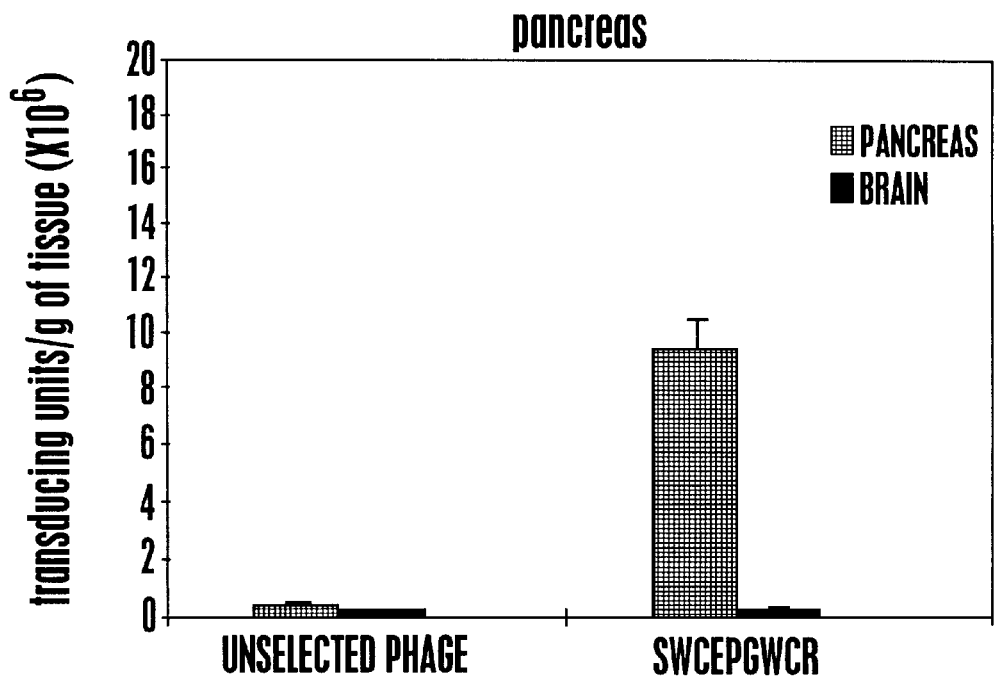

The present invention provides organ and tissue homing molecules and methods of using these molecules to target a moiety to a selected organ or tissue. The molecules of the invention, which were identified essentially by the method of in vivo panning (U.S. Pat. No. 5,622,699, issued Apr. 22, 1997, which is incorporated herein by reference), include peptides that home to various normal organs or tissues, including lung, skin, pancreas, retina, prostate, ovary, lymph node, adrenal gland, liver or gut, and to organs bearing tumors, including to lung bearing lung tumors and to pancreas bearing a pancreatic tumor. For example, the invention provides lung homing peptides, including the peptides CGFECVRQCPERC (SEQ ID NO: 1) and CGFELETC (SEQ ID NO: 2), each of which contains a tripeptide GFE motif, and the peptide GIGEVEVC (SEQ ID NO: 8). The invention also provides skin homing peptides such as the peptide CVALCREACGEGC (SEQ ID NO: 3); pancreas homing peptides such as the peptide SWCEPGWCR (SEQ ID NO: 4) and retina homing peptides such as the peptides CSCFRDVCC (SEQ ID NO: 5) and CRDVVSVIC (SEQ ID NO: 6), each of which contains a tripeptide RDV motif. Examples of peptides that home to prostate, ovary, lymph node, adrenal gland, liver and gut are also provided (see Tables 2 to 11). It should be recognized that motifs common to particular organ homing peptides can be identified by simple inspection of the peptides. For example, inspection of Table 9 reveals that the peptides AGCSVTVCG (SEQ ID NO: 315) and AGCVQSQCY (SEQ ID NO: 370) share an AGC motif; the peptides LECRRWRCD (SEQ ID NO: 328) and LECVANLCT (SEQ ID NO: 337) share an LEC motif; and the peptides SECAYRACS (SEQ ID NO: 319) and SECYTGSCP (SEQ ID NO: 375) share an SEC motif. In addition, several of these peptides were isolated more than one time (see asterisks in Table 9), indicating that such motifs are relevant to the ability of the peptides to selectively home. Peptides comprising the particular motifs disclosed herein, as well as other motifs identifiable by inspection of the disclosed peptides, are considered within the claimed invention, provided that the motif is not an RGD motif.

The homing molecules of the invention are useful for targeting a moiety to a particular organ or tissue. Thus, the invention provides conjugates, comprising an organ homing molecule linked to a moiety. Such moieties can be a therapeutic agent such as a virus; a viral gene therapy vector; a drug; a detectable or imaging agent such as a radionuclide; or a tag such as biotin. As disclosed herein, such organ homing molecules of the invention, particularly conjugates of the invention, can be used to detect or visualize a selected organ or tissue or to diagnose or treat a pathology in a selected organ or tissue. An organ homing molecule of the invention also can be used to isolate the target molecule that is expressed in the selected organ or tissue and binds the organ homing molecule. For convenience, a molecule of the invention that homes to a selected organ or tissue is referred to as an "organ homing molecule."

As used herein, the term "molecule" is used broadly to mean an organic compound having at least one reactive group that can be varied by substituting one or more different groups. An organic molecule can be a drug; a nucleic acid molecule, including RNA or DNA; a peptide; a variant or modified peptide or a peptide mimetic; a protein or a fragment thereof; an oligosaccharide; a lipid; a glycolipid; or a lipoprotein.

An organic molecule can be a naturally occurring molecule, which can be a product of nature in that the groups comprising the organic molecule and the bonds linking the groups are produced by biological processes. For example, a naturally occurring organic molecule can be an RNA molecule or a fragment thereof, which can be isolated from a cell or expressed from a recombinant nucleic acid molecule. Similarly, a peptide is considered a naturally occurring organic molecule, even if it is produced by chemical synthesis, since the amino acid groups and bonds linking the groups can be produced by normal biological processes and the peptide, itself, can be produced in a cell due, for example, to proteolytic degradation of a protein containing the peptide.

An organic molecule also can be a nonnaturally occurring molecule. Such molecules have chemical groups or bonds that are not normally produced by biological processes. For example, a nucleic acid sequence containing nonnaturally occurring nucleoside analogs or phosphorothioate bonds that link the nucleotides and protect against degradation by nucleases are examples of nonnaturally occurring molecules. A ribonucleotide containing a 2-methyl group, instead of the normal hydroxyl group, bonded to the 2'-carbon atom of ribose residues, is an example of a non-naturally occurring RNA molecule that is resistant to enzymatic and chemical degradation. Other examples of nonnaturally occurring organic molecules include RNA containing 2'-aminopyrimidines, such RNA being 1000× more stable in human serum and urine as compared to naturally occurring RNA (see Lin et al., *Nucl. Acids Res.*, 22:5229–5234 (1994); and Jellinek et al., *Biochemistry*, 34:11363–11372 (1995), each of which is incorporated herein by reference).

For convenience, the term "peptide" is used broadly herein to mean peptides, polypeptides, proteins and fragments of proteins and includes, for example, single-chain peptides. Other molecules useful in the invention include peptoids, peptidomimetics and the like. With respect to the organ or tissue homing peptides of the invention, peptidomimetics, which include chemically modified peptides, peptide-like molecules containing nonnaturally occurring amino acids, peptoids and the like, have the binding activity of an organ homing peptide upon which the peptidomimetic is derived (see, for example, "Burger's Medicinal Chemistry and Drug Discovery" 5th ed., vols. 1 to 3 (ed. M. E. Wolff; Wiley Interscience 1995), which is incorporated herein by reference). Peptidomimetics provide various advantages over a peptide, including that a peptidomimetic can be stable when administered to a subject, for example, during passage through the digestive tract and, therefore, useful for oral administration.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). This structural depository is continually updated as new crystal structures are determined and can be screened for compounds having suitable shapes, for example, the same shape as an organ or tissue homing molecule, as well as potential geometrical and chemical complementarity to a target molecule bound by an organ or tissue homing peptide. Where no crystal structure of a homing peptide or a target molecule, which binds an organ or tissue homing molecule, is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of an organ or tissue homing molecule.

The term "nucleic acid molecule" also is used broadly to mean any polymer of two or more nucleotides, which are linked by a covalent bond such as a phosphodiester bond, a thioester bond, or any of various other bonds known in the art as useful and effective for linking nucleotides. Such nucleic acid molecules can be linear, circular or supercoiled, and can be single stranded or double stranded DNA or RNA or can be a DNA/RNA hybrid.

As used herein, the term "library" means a collection of molecules. A library can contain a few or a large number of different molecules, varying from about two to about $10^{15}$ molecules or more. The chemical structure of the molecules of a library can be related to each other or be diverse. If desired, the molecules constituting the library can be linked to a common or unique tag, which can facilitate recovery and/or identification of the molecule.

Methods for preparing libraries containing diverse populations of various types of molecules such as peptides, peptoids and peptidomimetics are well known in the art and various libraries are commercially available (see, for example, Ecker and Crooke, Biotechnology 13:351–360 (1995), and Blondelle et al., Trends Anal. Chem. 14:83–92 (1995), and the references cited therein, each of which is incorporated herein by reference; see, also, Goodman and Ro, Peptidomimetics for Drug Design, in "Burger's Medicinal Chemistry and Drug Discovery" Vol. 1 (ed. M. E. Wolff; John Wiley & Sons 1995), pages 803–861, and Gordon et al., J. Med. Chem. 37:1385–1401 (1994), each of which is incorporated herein by reference). Where a molecule is a peptide, protein or fragment thereof, the molecule can be produced in vitro directly or can be expressed from a nucleic acid, which can be produced in vitro. Methods of synthetic peptide and nucleic acid chemistry are well known in the art.

A library of peptide molecules also can be produced, for example, by constructing a cDNA expression library from mRNA collected from a cell, tissue, organ or organism of interest. Methods for producing such libraries are well known in the art (see, for example, Sambrook et al., Molecular Cloning: A laboratory manual (Cold Spring Harbor Laboratory Press 1989), which is incorporated herein by reference). Preferably, a peptide encoded by the cDNA is expressed on the surface of a cell or a virus containing the cDNA. For example, cDNA can be cloned into a phage vector such as fuse 5 (Example I), wherein, upon expression, the encoded peptide is expressed as a fusion protein on the surface of the phage.

In addition, a library of molecules can be a library of nucleic acid molecules, which can be DNA, RNA or analogs thereof. For example, a cDNA library can be constructed from mRNA collected from a cell, tissue, organ or organism of interest, or by collecting genomic DNA, which can be treated to produce appropriately sized fragments using restriction endonucleases or methods that randomly fragment genomic DNA. A library comprising RNA molecules also can be constructed by collecting RNA from cells or by synthesizing the RNA molecules chemically. Diverse libraries of nucleic acid molecules can be made using solid phase synthesis, which facilitates the production of randomized regions in the molecules. If desired, the randomization can be biased to produce a library of nucleic acid molecules containing particular percentages of one or more nucleotides at a position in the molecule (U.S. Pat. No. : 5,270,163, issued Dec. 14, 1993, which is incorporated herein by reference).

If desired, the nucleic acid molecules can be nucleic acid analogs that are less susceptible to degradation by nucleases. For example, RNA molecules containing 2'-0-methylpurine substitutions on the ribose residues and short phosphorothioate caps at the 3'- and 5'-ends exhibit enhanced resistance to nucleases (Green et al., Chem. Biol., 2:683–695 (1995), which is incorporated herein by reference). Similarly, RNA containing 2'-amino-2'-deoxypyrimidines or 2'-fluro-2'-deoxypyrimidines is less susceptible to nuclease activity (Pagratis et al., Nature Biotechnol., 15:68–73 (1997), which is incorporated herein by reference). Furthermore, L-RNA, which is a stereoisomer of naturally occurring D-RNA, is resistant to nuclease activity (Nolte et al., Nature Biotechnol., 14:1116–1119 (1996); Klobmann et al., Nature Biotechnol., 14:1112–1115 (1996); each of which is incorporated herein by reference). Such RNA molecules and methods of producing them are well known and routine (see Eaton and Piekern, Ann. Rev. Biochem., 64:837–863 (1995), which is incorporated herein by reference). DNA molecules containing phosphorothioate linked oligodeoxynucleotides are nuclease resistant (Reed et al., Cancer Res. 50:6565–6570 (1990), which is incorporated herein by reference). Phosphorothioate-3' hydroxypropylamine modification of the phosphodiester bond also reduces the susceptibility of a DNA molecule to nuclease degradation (see Tam et al., Nucl. Acids Res., 22:977–986 (1994), which is incorporated herein by reference). If desired, the diversity of a DNA library can be enhanced by replacing thymidine with 5-(1-pentynyl)-2'-deoxoridine (Latham et al., Nucl. Acids Res. 22:2817–2822 (1994), which is incorporated herein by reference). Such modified nucleic acid molecules can be useful for the manufacture of a library or for the purpose of being a tag, which is described later below.

As disclosed herein, in vivo panning for the purpose of identifying an organ or tissue homing molecule comprises administering a library to a subject, collecting an organ or tissue sample and identifying an organ or tissue homing molecule using various methods well known in the art. Generally, the presence of an organ or tissue homing molecule in a collected organ or tissue is identified based on one or more characteristics common to the molecules present in the library, then the structure of a particular organ or tissue homing molecule can be determined.

A highly sensitive detection method such as mass spectrometry (MS), either alone or in combination with a method such as gas chromatography (GC), can be used to identify homing molecules that are closely related even when present in small amounts in a selected organ or tissue. For example, GC in combination with MS was used to identify two major and four minor lidocaine metabolites following lidocaine injection into rats and the analysis of urine (Coutts et al., *J. Chromatogr.* 421:267–280 (1987), which is incorporated herein by reference). Similarly, where a library comprises diverse molecules based generally on the structure of an organic molecule such as a drug, an organ or tissue homing molecule can be identified by determining the presence of a parent peak for the particular molecule.

If desired, the selected organ or tissue can be processed using a method such as HPLC, which can be used to obtain an enriched fraction of molecules having a defined range of molecular weights or polarity or the like from a complex mixture. The enriched fraction of molecules then can be further analyzed for the purposes of identifying organ or tissue homing molecules. For example, HPLC coupled with GC and MS were used to identify seven metabolites of a vitamin D analogue after injection of dihydrotachysterol 3 into a rat and fractionation of an isolated perfused kidney (Porteous et al., *Biomed. Environ. Mass Spectrum* 16:87–92 (1988), which is incorporated herein by reference). Conditions for HPLC will depend on the structure of the particular molecule and can be optimized by those skilled in the art based on knowledge of the molecule.

The organ homing molecules present in a collected sample of organ or tissue can be recovered from the sample by incubation in a solution having a defined salt concentration and temperature. Selective extraction also can be used to obtain different fractions of organic molecules by sequentially incubating a collected sample in one or more solutions. Such solutions can have a different salt concentration or can effect extraction of an organic homing molecule at a particular temperature. The resulting eluates from the collected sample can be collected separately or can be pooled into one or more fractions and the organ homing molecules can be detected and identified. Similarly, methods for bulk removal of potentially interfering cellular materials such as DNA, RNA, proteins, lipids or carbohydrates are well known in the art. Such methods can be used to enrich for the particular organ homing molecule from potentially contaminating materials in the collected sample and to increase the sensitivity of detecting the molecule.

Ease of identification of an organ or tissue homing molecule, particularly an untagged molecule, depends upon various factors, including the presence of potentially contaminating background cellular material. For example, where the homing molecule is an untagged peptide, a larger number must home to the organ or tissue in order to identify the specific peptides over the background of cellular protein. In contrast, a much smaller amount of an untagged homing molecule such as a drug is identifiable because such molecules normally are generally absent from or present in very small numbers in the body. In this situation, a highly sensitive method such as MS can be used to identify an organ homing molecule. The skilled artisan will recognize that the method of identifying a molecule will depend, in part, on the structure of the particular molecule.

As disclosed herein, a sufficient number of molecules selectively home to a selected organ or tissue during in vivo panning such that the molecules readily can be identified. For example, peptides that were identified two or more times in a particular collected organ (see Table 1). For example, of forty clones sequenced from various selected organs, the gut homing peptide YSGKWGK (SEQ ID NO: 9) was present in 22% of the clones; the ovary homing peptides EVRSRLS (SEQ ID NO: 10) and RVGLVAR (SEQ ID NO: 11) each was present in 22% of the clones; and the liver homing peptide VKSVCRT (SEQ ID NO: 12) was present in 11% of the clones (see Table 1). Similarly, the lung homing peptides CLAKENVVC (SEQ ID NO: 13) and CGFECVRQCPERC (SEQ ID NO: 1); the skin homing peptide CVALCREACGEGC (SEQ ID NO: 3); and the retina homing peptide CGEFKVGC (SEQ ID NO: 14) each was independently isolated several times during in vivo panning of the respective organs, as were other organ homing peptides (see Tables 2 to 11; peptides marked with asterisk). These results demonstrate that a substantial fraction of the identified organ homing molecules have the same structure or, in many cases, share conserved motifs.

Following various in vivo panning screens, hundreds of thousands to millions of phage expressing homing peptides were recovered from the respective organ or tissue. Generally, the phage collected from a round of in vivo panning were plated on agar, about 250 to 300 clones were selected, grown in 5 ml cultures, then pooled and readministered for a subsequent round of in vivo panning ("regular method"). However, in some experiments, 1000 clones were selected, grown in 2 ml cultures, then pooled and administered for a subsequent round of screening; or the entire agar plate was scraped and all of the phage were cultured together and administered for a subsequent round of screening. The peptide inserts of various isolated phage were determined such that, of the millions of phage that homed, only a small number of sequences were identified. These results indicate that specific types of homing molecules can be present in relatively large proportions in an organ or tissue following in vivo homing, thereby increasing the ease with which the molecules can be identified.

Where an organ or tissue homing molecule is a nucleic acid molecule, various assay methods can be used to substantially isolate or identify the molecule. For example, PCR can be particularly useful for identifying the presence of the homing molecule because, in principle, PCR can detect the presence of a single nucleic acid molecule (see, for example, Erlich, *PCR Technology: Principles and Applications for DNA Amplification* (Stockton Press (1989), which is incorporated herein by reference). PCR also has been used to amplify nucleic acid molecules that bind to a predetermined target in vitro and, when the nucleic acids were rendered resistant to nucleases and administered to a subject, they modulated biological processes such as lymphocyte trafficking in vivo (see, for example, Hicke et al., *J. Clin. Invest.* 98:2688–2692 (1996), which is incorporated herein by reference). These findings indicate that nucleic acid molecules are sufficiently stable when administered into the circulation of a subject such that in vivo panning can be used to identify nucleic acid molecules that selectively home to an organ or tissue in vivo.

The molecules of a library can be tagged, which can facilitate recovery or identification of the organ homing molecules. As used herein, the term "tag" means a physical, chemical or biological moiety such as a plastic or metallic microbead, an oligonucleotide or a bacteriophage, respectively, that is linked to a molecule of the library. Methods for tagging a molecule are well known in the art (Hermanson, *Bioconjugate Techniques*, (Academic Press 1996), which is incorporated herein by reference). The link between a molecule and a tag can be a covalent or a non-covalent bond and, if desired, the link can be selectively cleavable from the molecule.

As used herein, the term "shared tag" means a physical, chemical or biological moiety that is common to each molecule in a library. A shared tag can be used to identify the presence of a molecule of the library in a sample or to substantially isolate the molecules from a sample following in vivo panning. For example, a library that comprises a population of diverse molecules such as nucleic acids can be linked to a shared tag. If the shared tag is biotin, for example, a nucleic acid homing molecule can be substantially isolated from a selected organ or tissue by binding, for example, to a streptavidin affinity column. The presence of the organ or tissue homing nucleic acid molecule also can be detected by binding with a labeled streptavidin. A peptide such as the hemagglutinin antigen also can be a shared tag, which, when linked to each molecule in a library, allows the use of an antibody specific for the hemagglutinin antigen to substantially isolate homing molecules from a selected organ or tissue. Furthermore, a molecule or a support containing a molecule can be linked to a hapten such as 4-ethoxy-methylene-2-phenyl-2-oxazoline-5-one (phOx), which can be bound by an anti-phOx antibody linked to a magnetic bead as a means to recover the homing molecule. Methods for purifying phOx labeled conjugates are known in the art and the materials for performing these procedures are commercially available (Invitrogen, La Jolla Calif.; Promega Corp., Madison Wis.).

A shared tag also can be a nucleic acid sequence that can be used to identify the presence of molecules of the library in a sample or to substantially isolate molecules of a library from a sample. For example, each of the molecules of a library can be linked to the same selected nucleotide sequence, which constitutes the shared tag. An affinity column containing a nucleotide sequence that is complementary to the shared tag then can be used to isolate the homing molecules from an organ or tissue sample by hybridizing to the shared tag linked to the molecules. A nucleotide sequence complementary to a portion of the shared tag also can be used as a PCR primer such that the presence of molecules containing the shared tag can be identified in a sample by PCR.

A tag also can be a specific or a unique tag. As used herein, the term "specific tag" means a physical, chemical or biological tag that is linked to a molecule in a library and that is unique for the particular molecule. A specific tag is particularly useful if it is readily identifiable. A nucleotide sequence that is unique for a particular molecule of a library is an example of a specific tag, for example, a unique oligonucleotide tag linked to each peptide of a library or peptides (see, for example, Brenner and Lerner, *Proc. Natl. Acad. Sci., USA* 89:5381–5383 (1992), which is incorporated herein by reference). Upon homing to an organ or tissue, the homing peptide can be identified by determining the sequence of the unique oligonucleotide tag using, for example, PCR (see, for example, Erlich, *PCR Technology: Principles and Applications for DNA Amplification* (Stockton Press 1989), which is incorporated herein by reference). Similarly, the nucleic acid sequence encoding a peptide displayed on a phage is another example of a specific nucleic acid tag, since sequencing of the nucleic acid identifies the amino acid sequence of the expressed peptide (see Example I). Such unique oligonucleotide sequence tags, when linked to other libraries of molecules, can be used to identify the sequence of the homing molecule linked thereto.

A shared tag and specific tag, in combination, can be particularly useful for isolating and identifying an organ or tissue homing molecule when the homing molecule is present in minute quantities. For example, each molecule of a library can be linked to an oligonucleotide tag which contains two portions; an internal unique nucleotide sequence tag and shared flanking 5' and 3' nucleotide tags that serve as primer binding sites for use in PCR. Each molecule, therefore, contains an oligonucleotide tag having a unique portion to identify the homing molecule and a shared portion to provide PCR primer binding sites. Such a tagged molecule, upon homing to a selected organ or tissue, can be identified by performing PCR using primers that hybridize to the shared flanking 5' and 3' nucleotide tags, then performing DNA sequencing to determine the nucleotide sequence of the internal unique sequence tag. The PCR product can be sequenced directly using one of the PCR primers or the PCR product can be cloned into a vector and the DNA sequence determined by routine methods well known in the art.

Various other combinations of shared and unique tags can be used. For example, each of the molecules in a library can be linked to a specific nucleotide sequence tag (see, for example, Brenner and Lerner, supra, 1992), which also contains a shared 3' nucleotide sequence that can be a primer binding site for use in PCR, and can be further linked to a shared tag such as biotin. Upon homing to an organ or tissue, the particular homing molecule can be substantially isolated from an organ or tissue sample based on the biotin tag. The isolated molecules can then be identified, for example, by PCR based DNA sequencing of the specific tag using the shared 3' nucleotide sequence of the nucleotide tag as a primer binding site.

A tag also can serve as a support. As used herein, the term "support" means a tag having a defined surface to which a molecule can be attached. In general, a tag useful as a support is a shared tag. For example, a support can be a biological tag such as a virus or virus-like particle such as a bacteriophage ("phage"); a bacterium such as *E. coli*; or a eukaryotic cell such as a yeast, insect or mammalian cell; or can be a physical tag such as a liposome or a microbead, which can be composed of a plastic, agarose, gelatin or other biological or artificial material. If desired, a shared tag useful as a support can have linked thereto a specific tag.

As exemplified herein, a peptide suspected of being able to home to a selected normal organ or tissue such as lung, skin, pancreas, retina, prostate, ovary, lymph node, adrenal gland, liver or gut, or to an organ or tissue containing a tumor, for example, a lung containing lung tumors or a pancreas containing a pancreatic tumor, was expressed as the N-terminus of a fusion protein, wherein the C-terminus consisted of a phage coat protein (see Example I). Upon expression of the fusion protein, the C-terminal coat protein linked the fusion protein to the surface of a phage such that the N-terminal peptide was in a position to interact with a target molecule in the organ or tissue. Thus, a molecule having a shared tag was formed by the linking of a peptide to a phage, wherein the phage provided a biological support, the peptide molecule was linked as a fusion protein, the phage-encoded portion of the fusion protein acted as a spacer molecule, and the nucleic acid encoding the peptide provided a specific tag allowing identification of organ and tissue homing peptides.

Where a molecule is linked to a support, the tagged molecule comprises the molecule attached to the surface of the support, such that the part of the molecule suspected of being able to interact with a target molecule in a cell in the subject is positioned so as to be able to participate in the interaction. For example, where the homing molecule is suspected of being a ligand for a growth factor receptor, the binding portion of the molecule attached to a support is positioned so it can interact with the growth factor receptor on a cell in an organ or tissue. If desired, an appropriate spacer can be positioned between the molecule and the support such that the ability of the potential organ or tissue homing molecule to interact with the target molecule is not hindered. A spacer molecule also can contain a reactive group, which provides a convenient and efficient means of linking a molecule to a support and, if desired, can contain a tag, which can facilitate recovery or identification of the molecule (see Hermanson, supra, 1996).

In general, a support should have a diameter less than about 10 $\mu$m to about 50 $\mu$m in its shortest dimension, such that the support can pass relatively unhindered through the capillary beds present in the subject so as to not occlude circulation. In addition, a support can be biologically inert, so that it does not perturb the normal expression of cell surface molecules or normal physiology of the subject. In addition, a support can be excretable or biodegradable, particularly where the subject used for in vivo panning is not sacrificed to collect a sample of a selected organ or tissue.

As used herein, the term "in vivo panning," when used in reference to the identification of an organ or tissue homing molecule, means a method of screening a library by administering the library to a subject and identifying a molecule that selectively homes to an organ or tissue in the subject (U.S. Pat. No. 5,622,699, supra, 1997). The term "administering to a subject", when used in referring to a library of molecules or a portion of such a library, is used in its broadest sense to mean that the library is delivered to a selected organ or tissue in the subject, which, generally, is a vertebrate, particularly a mammal such as a human. Libraries of molecules can be administered by any route or means of administration, such as intravenously, intramuscularly, orally, optically, ocularly, intraperitoneally, nasally, vaginally, rectally, into the uterus, into a chamber of the eye, into the central or peripheral nervous system, by inhalation, by topical administration, or by injection into any normal organ or tissue or into a pathological region such as a tumor or an organ or tissue involved in a pathology, particularly into the circulatory system of the organ or tissue.

A library can be administered to a subject, for example, by injecting the library into the circulation of the subject such that the molecules pass through the selected organ or tissue; after an appropriate period of time, circulation is terminated, for example, by perfusion through the heart or by removing a sample of the organ or tissue (Example I; U.S. Pat. No. 5,622,699, supra, 1997; see, also, Pasqualini and Ruoslahti, Nature 380:364–366 (1996), which is incorporated herein by reference). Alternatively, a cannula can be inserted into a blood vessel in the subject, such that the library is administered by perfusion for an appropriate period of time, after which the library can be removed from the circulation through the cannula or the subject can be sacrificed or anesthetized to collect an organ or tissue sample. A library also can be shunted through one or a few organs or tissues including a selected organ or tissue, by cannulation of the appropriate blood vessels in the subject. It is recognized that a library also can be administered to an isolated perfused organ or tissue. Such panning in an isolated perfused organ or tissue can be useful to identify molecules that bind to the organ or tissue.

The use of in vivo panning to identify organ or tissue homing molecules is exemplified herein by screening a phage peptide display library in mice and identifying peptides that selectively homed to lung, pancreas, skin and others, and in rats, for peptides that homed to retina (Examples I and II). However, phage libraries that display other protein molecules, including, for example, an antibody or an antigen binding fragment of an antibody such an Fv, Fd or Fab fragment; a hormone receptor such as a growth factor receptor; or a cell adhesion receptor such as an integrin or a selectin also can be used to practice the invention. Variants of such molecules can be constructed using well known methods such as random, site directed or codon based mutagenesis (see Huse, U.S. Pat. No. 5,264,563, issued Nov. 23, 1993, which is incorporated herein by reference) and, if desired, peptides can be chemically modified, for example, by introducing a disulfide bridge, following expression of the phage but prior to administration to the subject. Thus, many different types of phage display libraries can be screened by in vivo panning.

Phage display technology provides a means for expressing a diverse population of random or selectively randomized peptides. Various methods of phage display and methods for producing diverse populations of peptides are well known in the art. For example, Ladner et al. (U.S. Pat. No. 5,223,409, issued Jun. 29, 1993, which is incorporated herein by reference) describe methods for preparing diverse populations of binding domains on the surface of a phage. In particular, Ladner et al. describe phage vectors useful for producing a phage display library, as well as methods for selecting potential binding domains and producing randomly or selectively mutated binding domains.

Similarly, Smith and Scott (Meth. Enzymol. 217:228–257 (1993); see, also, Scott and Smith, Science 249: 386–390 (1990), each of which is incorporated herein by reference) describe methods of producing phage peptide display libraries, including vectors and methods of diversifying the population of peptides that are expressed (see, also, Huse, WO 91/07141 and WO 91/07149, each of which is incorporated herein by reference; see, also, Example I). Phage display technology can be particularly powerful when used, for example, with a codon based mutagenesis method, which can be used to produce random peptides or randomly or desirably biased peptides (Huse, U.S. Pat. No. 5,264,563, supra, 1993). These or other well known methods can be used to produce a phage display library, which can be subjected to the in vivo panning method of the invention in order to identify a peptide that homes to a selected organ or tissue.

In addition to screening a phage display library, in vivo panning can be used to screen various other types of libraries. For example, nucleic acid molecules that bind to a cell surface receptor have been described (see O'Connell et al., Proc. Natl. Acad. Sci., USA 93:5883–5887 (1996); Tuerk and Gold, Science 249:505–510 (1990); Gold et al., supra (1995), each of which is incorporated herein by reference). These in vitro results indicate that a library of nucleic acid molecules also can be examined by in vivo panning to identify nucleic acid molecules that home to a selected organ or tissue. Additional libraries suitable for screening include, for example, oligosaccharide libraries (York et al., *Carb. Res.* 285:99–128, (1996); Liang et al., *Science* 274:1520–1522, (1996); and Ding et al., *Adv. Expt. Med. Biol.* 376:261–269, (1995), each of which is incorporated by reference); lipoprotein libraries (de Kruif et al., *FEBS Lett.* 399:232–236, (1996), which is incorporated herein by reference); glycoprotein or glycolipid libraries (Karaoglu et al., *J. Cell Biol.* 130:567–577 (1995), which is incorporated herein by reference); or chemical libraries containing, for example, drugs or other pharmaceutical agents (Gordon et al., *J. Med. Chem.* 37:1385–1401 (1994); Ecker and Crook, *Bio/Technology* 13:351–360 (1995); each of which is incorporated by reference). Such libraries, if desired, can be tagged, which can facilitate recovery of the molecule from an organ or tissue or its identification as previously described.

In vivo panning provides a method for directly identifying molecules that can selectively home to an organ or tissue. As used herein, the term "home" or "selectively home" means that a particular molecule binds relatively specifically to a target molecule present in the organ or tissue, particularly in the vasculature present in the organ or tissue, following administration to a subject. In general, selective homing is characterized, in part, by detecting at least a two-fold (2×) greater selective binding of the molecule to an organ or tissue as compared to a control organ or tissue.

Selective homing of a molecule to a selected organ or tissue can be due to selective recognition by the molecule of a particular cell target molecule such as a cell surface protein present on a cell in the organ or tissue. Selectivity of homing is dependent on the particular target molecule being expressed on only one or a few different cell types, such that the molecule homes to only one or a few organs or tissues. In this regard, most different cell types, particularly cell types that are unique to an organ or tissue, can express unique target molecules. Thus, in organs such as liver, spleen or lymph node, where blood circulates through sinusoids formed by the cells specific for the organ, in vivo panning can be useful for identifying molecules that home to the particular organ or tissue.

It should be recognized that, in some instances, a molecule can localize nonspecifically to an organ or tissue. For example, in vivo panning of a phage display library can result in high background in organs such as liver and spleen, which contain a marked component of the reticuloendothelial system (RES). Thus, nonspecific binding of molecules due to uptake by the RES of such an organ or tissue can make identifying an organ or tissue homing molecule more difficult. However, as disclosed herein, potential nonspecific binding can be circumvented, for example, by perfusion through the heart prior to collecting the selected organ or tissue (Example I).

In addition, selective homing readily can be distinguished from nonspecific binding by detecting differences in the abilities of different individual phage to home to an organ or tissue. For example, selective homing can be identified by combining a putative homing molecule such as a peptide expressed on a phage with an excess of non-infective phage or with about a five-fold excess of phage expressing unselected peptides, injecting the mixture into a subject and collecting a sample of the organ or tissue. In the latter case, for example, provided the portion of injected phage in which an organ or tissue homing peptide is sufficiently low so as to be nonsaturating for the target molecule, a determination that greater than about 20% of the phage in the organ or tissue contain the putative homing molecule is demonstrative evidence that the peptide expressed by the phage is a selective organ or tissue homing molecule. In addition, nonspecific localization can be distinguished from selective homing by performing competition experiments using, for example, phage expressing a putative organ or tissue homing peptide in combination with an excess amount of the "free" peptide (see Example II).

Various methods can be used to prevent nonspecific localization of a molecule to organs or tissues, such as those containing a component of the RES. For example, as disclosed herein, perfusion of a solution through the heart shortly after initiating phage circulation decreased the background binding and allowed identification of peptides that selectively home to lung and liver, both of which contain a component of the RES (see Example II). Furthermore, coadministration of nonreplicating control phage with a phage display library reduced nonspecific phage trapping in organs such as liver and spleen, which also contain a component of the RES. This approach allowed identification of molecules that selectively home to liver (Example II). Thus, a library of molecules attached to a support can be coadministered with an excess of the support to a subject to inhibit nonspecific binding in an organ or tissue.

Nonspecific uptake by a component of the RES also can be prevented by administering a blocking agent that inhibits uptake by the RES. For example, polystyrene latex particles or dextran sulfate can be administered to the subject prior to the administration of the library (see Kalin et al., *Nucl. Med. Biol.* 20:171–174 (1993); Illum et al., *J. Pharm. Sci.* 75:16–22 (1986); Takeya et al., *J. Gen. Microbiol.* 100:373–379 (1977), each of which is incorporated herein by reference). Such pre-administration of dextran sulfate 500 or polystyrene microspheres has been used to block nonspecific uptake of a test substance by Kupffer cells, which are the RES component of the liver (Illum et al., supra, 1986). Similarly, nonspecific uptake of agents by the RES has been blocked using carbon particles or silica (Takeya et al., supra, 1977) or a gelatine colloid (Kalin et al., supra, 1993). Thus, many methods useful for inhibiting nonspecific uptake by the RES are known in the art and routinely used.

Methods of decreasing nonspecific phage trapping include using phage that display a low background binding to a particular organ or tissue. For example, Merrill et al. (*Proc. Natl. Acad. Sci., USA* 93:3188–3192 (1996), which is incorporated herein by reference) selected lambda-type phage that are not taken up by the RES and, as a result, remain in the circulation for a prolonged period of time. A comparable filamentous phage variant, for example, can be selected using similar methods.

Selective homing can be demonstrated by determining if a homing molecule for a selected organ or tissue is relatively specific. For example, the amount of homing molecule in a selected organ or tissue can be compared to a control or different organ or tissue. Selective homing also can be demonstrated by showing that molecules that home to an organ or tissue, as identified by one round of in vivo panning, are enriched for in a subsequent round of in vivo panning. For example, phage expressing the peptides CGFECVRQCPERC (SEQ ID NO: 1) and CGFELETC (SEQ ID NO: 2) were enriched for in the second and third rounds of in vivo panning from lung and exhibited a 35-fold and 9-fold enrichment, respectively, as compared to unselected phage (see Example II.B). Furthermore, no selective homing to kidney or brain was detected.

As used herein, the term "selected organ or tissue" is used in its broadest sense to mean a normal organ or tissue or an organ or tissue having a pathology, for example, lung containing lung tumors, to which a molecule can selectively home. Thus, the term "organ or tissue" is used broadly to mean any tissue or organ including a normal or pathological cell type such as a cancer cell, in which case the selected organ or tissue can be a primary tumor or a metastatic lesion.

In general, a selected organ or tissue contains a cell, which can be a cell of the vasculature, that expresses a particular target molecule such as a cell surface protein to which a homing molecule can bind. By performing at least two rounds of in vivo panning, the selectivity of homing of the molecule for the selected organ or tissue can be determined. As discussed below, however, in some cases a homing molecule can home to more than one selected organ or tissue, in which case the molecule is considered to be able to selectively home to a family of selected organs or tissues. Generally, however, molecules that home to more than one or a few different organs or tissue are not particularly useful since an advantage of the homing molecules of the invention is that they allow targeting of a particular organ or tissue.

The term "control organ or tissue" is used to mean an organ or tissue other than the selected organ or tissue. A control organ or tissue is characterized by the inability of the organ or tissue homing molecule to home to the control organ or tissue and, therefore, is useful for identifying selective binding of a molecule to a selected organ or tissue (Example II). Where an organ or tissue homing molecule is identified based on its ability to home to a pathologic lesion in an organ or tissue, the control organ or tissue can be a corresponding portion of the selected organ or tissue that does not exhibit the pathologic lesion.

A control organ or tissue can be collected, for example, to identify nonspecific binding of the molecule or to determine the selectivity of homing of the molecule. In addition, nonspecific binding can be identified by administering, for example, a control molecule, which is known not to home to an organ or tissue but is chemically similar to a putative homing molecule. Alternatively, where the administered molecules are linked to a support, administration of the support, alone, can be used to identify nonspecific binding. For example, a phage that does not contain a peptide fusion protein can be administered to a subject and the selected organ or tissue can be examined to determine the level of nonspecific binding of the phage support.

The steps of administering the library to the subject, collecting a selected organ or tissue and identifying the molecules that home to the organ or tissue, comprise a single round of in vivo panning. Although not required, one or more additional rounds of in vivo panning generally are performed. Where an additional round of in vivo panning is performed, the molecules recovered from the selected organ or tissue in the previous round are administered to a subject, which can be the same subject used in the previous round, where only a part of the organ or tissue was collected.

By performing a second round of in vivo panning, the relative binding selectivity of the molecules recovered from the first round can be determined by administering the identified molecules to a subject, collecting the selected organ or tissue, and determining whether more phage displaying a particular molecule are recovered from the organ or tissue following the second round of screening as compared to those recovered following the first round. Although not required, a control organ or tissue also can be collected and the molecules recovered from the selected organ or tissue can be compared with those recovered from the control organ or tissue. Ideally, few if any molecules are recovered from a control organ or tissue following a second or subsequent round of in vivo panning. Generally, however, a proportion of the molecules also will be present in a control organ or tissue. In this case, the ratio of molecules in the selected organ or tissue as compared to the control organ or tissue (selected:control) can be determined. Additional rounds of in vivo panning can be used to determine whether a particular molecule homes only to the selected organ or tissue or can recognize a target expressed in one or more other organs or tissues that is identical or is sufficiently similar to the target in the originally selected organ or tissue.

In general, a library of molecules, which contains a diverse population of random or selectively randomized molecules of interest, is prepared, then administered to a subject. Some time after administration, the selected organ or tissue is collected and the molecules present in the selected organ or tissue are identified (see Example I). If desired, one or more control organs or tissues or a part of a control organ or tissue are sampled as well. For example, mice injected with a phage peptide display library, after about 1 to 5 minutes, were anesthetized, then snap frozen or perfused through the heart to terminate circulation of the phage. Lung, pancreas or other organs or tissues and one or more control organs were collected and the phage present in the selected and control organs were collected. The peptides that selectively homed to the respective organs or tissues were identified (Example II and Tables 1 to 11).

As exemplified herein, experimental animals were sacrificed to collect the selected or control organ or tissue. It should be recognized, however, that only a part of an organ or tissue need be collected to recover a molecule that homes to that organ or tissue. Similarly, only part of an organ or tissue need be collected as a control. Thus, for example, following administration of a library of molecules to a subject, a part of the selected organ or tissue can be collected by biopsy, the homing molecules can be collected and, if desired, amplified and readministered to the same subject for a second round of in vivo panning. Where the molecule that is to be administered a second time to the same subject is tagged or linked, for example, to a support, the tag or support should be biologically inert and biodegradable or excretable, so as not to interfere with subsequent rounds of screening.

In vitro screening of phage libraries previously was used to identify peptides that bind to antibodies or to cell surface receptors (Smith and Scott, supra, 1993). For example, in vitro screening of phage peptide display libraries identified novel peptides that specifically bound to integrin adhesion receptors (Koivunen et al., *J. Cell Biol.* 124:373–380 (1994a), which is incorporated herein by reference) and to the human urokinase receptor (Goodson et al., *Proc. Natl. Acad. Sci., USA* 91:7129–7133 (1994), which is incorporated herein by reference). Similarly, in vitro screening of nucleic acid molecules identified molecules that specifically bind to antibodies, cell surface receptors or organic molecules (Gold et al., supra, 1993, 1995, 1997). For example, RNA molecules that specifically bind to HIV-1 reverse transcriptase were identified using purified HIV-1 reverse transcriptase as the target molecule (Green et al., *J. Mol. Biol.,* 247:60–68 (1995), which is incorporated herein by reference). These in vitro methods were performed using defined, well-characterized target molecules in an artificial system. However, such in vitro studies provide no insight as to whether a molecule that binds in vitro also can bind to the target in vivo. For example, endothelial cells grown in culture tend to lose their tissue-specific differences (Pauli and Lee, *Lab. Invest.* 58:379–387 (1988), which is incorporated herein by reference). Thus, a molecule that binds to a target on a cell in vitro may not bind in vivo because the target may not be present on the cell. Furthermore, such in vitro methods are limited in that they require prior knowledge of the target molecule and yield little if any information regarding in vivo utility. For example, Goodson et al. (supra, 1994) utilized cultured cells to express a recombinant urokinase receptor to obtain binding peptides. However, the urokinase receptor is expressed in cells of many different organs and tissues and, therefore, a molecule that binds to it can interact with many organs or tissues and would not be considered an organ or tissue homing molecule within the present invention.

In contrast to in vitro panning methods, in vivo panning requires no prior knowledge or the availability of a known target molecule to identify a molecule that binds to a target molecule that is expressed in vivo. Also, since "nontargeted" organs or tissues are present during the screening, the probability of isolating organ or tissue homing molecules that lack selectivity of homing is greatly reduced. Furthermore, in obtaining organ or tissue homing molecules by in vivo panning, any molecules that may be particularly susceptible to degradation in the circulation in vivo due, for example, to a metabolic activity, will be selected against and will not be recovered. Thus, in vivo panning provides significant advantages over previous methods by identifying molecules that selectively home in vivo and, if desired, the target molecule present on a selected organ or tissue.

The identification of the organ homing molecules that selectively home to various normal tissues and to pathologic lesions in a particular organ or tissue, as exemplified herein, indicates that particular endothelial cell target molecules expressed the selected organ or tissue reflects the physiologic or pathologic state of the organ or tissue. Such organ homing molecules that selectively home to an organ or tissue based on a particular physiologic or pathologic condition occurring in the organ or tissue can be identified using the in vivo panning method and the selectivity of the homing molecules for the pathologic or physiologic condition of the organ or tissue can be confirmed by immunohistological analysis (Example III). For example, molecules that home to pancreas afflicted with pancreatitis can be identified by in vivo panning of a subject having pancreatitis and selectively of the homing molecule can be confirmed by using immunohistochemistry to compare homing of the molecule in normal pancreas with homing in a pancreas afflicted with pancreatitis.

Homing molecules selective for a normal organ or tissue or an organ or tissue exhibiting a pathological state can be useful for detecting the presence or absence of the pathology. For example, following administration of a prostate homing molecule conjugated to an imaging moiety to a subject, the prostate can be visualized. If the image is abnormal, for example, if the size of the prostate is other than that expected for a size and age matched subject, the imaging result can indicate an abnormal physiologic condition or pathologic condition afflicting the prostate. For example, a conjugate comprising an imaging agent and a prostate homing molecule that homes to normal, but not to abnormal prostate, can be administered to a subject. The identification, for example, of a region of the prostate that does not bind the homing molecule can indicate the occurrence of abnormal blood flow in the prostate and can be diagnostic of a pathologic condition such as the presence of a prostate tumor. A conjugate comprising a molecule that homes to prostate tumor tissue, but not to normal prostate, can be used to image a prostate tumor directly.

A homing molecule selective for an organ or tissue can be used to deliver a therapeutic agent to the organ or tissue. Such selective targeting of the agent can increase the effective amount of the agent delivered to the target organ or tissue, while reducing the likelihood the agent will have an adverse effect on other organs or tissues. For example, a lung homing molecule can be used to deliver, to the lung of a cystic fibrosis patient, a gene encoding the cystic fibrosis transmembrane receptor (CFTR), which is defective in cystic fibrosis. Thus, the organ homing molecules of the invention are particularly useful for in vivo gene therapy, since they provide a means to direct a gene to a desired target organ, thereby increasing the likelihood that the target cells will receive the gene and decreasing the likelihood that normal, nontarget, cells will be adversely affected. A lung homing molecule also can be used to direct a therapeutic agent to the lung, thus sparing nontarget organs or tissues from the toxic effects of the agent. For example, in alveolar bacterial pneumonia, a lung homing molecule can be useful for directing an antibiotic to the afflicted region of the lung, thus increasing the effective amount of the drug at the desired site.

Due to the conserved nature of cellular receptors and of ligands that bind a particular receptor, the skilled artisan would recognize that an organ or tissue homing molecule identified using in vivo panning in a mouse or rat also can bind to the corresponding target molecule in the selected organ or tissue of a human or other mammalian species. Such a homing molecule identified using an experimental animal readily can be examined for the ability to bind to the corresponding organ or tissue in a human subject by demonstrating, for example, that the molecule also can bind selectively in vitro to a sample of the selected organ or tissue obtained from a human subject. Alternatively, primary cells or established cell lines derived from a human organ or tissue can be used to test for the in vitro binding of the homing molecule. Similarly, primary cells or established cell lines that reflect a particular human organ or tissue pathology can be used to test the binding of homing molecules selective for the pathology. Animal models such as primate models of human pathologies are known and also can be used to test for the homing of the molecules using in vivo panning. Thus, routine methods can be used to confirm that an organ or tissue homing molecule identified using in vivo panning in an experimental animal also can bind an organ or tissue-specific target molecule in a human subject. Furthermore, in vitro contacting of a homing molecule with a sample suspected of containing a selected organ, tissue or pathology can identify the presence of the selected organ, tissue or pathology in the sample. Having identified the target molecule by in vivo panning, the artisan would know that it is the true target for an organ homing molecule and, therefore, would know that the target molecule could be used in vitro to identify addtional organ homing molecules that likely would be specific for the target molecule in vivo. Such potential organ homing molecules then could be examined by in vivo panning to confirm organ homing ability.

In vivo panning was used to identify peptides expressed by phage that selectively homed to lung, skin, pancreas, retina, prostate, ovary, lymph node, adrenal gland, liver or gut, and to lung containing lung tumors or pancreas containing a pancreatic tumor (Examples II and IV; see, also, Tables 2 to 11). Due to the large size of the phage (300 nm) and the short time the phage were allowed to circulate, it is unlikely that a substantial number of phage would have exited the circulatory system. Indeed, immunohistochemical studies of various organ and tissue homing molecules demonstrated that the molecules primarily home to and bind endothelial cell surface markers of the vasculature. Thus, the invention provides molecules such as peptides that selectively home to the vasculature of a selected organ or tissue.

Phage peptide display libraries were constructed essentially as described by Smith and Scott (supra, 1993; see, also, Koivunen et al., *Biotechnology* 13:265–270 (1995); Koivunen et al., *Meth. Enzymol.* 245:346–369 (1994b), each of which is incorporated herein by reference). In some libraries, at least one codon encoding cysteine also was included in each oligonucleotide so that cyclic peptides could be formed through disulfide linkages (Example I). Upon performing in vivo panning, peptides that selectively home to lung, pancreas, skin, retina, prostate, ovary, lymph node, adrenal gland, liver or gut or to lung containing lung tumors or to pancreas containing a pancreatic tumor were obtained. Thus, the invention provides various organ homing molecules that selectively home to particular organs or tissue.

Remarkably, some organ homing peptides independently were recovered up to four or more times during a round of the in vivo panning procedure (see, for example, Table 1). In addition, various peptides that homed to particular organs or tissues shared conserved amino acid sequence motifs. For example, some lung homing peptides shared a GFE motif; some

TABLE 1

SUMMARY OF IN VIVO TARGETING OF VARIOUS ORGANS

| ORGAN/MOTIF (SEQ ID NO:) | % OF MOTIF AMONG ALL CLONES | LUNG/ BRAIN RATIO |
|---|---|---|
| GUT | | |
| YSGKWGK (9) | 22 | 30 |
| GISALVLS (19) | 11 | nd |
| SRRQPLS (153) | 11 | 2 |
| MSPQLAT (159) | 11 | nd |
| MRRDEQR (172) | | |
| QVRRVPE (155) | | |
| VRRGSPQ (164) | | |
| GGRGSWE (167) | | |
| FRVRGSP (169) | | |
| RVRGPER (165) | | |
| LIVER | | |
| VKSVCRT (12) | 11 | nd |
| WRQNMPL (418) | 6 | nd |
| SRRFVGG (406) | 6 | nd |
| ALERRSL (408) | | |
| ARRGWTL (405) | | |
| PROSTATE | | |
| SMSIARL (21) | 6 | 34 |
| VSFLEYR (22) | 6 | 17 |
| RGRWLAL (279) | 6 | nd |
| ADRENAL GLAND | | |
| LMLPRAD (27) | 11 | 50 |
| LPRYLLS (28) | | |
| R (Y/F) LLAGG (404) | | |
| RYPLAGG (389) | | |
| OVARY | | |
| EVRSRLS (10) | 22 | 3 |
| FFAAVRS (295) | | |
| VRARLMS (301) | | |
| RVGLVAR (11) | 22 | 5 |
| RVRLVNL (294) | | |
| PANCREAS | | |
| SWCEPGWCR (4) | | 20 |
| SKIN | 9 | |
| CVALCREACGEGC (3) | 6 | 7 |

TABLE 1-continued

SUMMARY OF IN VIVO TARGETING OF VARIOUS ORGANS

| ORGAN/MOTIF (SEQ ID NO:) | % OF MOTIF AMONG ALL CLONES | LUNG/ BRAIN RATIO |
|---|---|---|
| CSSGCSKNCLEMC (181) | | 2 |
| LUNG | | |
| CTLRDRNC (15) | 10 | 8 |
| CGKRYRNC (20) | 5 | 5 |
| CLRPYLNC (45) | 10 | 6 |
| CGFELETC (2) | 5 | 9 |
| CIGEVEVC (16) | 5 | 6 |
| CKWSRLHSC (65) | 11 | 3 |
| CWRGDRKIC (56) | 8 | 2 |
| CERVVGSSC (59) | 9 | 4 |
| CLAKENVVC (13) | 13 | 2 |
| CTVNEAYKTRMC (75) | 22 | 3 |
| CRLRSYGTLSLC (76) | 5 | 0.4 |
| CRPWHNQAHTEC (82) | 14 | 5 |
| CGFECVRQCPERC (1) | 40 | 60 | retina homing peptides shared a RDV motif; and some adrenal gland homing peptides shared a LPR motif (see Tables 2, 6 and 11, respectively). Since it is known, for example, that the tripeptide RGD motif is sufficient for integrin binding (Ruoslahti, *Ann. Rev. Cell Devel. Biol.* 12:697 (1996); Koivunen et al., supra, 1995; WO 95/14714), the results disclosed herein indicate that many ligand/receptor interactions can derive their specificity from recognition motifs as small as tripeptides.

None of the sequences of the disclosed organ homing peptides exhibited significant similarity with known ligands for endothelial cell receptors. While many of the organ homing peptides may be contained within larger peptides or proteins, it is not known whether they are able to impart a homing function onto the larger molecule. Based on the previous finding that RGD mediates integrin binding when present within larger peptides and proteins, one skilled in the art would recognize, however, that such homing peptides and motifs could impart a homing function when located within a larger peptide or protein. However, such naturally occurring endogenous peptides and proteins are not considered to be organ or tissue homing molecules within the invention.

The organ or tissue homing peptide molecules exemplified herein range in size from about 7 to 13 amino acids in length. However, based, for example, on the ability of the RGD integrin binding motif to mediate integrin binding by itself or when present in a large protein, it will be recognized that the organ homing molecules of the invention also can be expected to maintain their homing capability in the context of a significantly longer polypeptide sequence. Thus, an organ homing peptide of the invention can be at least three amino acids, generally at least six amino acids or seven amino acids or more, and can be significantly larger, for example, about 20 to 50 amino acids or 100 amino acids or more.

The invention provides lung homing peptides such as CGFECVRQCPERC (SEQ ID NO: 1) and CGFELETC (SEQ ID NO: 2), which share a GFE motif; CTLRDRNC (SEQ ID NO: 15); and CIGEVEVC (SEQ ID NO: 16; see Table 1), which contains an EVE motif that is similar to the ELE motif present in CGFELETC (SEQ ID NO: 2). The exemplified lung homing peptides were identified by injection of a $CX_3CX_3CX_3C$, (SEQ ID NO: 25), $CX_7C$ (SEQ ID NO: 24) or $CX_6C$ (SEQ ID NO: 26) cyclic library into mice (Example II). The lung homing peptides CGFECVRQC- PERC (SEQ ID NO: 1) and CGFELETC (SEQ ID NO: 2) exhibited a 60-fold and 9-fold enrichment, respectively, as compared to unselected phage, with few phage detected in kidney or brain (Example II; see, also, FIGS. 1 and 2 and Table 1). In addition, the lung homing peptides CTLRDRNC (SEQ ID NO: 15) and CIGEVEVC (SEQ ID NO: 16) exhibited a 8-fold and 6-fold enrichment, respectively, over unselected phage (Table 1). Coinjection of a glutathione-S-transferase-(GST-)CGFECVRQCPERC (SEQ ID NO: 1) fusion peptide with phage expressing the cognate CGFECVRQCPERC (SEQ ID NO: 1) peptide inhibited homing by 70%, and coinjection of GST-CGFELETC (SEQ ID NO: 2) with phage expressing (SEQ ID NO: 2) inhibited lung homing by 30% (FIG. 3). Immunohistochemical staining of lung following administration of phage displaying a lung homing peptide to mice revealed staining within the alveolar capillaries. No apparent preference for homing of the phage to any particular region of the lung was observed; however, no staining was observed in bronchiolar walls or some larger blood vessels (Example III), or in many other tissues analyzed. These results indicate that in vivo panning can be used to identify and analyze endothelial cell specificities within lung, thus providing a means to differentially target lung.

The invention also provides skin homing peptides such as CVALCREACGEGC (SEQ ID NO: 3; Table 5), which were identified by injection of a $CX_3CX_3CX_3C$ (SEQ ID NO: 25) cyclic library into mice (Example II). The skin homing peptide sequence CVALCREACGEGC (SEQ ID NO: 3) exhibited a 7-fold selectivity for skin over unselected phage and over background in brain and kidney (FIG. 2; see, also, Table 1). Coinjection of GST-CVALCREACGEGC (SEQ ID NO: 3) with phage expressing CVALCREACGEGC (SEQ ID NO: 3) inhibited homing to skin by 55%, whereas coinjection with GST, alone, had no effect on homing (see FIG. 3B). Immunohistochemical staining of skin following administration of phage displaying a skin homing peptide revealed that staining was localized to the hypodermis; no staining was observed in the dermis (Example III).

The invention further provides pancreas homing peptides such as SWCEPGWCR (SEQ ID NO: 4; Table 3). The exemplified pancreas homing molecules were identified by injection of a $CX_7C$ (SEQ ID NO: 24) or $X_2CX_4CX$ (SEQ ID NO: 23) cyclic library into mice (Example II). The pancreas homing peptide SWCEPGWCR (SEQ ID NO: 4) exhibited a 20-fold selectivity for pancreas over unselected phage and over brain (Table 1; FIG. 2). However, coinjection of GST-SWCEPGWCR (SEQ ID NO: 4) did not inhibit SWCEPGWCR (SEQ ID NO: 4) pancreas homing, presumably due to a conformational effect of GST on the pancreas homing peptide. Immunohistochemical staining of pancreas following administration of phage displaying a pancreas homing peptide revealed that staining was localized to the capillaries as well as larger blood vessels of the exocrine pancreas; no significant staining was observed in the endocrine vasculature (Example III). This result demonstrates that histologically and physiologically distinguishable regions within a particular organ can express unique target molecules, which provide a target for an organ homing molecule of the invention. Accordingly, the organ homing molecules of the invention provide a means to differentially targeted specific regions of a selected organ or tissue.

Retina homing peptides such as CSCFRDVCC (SEQ ID NO: 5) and CRDVVSVIC (SEQ ID NO: 6) also are provided (see Table 6). The exemplified retina homing molecules were identified by injection of a $CX_7C$ (SEQ ID NO: 24) cyclic library into rats (Example II). The retina homing peptides CSCFRDVCC (SEQ ID NO: 5) and CRDVVSVIC (SEQ ID NO: 6), when injected individually with a control fdAMPLAY88 phage, exhibited a 3-fold and 2-fold enrichment, respectively, in retina (Example II). However, immunohistochemical staining revealed an absence of retina staining, presumably due to a relatively modest accumulation of the retina homing phage in the target tissue.

The invention also provides prostate homing peptides such as SMSIARL (SEQ ID NO: 21) and VSFLEYR (SEQ ID NO: 22), which were identified by injection of an $X_7$ (SEQ ID NO: 29) library into mice (Table 7). The peptides were isolated by the regular method. The prostate homing peptides SMSIARL (SEQ ID NO: 21) and VSFLEYR (SEQ ID NO: 22) exhibited a 34-fold and 17-fold enrichment, respectively, in prostate as compared to brain (Table 1).

Also provided are ovary homing peptides such as RVGL-VAR (SEQ ID NO: 11) and EVRSRLS (SEQ ID NO: 10), which were identified by injection of an $X_7$ (SEQ ID NO: 29) library into mice (Table 8). The peptides were isolated by the regular method. The ovary homing peptides RVGL-VAR (SEQ ID NO: 11) and EVRSRLS (SEQ ID NO: 10) each comprised 22% of 40 clones sequenced and exhibited a 5-fold and a 3-fold enrichment, respectively, in ovary as compared to brain (Table 1).

The invention also provides adrenal gland homing peptides such as LMLPRAD (SEQ ID NO: 27) and LPRYLLS (SEQ ID NO: 28), which share a LPR motif (see Table 11), or the peptides R(Y/F)LLAGG (SEQ ID NO: 404) and RYPLAGG (SEQ ID NO: 389), which share the motif LAGG (SEQ ID NO: 430; see Table 10). The exemplified adrenal gland homing peptides were identified by injection of an $X_7$ (SEQ ID NO: 29) library into mice. The peptides were isolated by the regular method. The adrenal gland homing peptide LMLPRAD (SEQ ID NO: 27) exhibited a 50-fold enrichment in adrenal gland as compared to brain (Table 1).

Also provided are liver homing peptides. Such peptides were identified by injection of an $X_7$ (SEQ ID NO: 29) library into mice. The peptides were isolated by the regular method (see Example II, Table 1, and Table 11, below).

In addition, lymph node homing peptides, such as AGCS-VTVCG (SEQ ID NO: 315) are provided (Table 9, below). Such peptides were identified by injection of an $X_2CX_4CX$ (SEQ ID NO: 23) library into mice. The peptides were isolated by the regular method.

The invention also provides gut homing peptides such as YSGKWGK (SEQ ID NO: 9) and YSGKWGW (SEQ ID NO: 156), which were identified by injection of an $X_7$ (SEQ ID NO: 29) library into mice (Tables 1 and 4) and differ only in the last amino acid position. The peptides were isolated by the regular method. The gut homing peptide YSGKWGK (SEQ ID NO: 9) was present in 22% of 40 clones sequenced and was enriched 30-fold in gut as compared to brain (Table 1). In addition, gut homing peptides such as QVRRVPE (SEQ ID NO: 155) and VRRGSPQ (SEQ ID NO: 164), which share a VRR motif, were identified, as were the peptides VRRGSPQ (SEQ ID NO: 164), GGRGSWE (SEQ ID NO: 167) and FRVRGSP (SEQ ID NO: 169), which share an RGS motif.

The organ homing molecules of the invention are particularly useful as conjugates, which comprise the organ homing molecule linked to a moiety. Thus, a lung, skin, pancreas, retina, prostate, ovary, lymph node, adrenal gland, liver or gut homing molecule of the invention can be linked to a moiety, such conjugates being useful for directing the moiety to the particular selected organ.

As used herein, the term "moiety" is used broadly to mean a physical, chemical, or biological material that is linked to an organ or tissue homing molecule. Generally, a moiety linked to an organ homing molecule imparts a biologically useful function to the homing molecule. A moiety can consist of any natural or nonnatural material for example, peptide or polypeptide sequences, organic or inorganic molecules or compositions, nucleic acid molecules, carbohydrates, lipids or combinations thereof.

A moiety can be a physical, chemical or biological material such as a virus, viral gene therapy vector, cell, liposome, microcapsule, micropump or other chambered microdevice, which can be used, for example, as a drug delivery system. Generally, such microdevices should be biologically inert and, if desired, biodegradable or excretable. Various moieties, including microcapsules, which can contain an agent, and methods for linking a moiety or chambered microdevice to an organic molecule of the invention are well known in the art and commercially available (see, for example, "Remington's Pharmaceutical Sciences" 18th ed. (Mack Publishing Co. 1990), chapters 89–91; Harlow and Lane, *Antibodies: A laboratory manual* (Cold Spring Harbor Laboratory Press 1988), each of which is incorporated herein by reference; see, also, Hermanson, supra, 1996). Additional examples of moieties are known to those skilled in the art and are intended to be included within the meaning of the term so long as they possess a biologically useful function when linked to the homing molecules of the invention.

Linking of a moiety to an organ homing molecule for the purpose of directing the moiety to the selected organ or tissue was demonstrated by the linking of a brain homing peptide to a red blood cell (RBC), wherein the peptide directed homing of the RBC to the brain (U.S. Pat. No. 5,622,699, supra, 1997). These results indicate that an organ or tissue homing molecule of the invention can be linked to another moiety in order to direct the moiety to a selected organ or tissue. For example, a liver homing molecule or a lung homing molecule can be linked to a nucleic acid encoding the CFTR gene and upon administration to a subject, expression of CFTR is targeted to the liver or to the lung, respectively. Similarly, a lung homing molecule can be linked to a protease inhibitor such that, upon administration of the conjugate comprising the lung homing molecule and the protease inhibitor to a subject, the protease inhibitor is targeted to the lung. Such a conjugate can be useful, for example, for treating a subject suffering from emphysema, which is characterized by excessive protease production in the lungs and autodigestion of the organ.

An organ and tissue homing molecule of the invention can be useful for directing to a selected organ or tissue a therapeutic agent, diagnostic agent or imaging agent, a tag or insoluble support, a liposome or a microcapsule comprising, for example, a permeable or semipermeable membrane, wherein an agent such as a drug to be delivered to a selected organ or tissue is contained within the liposome or microcapsule. These and other moieties known in the art can be used in a conjugate of the invention, and in a method of the invention, as disclosed herein.

In one embodiment, a moiety can be a detectable agent such as a radionuclide or an imaging agent, which allows detection or visualization of the selected organ or tissue. Thus, the invention provides a conjugate comprising a lung, skin, pancreas, retina, prostate, ovary, lymph node, adrenal gland, liver or gut homing molecule, linked to a detectable agent. The type of detectable agent selected will depend upon the application. For example, for an in vivo diagnostic imaging study of the lung in a subject, a lung homing molecule can be linked to an agent that, upon administration to the subject, is detectable external to the subject. For detection of such internal organs or tissues, for example, the prostate, a gamma ray emitting radionuclide such as indium-113, indium-115 or technetium-99 can be linked to a prostate homing molecule and, following administration to a subject, can be visualized using a solid scintillation detector. Alternatively, for organs or tissues at or near the external surface of a subject, for example, retina, a fluorescein-labeled retina homing molecule can be used such that the endothelial structure of the retina can be visualized using an opthalamoscope and the appropriate optical system.

Molecules that selectively home to a pathological lesion in an organ or tissue similarly can be linked to an appropriate detectable agent such that the size and distribution of the lesion can be visualized. For example, where an organ or tissue homing molecule homes to a normal organ or tissue, but not to a pathological lesion in the organ or tissue, the presence of the pathological lesion can be detected by identifying an abnormal or atypical image of the organ or tissue, for example, the absence of the detectable agent in the region of the lesion.

A detectable agent also can be an agent that facilitates detection in vitro. For example, a conjugate comprising a homing molecule linked to an enzyme, which produces a visible signal when an appropriate substrate is present, can detect the presence of an organ or tissue to which the homing molecule is directed. Such a conjugate, which can comprise, for example, alkaline phosphatase or luciferase or the like, can be useful in a method such as immunohistochemistry. Such a conjugate also can be used to detect the presence of a target molecule, to which the organ homing molecule binds, in a sample, for example, during purification of the target molecule.

In another embodiment, a moiety can be a therapeutic agent. Thus, the invention provides a conjugate comprising a lung, skin, pancreas, retina, prostate, ovary, lymph node, adrenal gland, liver or gut homing molecule linked to a therapeutic agent.

A therapeutic agent can be any biologically useful agent that, when linked to an organ homing molecule of the invention, exerts its function at the site of the selected organ or tissue. For example, a therapeutic agent can be a small organic molecule that, upon binding to a target cell due to the linked organ homing molecule, is internalized by the cell where it can effect its function. A therapeutic agent can be a nucleic acid molecule that encodes a protein involved in stimulating or inhibiting cell survival, cell proliferation or cell death, as desired, in the selected organ or tissue. For example, a nucleic acid molecule encoding a protein such as Bcl-2, which inhibits apoptosis, can be used to promote cell survival, whereas a nucleic acid molecule encoding a protein such as Bax, which stimulates apoptosis, can be used to promote cell death of a target cell.

A particularly useful therapeutic agent that stimulates cell death is ricin, which, when linked to an organ homing molecule of the invention, can be useful for treating a hyperproliferative disorder, for example, cancer. A conjugate comprising an organ homing molecule of the invention and an antibiotic, such as ampicillin or an antiviral agent such as ribavirin, for example, can be useful for treating a bacterial or viral infection in a selected organ or tissue.

A therapeutic agent also can inhibit or promote the production or activity of a biological molecule, the expression or deficiency of which is associated with the pathology. Thus, a protease inhibitor can be a therapeutic agent that, when linked to an organ homing molecule, can inhibit protease activity at the selected organ or tissue, for example, the pancreas. A gene or functional equivalent thereof such as a cDNA, which can replenish or restore production of a protein in a selected organ or tissue, also can be a therapeutic agent useful for ameliorating the severity of a pathology. A therapeutic agent also can be an antisense nucleic acid molecule, the expression of which inhibits production of a deleterious protein, or can be a nucleic acid molecule encoding a dominant negative protein or a fragment thereof, which can inhibit the activity of a deleterious protein.

In another embodiment, the invention provides a conjugate comprising a lung, skin, pancreas, retina, prostate, ovary, lymph node, adrenal gland, liver or gut homing molecule linked to a tag. A tag can be, for example, an insoluble support such as a chromatography matrix, or a molecule such as biotin, hemagglutinin antigen, polyhistidine, T7 or other molecules known in the art. Such a conjugate comprising a tag can be useful to isolate a target molecule, to which the organ homing molecule binds.

When administered to a subject, a conjugate comprising an organ homing molecule and a moiety is administered as a pharmaceutical composition containing, for example, the conjugate and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of the complex. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. The pharmaceutical composition also can contain an agent such as a cancer therapeutic agent or other therapeutic agent as desired.

One skilled in the art would know that a pharmaceutical composition containing an organ homing molecule can be administered to a subject by various routes including, for example, orally or parenterally, such as intravenously. The composition can be administered by injection or by intubation. The pharmaceutical composition also can be an organ homing molecule linked to a moiety such as a liposome or other polymer matrix, which can have incorporated therein, for example, a drug that promotes or inhibits cell death (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

In performing a diagnostic or therapeutic method as disclosed herein, an effective amount of a conjugate comprising an organ homing molecule must be administered to the subject. An "effective amount" is the amount of the conjugate that produces a desired effect. An effective amount will depend, for example, on the moiety linked to the organ homing molecule and on the intended use. For example, a lesser amount of a radiolabeled homing molecule can be required for imaging as compared to the amount of the radiolabeled molecule administered for therapeutic purposes, where cell killing is desired. An effective amount of a particular conjugate for a specific purpose can be determined using methods well known to those in the art.

The route of administration of an organ molecule will depend, in part, on the chemical structure of the organ homing molecule. Peptides, for example, are not particularly useful when administered orally because they can be degraded in the digestive tract. However, methods for chemically modifying peptides to render them less susceptible to degradation by endogenous proteases or more absorbable through the alimentary tract are well known (see, for example, Blondelle et al., supra, 1995; Ecker and Crooke, supra, 1995; Goodman and Ro, supra, 1995). Such methods can be performed on peptides that home to a selected organ or tissue. In addition, methods for preparing libraries of peptide analogs such as peptides containing D-amino acids; peptidomimetics consisting of organic molecules that mimic the structure of a peptide; or peptoids such as vinylogous peptoids, have been previously described above and can be used to identify homing molecules suitable for oral administration to a subject.

The invention provides methods of identifying a selected organ or tissue by administering to a subject a conjugate comprising a lung, skin, pancreas, retina, prostate, ovary, lymph node, adrenal gland, liver or gut and a detectable agent. A conjugate comprising an organ homing molecule of the invention linked to a detectable moiety conjugate can be administered to a subject and used to identify or visualize a selected organ or tissue. The ability to visualize an organ, particularly an internal organ, provides a means diagnose a pathology of the selected organ or tissue. For example, a prostate homing molecule linked to indium-113 can be administered to a subject in order to image the prostate. Such a method can be particularly valuable because methods for imaging the prostate are limited. The presence of a prostate pathology can be revealed by detecting that a region of the prostate does not contain the conjugate, thus indicating an abnormality in circulation to the region, or by detecting that the prostate is abnormally enlarged or lacking its normal boundaries. For organs or tissues such as retina, which can be visualized directly using an ophthalmoscope, a conjugate comprising a retina homing molecule linked to fluorescein can be administered to a subject and used to examine the vascular integrity and circulation in the retina. The absence of a normal or typical pattern of retinal image can indicate the presence of a retinal pathology in the region. For example, an abnormal retinal pattern can reflect vascular changes indicative of a hyperproliferative or degenerative pathology.

In principle, an organ homing molecule of the invention can have an inherent biological property, such that administration of the molecule provides direct biological effect. For example, an organ homing molecule can be sufficiently similar to a naturally occurring ligand for the target molecule that the organ homing molecule mimics the activity of the natural ligand. Such an organ homing molecule can be useful as a therapeutic agent having the activity of the natural ligand. For example, where the organ homing molecule mimics the activity of a growth factor that binds a receptor expressed by the selected organ or tissue, such as a skin homing molecule that mimics the activity of epidermal growth factor, administration of the organ homing molecule can result in cell proliferation in the organ or tissue. Such inherent biological activity of an organ homing molecule of the invention can be identified by contacting the cells of the selected organ or tissue with the homing molecule and examining the cells for evidence of a biological effect, for example, cell proliferation or, where the inherent activity is a toxic effect, cell death.

In addition, an organ homing molecule of the invention can have an inherent activity of binding a particular target molecule such that a corresponding ligand cannot bind the receptor. It is known, for example, that various types of cancer cells metastasize to specific organs or tissues, indicating that the cancer cells express a ligand that binds a target molecule in the organ to which it metastasizes. Thus, administration of a lung homing molecule, for example, to a subject having a tumor that metastasizes to lung, can provide a means to prevent the potentially metastatic cancer cell from becoming established in the lung. In general, however, the organ homing molecules of the invention are particularly useful for targeting a moiety to a selected organ or tissue, particularly to lung, skin, pancreas, retina, prostate, ovary, lymph node, adrenal gland, liver or gut. Thus, the invention provides methods of treating a pathology in a selected organ or tissue by administering to a subject having the pathology a conjugate comprising an organ homing molecule of the invention linked to a therapeutic agent.

Specific disorders of the lung, for example, can be treated by administering to a subject a conjugate comprising a lung homing molecule linked to a therapeutic agent. Since a lung homing molecule of the invention can localize to the capillaries and alveoli of the lung, disorders associated with these regions are especially amenable to treatment with a conjugate comprising the lung homing molecule. For example, bacterial pneumonia often originates in the alveoli and capillaries of the lung (Rubin and Farber, *Pathology* 2nd ed., (Lippincott Co.,1994)). Thus, a lung homing molecule conjugated to a suitable antibiotic can be administered to a subject to treat the pneumonia. Similarly, cystic fibrosis causes pathological lesions in the lung due to a defect in the CFTR. Thus, administration of a lung homing molecule conjugated to a nucleic acid molecule encoding the CFTR provides a means for directing the nucleic acid molecule to the lung as an in vivo gene therapy treatment method.

The invention also provides methods of treating a pathology of the skin by administering to a subject having the pathology a conjugate comprising a skin homing molecule and a therapeutic agent. For example, a burn victim can be administered a conjugate comprising a skin homing molecule linked to epithelial growth factor or platelet derived growth factor such that the growth factor is localized to the skin where it can accelerate regeneration or repair of the epithelium and underlying dermis. Furthermore, a method of the invention can be useful for treating skin pathologies caused by bacterial infections, particularly infections that spread through the hypodermis and dermis or that are localized in these regions, by administering to a subject a conjugate comprising a skin homing molecule linked to an antibiotic.

The invention also provides methods of treating a pathology of the pancreas by administering to a subject having the pathology a conjugate comprising a pancreas homing molecule linked to a therapeutic agent. In particular, since a pancreas homing molecule of the invention can localize to the exocrine pancreas, a pathology associated with the exocrine pancreas can be treated and, in some cases, may not adversely affect the endocrine pancreas. A method of the invention can be particularly useful to treat acute pancreatitis, which is an inflammatory condition of the exocrine pancreas caused by secreted proteases damaging the organ. A conjugate comprising a pancreas homing molecule linked to a protease inhibitor can be used to inhibit the protease mediated destruction of the tissue, thus reducing the severity of the pathology. Appropriate protease inhibitors useful in such a conjugate are those that inhibit enzymes associated with pancreatitis, including, for example, inhibitors of trypsin, chymotrypsin, elastase, carboxypeptidase and pancreatic lipase. A method of the invention also can be used to treat a subject having a pancreatic cancer, for example, ductal adenocarcinoma, by administering to the subject a conjugate comprising a therapeutic agent linked to a molecule that homes to pancreas.

The methods of the invention also can be used to treat a pathology of the eye, particularly the retina, by administering to a subject having the pathology a conjugate comprising a retina homing molecule linked to a therapeutic agent. For example, proliferative retinopathy is associated with neovascularization of the retina in response to retinal ischemia due, for example, to diabetes. Thus, administration of a conjugate comprising a retina homing molecule linked to a gene that stimulates apoptosis, for example, Bax, can be used to treat the proliferative retinopathy. Similarly, methods of the invention can be used to diagnose or treat prostate, ovary, lymph node, adrenal gland, liver, or gut pathology using the appropriate organ or tissue homing molecules disclosed herein either alone, or linked to a desired moiety.

An organ or tissue homing molecule is useful, for example, for targeting a therapeutic or detectable agent to the selected organ or tissue. In addition, an organ or tissue homing molecule can be used to identify the presence of a target molecule in a sample. As used herein, the term "sample" is used in its broadest sense to mean a cell, tissue, organ or portion thereof that is isolated from the body. A sample can be, for example, a histologic section or a specimen obtained by biopsy or cells that are placed in or adapted to tissue culture. If desired, a sample can be processed, for example, by homogenization, which can be an initial step for isolating the target molecule to which an organ or tissue homing molecule binds.

An organ homing molecule obtained as disclosed herein can be useful for identifying the presence of a target molecule, particularly a cell surface protein, that is recognized by the homing molecule, or for substantially isolating the target molecule. Thus, the invention provides methods of identifying target molecules that selectively bind a lung homing molecule, a skin homing molecule, a pancreas homing molecule, a retina homing molecule, a prostate homing molecule, an ovary homing molecule, a lymph node homing molecule, an adrenal gland homing molecule, a liver homing molecule or a gut homing molecule. Such a method comprises contacting a sample of the selected organ or tissue, for example, prostate, with a prostate homing molecule, and detecting selective binding of a component of a sample, wherein such binding identifies the presence of a target molecule.

An organ or tissue homing molecule such as a prostate homing peptide can be linked to a tag, for example, a solid support such as a chromatography matrix. The immobilized organ homing molecule then can be used for affinity chromatography by passing an appropriately processed sample of prostate tissue over a column containing the matrix under conditions that allow specific binding of the prostate homing molecule to the particular target molecule (see, for example, Deutshcer, *Meth. Enzymol.*, Guide to Protein Purification (Academic Press, Inc., ed. M. P. Deutscher, 1990), Vol. 182, which is incorporated herein by reference; see, for example, pages 357–379). Unbound and nonspecifically bound material can be removed and the target molecule, which forms a complex with the prostate homing molecule, can be eluted from the column and collected in a substantially isolated form. The substantially isolated prostate target molecule then can be characterized using well known methods. An organ or tissue homing molecule also can be linked to a detectable agent such as a radionuclide, a fluorescent molecule, an enzyme or a labeled biotin tag and can be used, for example, to screen a sample in order to detect the presence of the target molecule or to follow the target molecule during its isolation.

As an alternative to using an organ or tissue sample to identify a target molecule of the selected organ or tissue, extracts of cultured cells derived from the selected organ or tissue, or extracts of cultured endothelial cells can be used as the starting material. Selection of cells containing the target molecule can be determined by using binding and cell attachment assays (see Barry et al., *Nature Med.* 2:299–305 1996), which is incorporated herein by reference). Those cells containing the target molecule can be used to prepare extracts for the isolation and identification of a target molecule, as described above.

Upon identifying an appropriate cell line expressing the target molecule, the target molecule can be labeled by growing the cells in medium containing radiolabeled amino acids. The radiolabeled amino acids are incorporated into the target molecule, thus facilitating its identification during purification. Labeled cells then can be extracted with octylglucoside and the extract can be fractionated by affinity chromatography using a pancreas homing molecule coupled to a matrix such as SEPHAROSE. Extracts prepared, for example, from human umbilical vein endothelial cells can be used as a control. The purified target molecule then can be microsequenced and antibodies can be prepared. If desired, oligonucleotide probes can be prepared and used to isolate cDNA clones encoding the target receptor. Alternatively, an anti-receptor antibody can be used to isolate a cDNA clone from an expression library (see Argraves et al., *J. Cell Biol.* 105:1183–1190 (1987), which is incorporated herein by reference).

In addition to biochemically isolating a target molecule, a nucleic acid encoding the target molecule can be isolated by using, for example, a pancreas homing molecule as a chemical probe to screen a pancreatic cDNA expression library for clones that express the target molecule. For example, bacteria expressing a pancreatic cDNA library can be attached to a membrane, lysed, and screened with a pancreas homing molecule conjugated, for example, to an enzyme that produces a colorimetric or fluorescent signal. Bacterial clones expressing a target molecule are identified and the cDNA encoding the target molecule can be isolated. Additionally, a mammalian cell expression cloning system such as the COS cell system can be used to identify a target molecule. For example, a cDNA library can be prepared using mRNA from primary pancreas cells which can be cloned into an expression vector. Cells expressing a cDNA encoding the target molecule then can be selected using the pancreas homing peptide as a probe, for example, by panning of cell clones against pancreas homing peptide attached to a plate. Alternatively, phage can be used to display the pancreas homing peptide and can be attached to magnetic beads coated, for example, with anti-M13 antibodies (Pharmacia). Cells expressing the target molecule that bind to the pancreas homing peptide then can be recovered and the plasmids encoding the receptor can be isolated. The recovered plasmid preparations can be divided into pools and examined in COS cell transfections. The procedure can be repeated until single plasmids are obtained that enable the COS cells to bind the pancreas homing peptide.

The following examples are intended to illustrate but not limit the present invention.

EXAMPLE I

In Vivo Panning

This example demonstrates methods for preparing a phage display library and screening the library using in vivo panning to identify phage expressing peptides that home to a selected organ or tissue.

A. Preparation of Phage Libraries

Phage display libraries were constructed using the fuse 5 vector as described by Koivunen et al., supra, 1995; see, also, Koivunen et al., supra, 1994b). Libraries encoding peptides designated $CX_6C$ (SEQ ID NO: 26), $CX_7C$ (SEQ ID NO: 24), $CX_{10}C$ (SEQ ID NO: 30)) $CX_3CX_3CX_3C$ (SEQ ID NO: 25), $X_2CX_4CX$ (SEQ ID NO: 23), and $X_7$ (SEQ ID NO: 29), were prepared, where "C" indicates cysteine and "$X_N$" indicates the given number of individually selected amino acids. These libraries can display cyclic peptides when at least two cysteine residues are present in the peptide.

The libraries containing the defined cysteine residues were generated using oligonucleotides constructed such that "C" was encoded by the codon TGT and "$X_N$" was encoded by NNK, where "N" is equal molar mixtures of A, C, G and T, and where "K" is equal molar mixtures of G and T. Thus, the peptide represented by $CX_6C$ (SEQ ID NO: 26) can be represented by an oligonucleotide having the sequence TGT $(NNK)_6TGT$ (SEQ ID NO: 31). Oligonucleotides were made double stranded by 3 cycles of PCR amplification, purified and ligated to the nucleic acid encoding the gene III protein in the fuse 5 vector such that, upon expression, the peptide is present as a fusion protein at the N-terminus of the gene III protein.

The vectors were transfected by electroporation into MC1061 cells. Bacteria were cultured for 24 hr in the presence of 20 μg/ml tetracycline, then phage were collected from the supernatant by precipitation twice using polyethylene glycol. Each library contained about $10^{12}$ transducing units/ml (TU; individual recombinant phage).

B. In Vivo Panning of Phage

For lung and pancreas, a mixture of phage libraries containing $10^{10}$ TU was diluted in 200 μl DMEM and injected into the tail vein of anesthetized BALB/c mice (2 month old; Harlan Sprague Dawley; San Diego Calif.); AVERTIN (0.017 ml/g) was used as anesthetic (Pasqualini and Ruoslahti, supra, 1996). After 1–4 minutes, mice were snap frozen in liquid nitrogen or, after about 5 minutes of phage circulation, the mice were perfused through the heart with 5–10 ml of DMEM (Sigma; St. Louis Mo.). To recover the phage, the organs from the perfused mice or partially thawed organs from snap frozen mice were collected and weighed, then were homogenized in 1 ml DMEM-PI (DMEM containing protease inhibitors (PI); phenylmethyl sulfonyl fluoride (PMSF; 1 mM), aprotinin (20 μg/ml), leupeptin (1 μg/ml)).

Organ samples were washed 3 times with ice cold DMEM-PI containing 1% bovine serum albumin (BSA), then directly incubated with 1 ml K91-kan bacteria for 1 hr. Ten ml NZY medium containing 0.2 μg/ml tetracycline (NZY/tet) was added to the bacterial culture, the mixture was incubated in a 37° C. shaker for 1 hr, then 200 μl aliquots were plated in agar plates containing 40 μg/ml tetracycline (tet/agar).

For in vivo panning of skin, two month old BALB/c nude mice were used to avoid contamination by hair. The mice were injected intravenously with phage as described above and, after perfusion through the heart, the skin was removed in large sections and placed on an ice cold plate with the hypodermis facing up. The skin was scraped with a scalpel to remove mostly hypodermis, which was then processed for phage recovery as described below.

For in vivo panning of retina, two month old female Simonson Albino rats were used to provide larger tissue samples than mice. The rats were anesthetized with phenobarbital (50 mg/kg body weight), and, while under deep anesthesia, the abdominal cavity of the rats was opened and $10^{10}$ TU of a phage library was injected into the left ventricle of the heart through the diaphragm. After 2–5 minutes of phage circulation, the eyes were removed, then washed once in 70% EtOH and once in PBS. The anterior chamber, with cornea and lens, was removed and the retina was peeled from the remaining posterior chamber. The tissue was weighed, homogenized with a syringe bulb in 1 ml of ice cold DMEM containing protease inhibitors (1 mM PMSF, 20 μg/ml aprotinin and 1 μg/ml of leupeptin; all from Sigma; St. Louis Mo.). The tissue was washed 3 times with 1 ml of DMEM and the phage were rescued as described below.

Approximately 250 to 300 individual bacterial colonies containing phage recovered from the various organs or tissues were grown for 16 hr in 5 ml NZY/tet. In some experiments, approximately 1000 individual bacteria containing phage were picked and the phage were amplified in 2 ml of NZY/tet or the entire plate containing phage was scraped, pooled and grown in bulk and processed for injection. Where phage were cultured separately, the cultures were pooled and the phage were injected into mice or rats as described above for a second round of in vivo panning. In some experiments, a third or fourth round of panning was performed. Phage DNA was purified from individual bacterial colonies obtained and the DNA sequences encoding the peptides expressed by selected phage were determined (see Koivunen et al., supra, 1994b).

EXAMPLE II

Characterization of Peptides That Home to a Selected Organ

This example demonstrates that an organ or tissue homing peptide of the invention selectively homes to a selected organ or tissue including an organ containing a component of the RES.

A. Lung is the Selected Organ

After two or three rounds of in vivo panning of mice injected with a cyclic $CX_3CX_3CX_3C$ (SEQ ID NO: 25) or a cyclic $CX_6C$ (SEQ ID NO: 26) phage display library, four peptides that homed to lung were identified. The peptide sequences CGFECVRQCPERC (SEQ ID NO: 1; GFE-1) and CGFELETC (SEQ ID NO: 2; GFE-2) appeared repeatedly in the lung and two peptide sequences from the $CX_6C$ (SEQ ID NO: 26) library CTLRDRNC (SEQ ID NO: 15) and CIGEVEVC (SEQ ID NO: 16) also were found to home to lung (see Table 2, below).

To determine the specificity of lung homing of the individual peptides identified, phage displaying the peptides were amplified individually, diluted to the same input titer and administered to mice. Following administration, control kidney and brain organ was removed and the number of TU of phage in lung, kidney and brain was determined. The results shown in FIG. 2 reveal that 10× and 35× more phage having the peptide sequence CGFECVRQCPERC (SEQ ID NO: 1; GFE-1) bound to lung than to kidney and brain, respectively. FIG. 2 also reveals that CGFELETC (SEQ ID NO: 2; GFE-2) was found in lung at a 12× and 20×greater level than in kidney and brain, respectively. The lung homing peptides CGFECVRQCPERC (SEQ ID NO: 1; GFE-1), CGFELETC (SEQ ID NO: 2; GFE-2), CTLRDRNC (SEQ ID NO: 15) and CIGEVEVC (SEQ ID NO: 16) are enriched in lung at 35×, 9×, 6× and 5×, respectively, over unselected phage (see FIG. 2). Thus, substantial enrichment of phage binding to the lung was observed in comparison to control brain and kidney and in comparison to unselected phage.

Figure 3A:
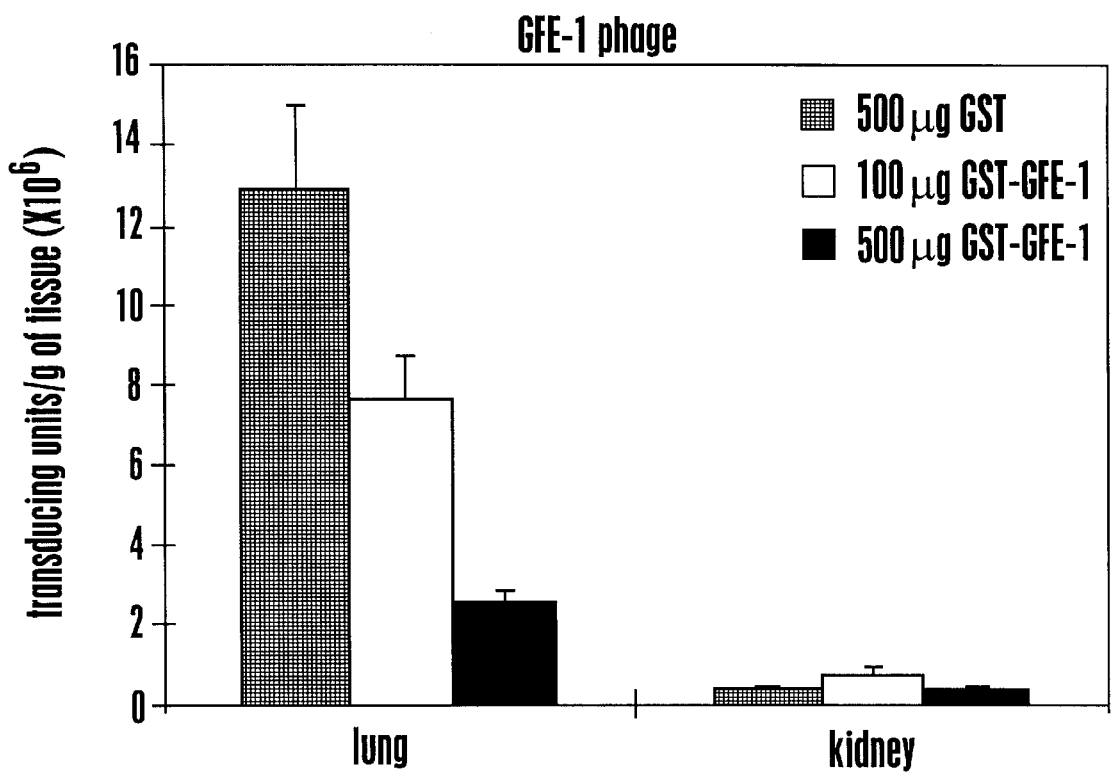
FIGS. 3A and 3B show the effect of coadministration of GST-fusion proteins on the homing of phage displaying lung or skin homing peptides.
Figure 3B:
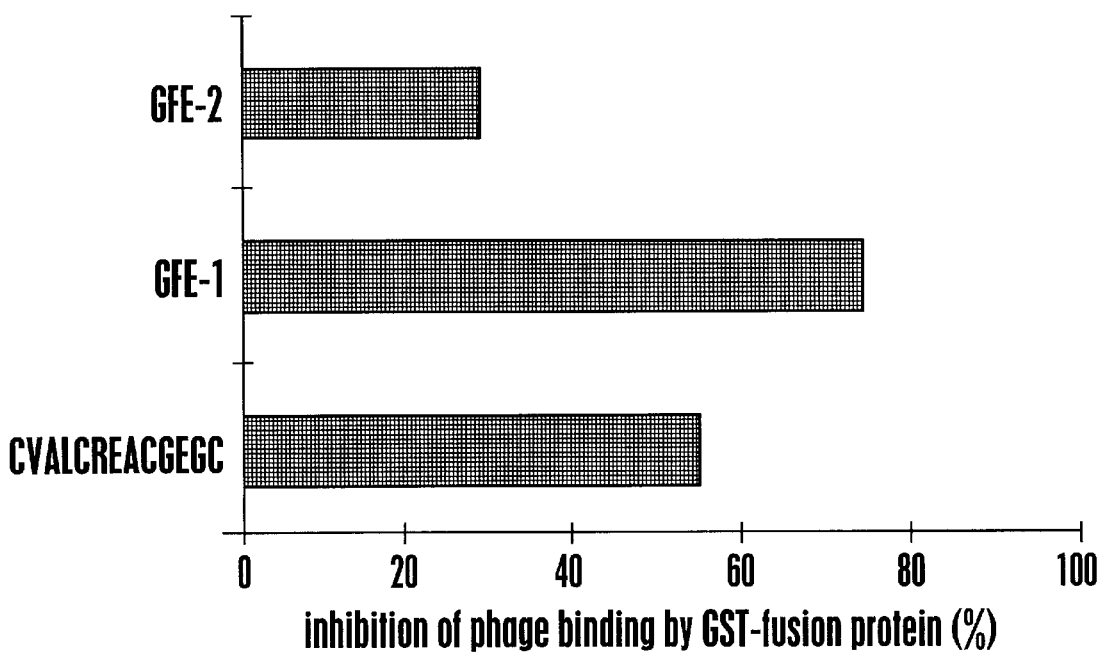

Specificity for the lung homing peptides was also determined by competition experiments with GST-fusion peptides. A GST-GFE-1 (SEQ ID NO: 1) fusion peptide coadministered with GFE-1 (SEQ ID NO: 1) inhibited GFE-1 (SEQ ID NO: 1) homing to the lung, whereas GST had no effect on homing (FIG. 3A). In addition, the inhibitory effect of the GST-GFE-1 (SEQ ID NO: 1) on homing was dose dependent; 70% inhibition of homing occurred when injecting 500 μg of the GST-GFE-1 (SEQ ID NO: 1) fusion protein (FIG. 3B). Coinjection of GST-GFE-2 (SEQ ID NO: 2) with GFE-2 (SEQ ID NO: 2) inhibited homing to a lesser extent; 30% inhibition of homing occurred when injecting 500 μg of the GST-GFE-2 (SEQ ID NO: 2) fusion protein (FIG. 3B). Interestingly, the GST-GFE-1 (SEQ ID NO: 1) fusion was more efficient at inhibiting GFE-2 (SEQ ID NO: 2) homing to the lung; 60% inhibition of GFE-2 (SEQ ID NO: 2) homing occurred when injecting 500 μg of the GST-GFE-1 (SEQ ID NO: 1) fusion protein (FIG. 3B). However, no inhibitory effect of GFE-1 (SEQ ID NO: 1) homing was observed when coinjecting GST-GFE-2 (SEQ ID NO: 2). This can be explained by GFE-1 (SEQ ID NO: 1) having a higher affinity for a shared target molecule than GFE-2 (SEQ ID NO: 2).

Additional lung homing peptides were obtained and the amino acid sequences were determined for the inserts (see Table 2). Peptides containing a GFE motif predominated (see Table 1; SEQ ID NOS: 1 and 2). Other peptides that were present more than once in lung are indicated by an asterisk in Table 2 (below), and the remaining peptides were identified one time each.

These results indicate that the selection of the peptides containing the GFE motif represents the selective binding of several independent phage displaying peptides having the GFE sequence and is not an artifact due, for example, to phage amplification. In addition, in some cases, phage that expressed peptides having the same amino acid sequence were encoded by oligonucleotides having different sequences, therefore confirming that homing of a particular phage to a lung is due to the specific peptide expressed on the phage.

These results demonstrate that in vivo panning can be used to screen phage display libraries in order to identify phage expressing peptides that home to lung, which contain a component of the RES.

B. Skin is the Selected Tissue

After two or three rounds of in vivo panning of mice injected with a cyclic $CX_3CX_3CX_3C$ (SEQ ID NO: 25) phage display library, the peptide sequence CVALCREACGEGC (SEQ ID NO: 3), which appeared repeatedly in skin, was identified (Table 1). To determine the specificity of skin homing of the sequence CVALCREACGEGC (SEQ ID NO: 3), phage displaying the peptide was amplified individually, diluted to the same input titer and administered to mice. Following administration, control kidney and brain organ were removed and the number of TU of phage in skin, kidney and brain was determined.

The results revealed that 7× more phage displaying the peptide sequence CVALCREACGEGC (SEQ ID NO: 3) bound to skin than to kidney or brain (see FIG. 2; Table 1). The peptide CVALCREACGEGC (SEQ ID NO: 3) was enriched in skin 7× over unselected phage (FIG. 2). Thus, substantial enrichment of phage binding to the skin was observed in comparison to control brain and kidney and in comparison to unselected phage. Additional skin homing peptides were obtained and the amino acid sequences were determined for the inserts (Table 5, below). Peptides that were identified more than one time during screening are indicated by an asterisk.

Specificity for the skin homing peptides was also determined by competition experiments with GST-fusion peptides. FIG. 3B shows that a GST-CVALCREACGEGC (SEQ ID NO: 3) fusion peptide coadministered with CVAL-CREACGEGC (SEQ ID NO: 3) inhibited homing to the skin, whereas GST had no effect on homing. The inhibitory effect of the GST-GFE-1 on homing was about 55% when injecting 500 μg of the GST-CVALCREACGEGC (SEQ ID NO: 3) fusion protein (FIG. 3B).

These results demonstrate that in vivo panning can be used to screen phage display libraries in order to identify phage expressing peptides that home to skin and that such homing is specific.

C. Pancreas is the Selected Organ

After two or three rounds of in vivo panning of mice injected with a cyclic $CX_7C$ (SEQ ID NO: 24) phage display library, various pancreas homing peptides were identified (Table 3). In particular, the peptide sequence SWCEPG-WCR (SEQ ID NO: 4) appeared repeatedly in the pancreas. To determine the specificity of SWCEPGWCR (SEQ ID NO: 4), a phage displaying the sequence was amplified individually, diluted to the same input titer and administered to mice. Following administration, control brain organ was removed and the number of TU of phage in each pancreas and was determined. The results shown in FIG. 2, reveal that 10× more phage displaying the peptide sequence SWCEPG-WCR (SEQ ID NO: 4) bound to pancreas than to brain and additional experiments revealed up to 20×enrichment in pancreas as compared to brain (Table 1). In addition, SWCEPGWCR (SEQ ID NO: 4) exhibited a 22×enrichment of phage to the pancreas as compared to unselected phage (see FIG. 2). Thus, substantial enrichment of phage binding to the pancreas was observed in comparison to control tissue (brain) and to unselected phage.

These results demonstrate that in vivo panning can be used to identify molecules that selectively home to pancreas. In addition, the results indicate that in vivo panning identifies independent phage encoding the same peptide.

D. Retina is the Selected Tissue Rats injected with a cyclic $CX_7C$ (SEQ ID NO: 24) phage display library were subjected to in vivo panning and, after three rounds, the peptide sequences CSCFRDVCC (SEQ ID NO: 5) and CRDVVS-VIC (SEQ ID NO: 6) were identified in retina. Because of small tissue sample size, the phage isolated could not be accurately quantitated. Thus, the selectivity of phage displaying the peptides was determined by individually amplifying the phage displaying the sequence and administering the phage to rats with a control phage fdAMPLAY88. This fd-ampicillin phage is similar to fd-tetracycline (fuse 5-based) in that it has the same infectivity.

Rats were injected with an equal amount of the CSC-FRDVCC (SEQ ID NO: 5) or CRDVVSVIC (SEQ ID NO: 6) and the fdAMPLAY88 phage. Following administration, homing to retina was evaluated by comparing the number of TU of the selected phage on tetracycline plates and fdAM-PLAY88 on ampicillin plates recovered from retina.

The results revealed that CSCFRDVCC (SEQ ID NO: 5) showed a 3×enrichment and CRDVVSVIC (SEQ ID NO: 6) showed a 2×enrichment in retina compared to control fdAMPLAY88 phage. Thus, substantial enrichment of phage binding to the retina was observed in comparison to control phage.

Additional retina homing peptides were obtained and the amino acid sequences were determined for the inserts (Table 6, below). Peptides that appeared more than one time are indicated. In particular, the RDV tripeptide motif was present in several different sequence contexts, indicating that the nucleic acids encoding the peptides were derived from a number of independent phage.

These results indicate that the selection of the peptides containing the RDV motif represents the selective binding of several independent phage displaying peptides having the RDV sequence and is not an artifact due, for example, to phage amplification. In addition, in some cases, phage that expressed peptides having the same amino acid sequence were encoded by oligonucleotides having different sequences, therefore confirming that homing of a particular phage to retina is due to the specific peptide expressed on the phage.

These results further demonstrate that the in vivo panning method is a generally applicable method for screening a library to identify, for example, phage expressing peptides that home to a selected organ or tissue, including organs and tissues containing a component of the RES. Database searches did not reveal any significant homology of the pancreas, lung, skin or retina homing peptides to known ligands for endothelial cell receptors.

EXAMPLE III Immunohistologic Analysis of Lung, Pancreas and Skin Homing Peptides This example demonstrates the localization of lung, pancreas and skin homing molecules using immunohistologic examination.

Phage displaying homing peptides were detected in lung, pancreas and skin by immunostaining histologic sections obtained 5 min after administration of phage expressing a lung, pancreas or skin homing peptide ("peptide-phage") to a mouse. Following administration of the peptide-phage, mice were handled as described above and various organs, including lung, pancreas and skin, were removed and fixed in Bouin's solution (Sigma). Histologic sections were prepared and reacted with anti-M13 (phage) antibodies (Pharmacia Biotech; see U.S. Pat. No. 5,622,699, supra, 1997; Pasqualini and Ruoslahti, supra, 1996). Visualization of the bound anti-M13 antibody was performed using a second antibody conjugated to peroxidase (Sigma) according to the manufacturer's instructions.

Phage displaying the lung homing peptide, GFE-1 (SEQ ID NO: 1), were administered intravenously to mice and, after 5 minutes of circulation, the lung was isolated and processed as described above. Immunohistochemical staining of the alveolar capillaries was observed and no preference for any anatomical portion was detected. However, staining of bronchiolar walls and some larger blood vessels was absent. Mice injected with unselected phage did not exhibit lung staining, and no staining was observed in pancreas and skin after injection of GFE-1 (SEQ ID NO: 1).

Similar experiments were performed in pancreas using phage displaying the pancreas homing peptide, SWCEPG-WCR (SEQ ID NO: 4). In these experiments, histological samples of the pancreas as well as control organs and tissues including lung and skin were prepared and examined by immunostaining as described above. The results revealed staining in the capillaries and larger blood vessels of the exocrine pancreas whereas little if any staining of the endocrine pancreas was detected. Again, unselected phage did not stain pancreas, nor was any staining observed in lung and skin of mice injected with phage displaying SWCEPGWCR (SEQ ID NO: 4). Interestingly, some staining of blood vessels within the uterus was observed for the SWCEPGWCR (SEQ ID NO: 4) peptide. Moreover, after intravenous injection of phage displaying SWCEPGWCR (SEQ ID NO: 4), the phage was recovered from uterus at a 6×higher level in comparison to unselected phage. Thus, SWCEPGWCR (SEQ ID NO: 4) homes to both pancreas and uterus.

Experiments were performed in skin using phage displaying the skin homing peptide CVALCREACGEGC (SEQ ID NO: 3). In these experiments, histological samples from the skin as well as control organs and tissues including lung and pancreas were prepared and examined by immunostaining as described above. The results revealed staining in blood vessels of the hypodermis whereas little if any staining of the dermis was detected. Again, unselected phage did not stain these blood vessels, and no staining was observed in control the lung and pancreas of mice injected with phage displaying CVALCREACGEGC (SEQ ID NO: 3).

All phage, including unselected phage, caused staining of the liver and spleen. This result is consistent with the capture of phage by a component of the RES which was previously described.

These results demonstrate that lung, pancreas and skin homing peptides selectively home to lung, pancreas and skin, particularly to the vasculature. In addition, these results reveal that organs and tissues can exhibit differences of the staining patterns within particular regions, presumably reflecting the differential expression of a target molecule within the organ or tissue. Immunohistochemical analysis provides a convenient assay for identifying the localization and distribution of phage expressing lung, pancreas and skin homing peptides.

Although the invention has been described with reference to the examples provided above, it should be understood that various modifications can be made without departing from the spirit of the invention. Accordingly, the invention is limited only by the claims.

TABLE 2

PEPTIDES FROM PHAGE RECOVERED FROM LUNG

| | |
|---|---|
| CIKGNVNC (32) | CRHESSSC (33) |
| CLYIDRRC (34) | CYSLGADC (35) |
| CSKLMMTC (349) | CGFELETC* (2) |
| CNSDVDLC (36) | CVGNLSMC* (37) |
| CEKKLLYC (38) | CKGQRDFC* (39) |
| CTFRNASC (40) | CNMGLTRC* (41) |
| CHEGYLTC* (42) | CGTFGARC (43) |
| CIGEVEVC* (16) | CRISAHPC (44) |
| CLRPYLNC* (45) | CSYPKILC (46) |
| CMELSKQC* (47) | CSEPSGTC (48) |
| CGNETLRC (49) | CTLSNRFC (50) |
| CMGSEYWC (51) | CLFSDENC* (52) |
| CAHQHIQC (53) | CKGQGDWC (54) |
| CAQNMLCC (55) | CWRGDRKIC* (56) |
| CLAKENVVC* (13) | CIFREANVC (57) |
| CRTHGYQGC (58) | CERVVGSSC (59) |
| CKTNHMESC (60) | CYEEKSQSC (61) |
| CKDSAMTIC (62) | CTRSTNTGC (63) |
| CMSWDAVSC* (64) | CKWSRLHSC* (65) |
| CMSPQRSDC (66) | CLHSPRSKC (67) |
| CPQDIRRNC (68) | CLYTKEQRC (69) |
| CQTRNFAQC (70) | CTGHLSTDC (71) |
| CQDLNIMQC (72) | TRRTNNPLT (73) |
| CGYIDPNRISQC (74) | CTVNEAYKTRMC* (75) |

TABLE 2-continued

PEPTIDES FROM PHAGE RECOVERED FROM LUNG

| | |
|---|---|
| CRLRSYGTLSLC* (76) | CAGTCATGCNGVC (77) |
| CADYDLALGLMC (78) | CPKARPAPQYKC (79) |
| CSSHQGGFQHGC (80) | CQETRTEGRKKC (81) |
| CRPWHNQAHTEC* (82) | CSFGTHDTEPHC (83) |
| CSEAASRMIGVC* (84) | CWEEHPSIKWWC* (85) |
| CWDADQIEGIKC (86) | CVDSQSMKGLVC (87) |
| CRLQTMGQGQSC (88) | CRPAQRDAGTSC (89) |
| CGGRDRGTYGPC (90) | CGEVASNERIQC (91) |
| CNSKSSAELEKC (92) | CVLNFKNQARDC (93) |
| CRGKPLANFEDC (94) | CEGHSMRGYGLC (95) |
| CRDRGDRMKSLC (96) | CDNTCTYGVDDC (97) |
| CSAHSQEMNVNC (98) | CGAACGVGCRGRC (99) |
| CGFECVRQCPERC* (1) | CLVGCRLSCGGEC (100) |
| CRSGCVEGCGGRC (101) | CIARCGGACGRHC (102) |
| CGGECGWECEVSC (103) | CGVGCPGLCGGAC* (104) |
| CKWLCLLLCAVAC (105) | CSEGCGPVCWPEC (106) |
| CGAACGVGCGGRC (107) | CSGSCRRGCGIDC (108) |
| CGASCALGCRAYC (109) | CDTSCENNCQGPC (110) |
| CSRQCRGACGQPC (111) | CYWWCDGVCALQC (112) |
| CAGGCAVRCGGTC (113) | CGGACGGVCTGGC* (114) |
| CGRPCVGECRMGC (115) | CLVGCEVGCSPAC (116) |
| CPRTCGAACASPC (117) | CRGDCGIGCRRLC (118) |
| CCFTNFDCYLGC (435) | |

Parentheses contain SEQ ID NO:.
*indicates sequences isolated more than once.

TABLE 3

PEPTIDES FROM PHAGE RECOVERED FROM PANCREAS

| | |
|---|---|
| EICQLGSCT (119) | WRCEGFNCQ (120) |
| RKCLRPDCG (121) | SWCEPGWCR* (4) |
| LACFVTGCL (122) | GLCNGATCM* (123) |
| DMCWLIGCG (124) | SGCRTMVCV (125) |
| QRCPRSFCL (126) | LSCAPVICG (127) |
| RECTNEICY (128) | NECLMISCR (129) |
| SCVFCDWLS (130) | WACEELSCF (131) |
| QNCPVTRCV (132) | CATLTNDEC (133) |
| CDNREMSC (134) | CFMDHSNC (135) |
| CGEYGREC (136) | CHMKRDRTC (137) |
| CKKRLLNVC (138) | CLDYHPKC (139) |
| CMTGRVTC (140) | CNKIVRRC (141) |
| CPDLLVAC (142) | CSDTQSIGC (143) |
| CSKAYDLAC (144) | CSKKGPSYC (145) |
| CTLKHTAMC (146) | CTQHIANC (147) |
| CTTEIDYC (148) | CVGRSGELC (149) |

Parentheses contain SEQ ID NO:.
*indicates sequences isolated more than once.

TABLE 4

PEPTIDES FROM PHAGE RECOVERED FROM GUT

| | |
|---|---|
| YAGFFLV* (150) | RSGARSS (151) |
| CVESTVA (152) | SRRQPLS* (153) |
| SKVWLLL (154) | QVRRVPE (155) |
| YSGKWGW* (156) | MVQSVG (157) |
| LRAVGRA (158) | MSPQLAT* (159) |
| GAVLPGE (160) | WIEEAER* (161) |
| LVSEQLR (162) | RGDRPPY (163) |
| VRRGSPQ (164) | RVRGPER (165) |
| GISAVLS* (166) | GGRGSWE (167) |
| GVSASDW (168) | FRVRGSP (169) |
| SRLSGGT (170) | WELVARS (171) |
| MRRDEQR (172) | GCRCWA (173) |
| LSPPYMW (7) | LCTAMTE (18) |

Parentheses contain SEQ ID NO:.
*indicates sequences isolated more than once.

TABLE 5

PEPTIDES FROM PHAGE RECOVERED FROM SKIN

| | |
|---|---|
| CYADCEGTCGMVC (174) | CWNICPGGCRALC* (175) |
| GPGCEEECQPAC (176) | CKGTCVLGCSEEC* (177) |
| CSTLCGLRCMGTC (178) | CMPRCGVNCKWAC (179) |
| CVGACDLKCTGGC (180) | CVALCREACGEGC* (3) |
| CSSGCSKNCLEMC* (181) | CGRPCRGGCAASC (182) |
| CQGGCGVSCPIFC (183) | CAVRCDGSCVPEC* (184) |
| CGFGCSGSCQMQC (185) | CRVVCADGCRFIC (186) |
| CTMGCTAGCAFAC (187) | CEGKCGLTCECTC (188) |
| CNQGCSGSCDVMC (189) | CASGCSESCYVGC (190) |
| CGGGCQWGCAGEC* (191) | CSVRCKSVCIGLC (192) |
| CPSNCVALCTSGC (193) | CVEGCSSGCGPGC (194) |
| CRVVCADGCRLIC (195) | CSTLCGLRCMGTC (196) |
| CFTFCEYHCQLTC (197) | |

Parentheses contain SEQ ID NO:.
*indicates sequences isolated more than once.

TABLE 6

PEPTIDES FROM PHAGE RECOVERED FROM RETINA

| | |
|---|---|
| CRRIWYAVC (198) | CSAYTTSPC (199) |
| CSCFRDVCC* (5) | CTDKSWPC (200) |
| CTDNRVGS (201) | CTIADFPC (202) |
| CTSDISWWDYKC (203) | CTVDNELC (204) |
| CVGDCIGSCWMFC (205) | CVKFTYDC$^2$ (206) |
| CVSGHLNC (207) | CYGESQQMC (208) |
| CYTGETWTC (209) | CAVSIPRC (210) |
| CDCRGDCFC (211) | CDSLCGGACAARC (212) |
| CERSQSKGVHHC (213) | CFKSTLLC (214) |
| CFWHNRAC (215) | CGDVCPSECPGWC (216) |
| CGEFKVGC* (14) | CGLDCLGDCSGAC (217) |
| CGPGYQAQCSLRC (218) | CGSHCGQLCKSLC (219) |
| CHMGCVSPCAYVC (220) | CILSYDNPC (221) |
| CISRPYFC (222) | CKERLEYTRGVC (223) |
| CKERPSNGLSAC (224) | CKPFRTEC (225) |
| CKSGCGVACRHMC (226) | CLKPGGQEC (227) |
| CMDSQSSC* (228) | CMNILSGC (229) |
| CNIPVTTPIFGC (230) | CNQRTNRESGNC* (231) |
| CNRKNSNEQRAC (232) | CNRMEMPC (233) |
| CQIRPIDKC (234) | CAIDIGGAC (235) |
| CGRFDTAPQRGC (236) | CKRANRLSC (237) |
| CLLNYTYC* (238) | CLNGLVSMC (239) |
| CMSLGNNC (240) | CNRNRMTPC (241) |
| CQASASDHC* (242) | CQLINSSPC (243) |
| CQRVNSVENASC (244) | CRKEHYPC (245) |
| CRRHMERC (246) | CSGRPFKYC (247) |
| CTHLVTLC (248) | CTSSPAYNC (249) |
| CVTSNLRVC* (250) | CWDSGSHIC (251) |
| CERSHGRLC$^1$ (252) | CGNLLTRRC (253) |
| CINCLSQC (254) | CLRHDFYVC (255) |
| CNSRSENC (256) | CRYKGPSC (257) |
| CSHHDTNC (258) | CSRWYTTC (259) |
| CYAGSPLC (260) | CQTTSWNC* (261) |
| CQWSMNVC (262) | CRARIRAEDISC* (263) |
| CRDVVSVIC (6) | CRREYSAC (264) |

Blast-Search:
$^1$rat retinal guanylcyclase precursor EC4.6.1.2
$^2$rat glutamate receptor subunit epsilon 1 precursor No stainings for any motif tested, only evidence for preferential homing are the RDV-containig phages in comparison to an ampicillin-phage.
Parentheses contain SEQ ID NO:.
*indicates sequences isolated more than once.

TABLE 7

PEPTIDES FROM PHAGE RECOVERED FROM PROSTATE

| | |
|---|---|
| EVQSAKW (265) | KRVYVLG (266) |
| GRLSVQV (267) | WKPASLS (268) |
| FAVRVVG (269) | LVRPLEG (270) |
| GFYRMLG (271) | EGRPMVY (272) |
| GSRSLGA (273) | RVWQGDV (274) |

TABLE 7-continued

PEPTIDES FROM PHAGE RECOVERED FROM PROSTATE

| | |
|---|---|
| GDELLA (275) | FVWLVGS (276) |
| GSEPMFR (277) | VSFLEYR (22) |
| WHQPL (278) | SMSIARL* (21) |
| RGRWLAL* (279) | QVEEFPC (280) |
| LWLSGNW (281) | GPMLSVM (282) |
| WTFLERL (283) | VLPGGQW (284) |
| REVKES (285) | RTPAAVM (286) |
| GEWLGEC (287) | PNPLMPL (288) |
| SLWYLGA (289) | YVGGWEL (290) |

Parentheses contain SEQ ID NO:.
*indicates sequences isolated more than once.

TABLE 8

PEPTIDES FROM PHAGE RECOVERED FROM OVARY

| | |
|---|---|
| EVRSRLS* (10) | RVGLVAR* (11) |
| AVKDYFR (291) | GVRTSIW (292) |
| RPVGMRK (293) | RVRLVNL (294) |
| FFAAVRS (295) | KLVNSSW (296) |
| LCERVWR (297) | FGSQAFV (298) |
| WLERPEY (299) | GGDVMWR (300) |
| VRARLMS (301) | TLRESGP (302) |

Parentheses contain SEQ ID NO:.
*indicates sequences isolated more than once.

TABLE 9

PEPTIDES FROM PHAGE RECOVERED FROM LYMPH NODE

| | |
|---|---|
| WGCKLRFCS (303) | MECIKYSCL (304) |
| GICATVKCS (305) | PRCQLWACT (306) |
| TTCMSQLCL (307) | SHCPMASLC (308) |
| GCVRRLLCN (309) | TSCRLFSCA (310) |
| KYCTPVECL (311) | RGCNGSRCS (312) |
| MCPQRNCL (313) | PECEGVSCI (314) |
| AGCSVTVCG* (315) | IPCYWESCR (316) |
| GSCSMFPCS* (317) | QDCVKRPCV (318) |
| SECAYRACS* (319) | WSCARPLCG* (320) |
| SLCGSDGCR (321) | RLCPSSPCT (322) |
| MRCQFSGCT (323) | RYCYPDGCL (324) |
| STCGNWTCR (325) | LPCTGASCP (326) |
| CSCTGQLCR (327) | LECRRWRCD (328) |
| GLCQIDECR* (329) | TACKVAACH (330) |
| DRCLDIWCL* (331) | XXXQGSPCL (332) |
| PLCMATRCA* (333) | RDCSHRSCE* (334) |
| NPCLRAACI* (335) | PTCAYGWCA* (336) |
| LECVANLCT* (337) | RKCGEEVCT* (338) |
| EPCTWNACL* (339) | LVCPGTACV (340) |
| LYCLDASCL (341) | ERCPMAKCY (342) |
| LVCQGSPCL (343) | QQCQDPYCL* (344) |
| DXCXDIWCL (345) | QPCRSMVCA (346) |
| KTCVGVRV (347) | WSCHEFNCR (348) |
| LTCWDWSCR (350) | SLCRLSTCS (351) |
| KTCAGSSCI (352) | VICTGRQCG (353) |
| NPCFGLLV (354) | SLCTAFNCH (355) |
| RTCTPSRCM (356) | QSCLWRICI (357) |
| QYCWSKGCR (358) | LGCFPSWCG (359) |
| VTCSSEWCL (360) | RLCSWGGCA (361) |
| STCISVHCS (362) | EVCLVLSCQ (363) |
| IACDGYLCG (364) | RDCVKNLCR (365) |
| XGCYQKRCT (366) | LGCFXSWCG (367) |
| IRCWGGRCS (368) | IPCSLLGCA (369) |
| AGCVQSQCY (370) | PRCWERVCS (371) |
| KACFGADCX (372) | TLCPLVACE (373) |
| SACWLSNCA (374) | SECYTGSCP (375) |
| GLCQEHRCW (376) | VECGFSAVF (377) |
| EDCREWGCR (378) | HWCRLLACR (379) |

Parentheses contain SEQ ID NO:.
*indicates sequences isolated more than once.
X = Not known.

TABLE 10

PEPTIDES FROM PHAGE RECOVERED FROM ADRENAL GLAND

| | |
|---|---|
| HKGQVYS (380) | FSDVHFW* (381) |
| RGIFVSS (382) | PKVKLSE (383) |
| LRFWQES (384) | IWTVVGQ (385) |
| DKVGLSV (386) | SETWRQF (387) |
| LDGMIVK (388) | RYPLAGG (389) |
| FTDGEDK (390) | RSTEHMS (391) |
| SGRRHEL (392) | LMLPRAD* (27) |
| SSSRVRS (393) | YHRSVGR (394) |
| PLLRPPH (395) | SDKLGFV* (396) |
| LPRYLLS (28) | AGSRTNR (397) |
| ITQLHKT (398) | ARCLVYR (399) |
| GYVAVMT* (400) | GLQVKWV (401) |
| IFTPGWL (402) | KQTSRFL (403) |
| R (Y/F) LLAGG (404) | |

Parentheses contain SEQ ID NO:.
*indicates sequences isolated more than once.

TABLE 11

PEPTIDES FROM PHAGE RECOVERED FROM LIVER

| | |
|---|---|
| ARRGWTL (405) | SRRFVGG* (406) |
| QLTGGCL (407) | ALERRSL (408) |
| KAYFRWR (409) | RWLAWTV (410) |
| VGSFIYS* (411) | LSLLGIA (412) |
| LSTVLWF (413) | SLAMRDS (414) |
| GRSSLAC (415) | SELLGDA (416) |
| CGGAGAR (417) | WRQNMPL* (418) |
| DFLRCRV (419) | QAGLRCH (420) |
| RALYDAL (421) | WVSVLGF (422) |
| GMAVSSW (423) | SWFFLVA (424) |
| WQSVVRV (425) | VKSVCRT* (12) |
| CGNGHSC (426) | AEMEGRD (427) |
| SLRPDNG (428) | PAMGLIR (429) |

Parentheses contain SEQ ID NO:.
*indicates sequences isolated more than once.

---

We claim:

1. An isolated peptide, comprising the sequence SMSIARL (SEQ ID NO:21), wherein said peptide selectively homes to the vasculature of the prostate.

2. The isolated peptide of claim 1, which has at most 100 residues.

3. The isolated peptide of claim 1, which has at most 50 residues.

4. The isolated peptide of claim 3, which has 20 to 50 residues.

5. The isolated peptide of claim 3, which has 7 to 13 residues.

6. The isolated peptide of claim 1, which is cyclic.

7. An isolated peptidomimetic, comprising the sequence SMSIARL (SEQ ID NO:21),
wherein said peptidomimetic selectively homes to the vasculature of the prostate.

8. The isolated peptide of claim 1, consisting of the sequence SMSIARL (SEQ ID NO:21).

9. A method of identifying prostate tissue, comprising the steps of:
a) contacting a tissue or organ with the isolated peptide of claim 1; and
b) detecting binding of said peptide to said organ or tissue, thereby identifying the organ or tissue as prostate tissue.

10. A method of identifying a target molecule expressed by prostate, comprising the method of claim 9, further comprising the steps of:
c) obtaining a sample of said prostate; and
d) identifying the target molecule, which is bound by said peptide.

11. A conjugate, comprising a peptide comprising the sequence SMSIARL (SEQ ID NO: 21),
wherein said peptide is linked to a moiety and said peptide selectively homes to the vasculature of the prostate.

12. The conjugate of claim 11, wherein said moiety is a therapeutic agent.

13. The conjugate of claim 11, wherein said moiety is a detectable agent.

14. The conjugate of claim 11, wherein said peptide has at most 50 residues.

15. The conjugate of claim 14, wherein said peptide has 7 to 13 residues.

16. The conjugate of claim 11, wherein said peptide is cyclic.

17. A conjugate, comprising a peptidomimetic comprising the sequence SMSIARL (SEQ ID NO:21),
wherein said peptidomimetic is linked to a moiety and said peptidomimetic selectively homes to the vasculature of the prostate.

18. The conjugate of claim 11, wherein said peptide consists of the sequence SMSIARL (SEQ ID NO:21).

19. A method of treating a prostate pathology in a subject, comprising administering the conjugate of claim 11 to the subject, wherein said peptide selectively homes to prostate, thereby treating the prostate pathology.

20. An isolated peptide, comprising the sequence VSFLEYR (SEQ ID NO: 22) and having at most 100 residues,
wherein said peptide selectively homes to the vasculature of the prostate.

21. The isolated peptide of claim 20, which has at most 50 residues.

22. The isolated peptide of claim 21, which has 20 to 50 residues.

23. The isolated peptide of claim 21, which has 7 to 13 residues.

24. The isolated peptide of claim 20, which is cyclic.

25. An isolated peptidomimetic, comprising the sequence VSFLEYR (SEQ ID NO:22),
wherein said peptidomimetic selectively homes to the vasculature of the prostate.

26. The isolated peptide of claim 20, consisting of the sequence VSFLEYR (SEQ ID NO:22).

27. A method of identifying prostate tissue, comprising the steps of:
a) contacting a tissue or organ with an isolated peptide that selectively homes to the vasculature of the prostate comprising the sequence VSFLEYR (SEQ ID NO:22); and
b) detecting binding of said peptide to said organ or tissue, thereby identifying the organ or tissue as prostate tissue.

28. A method of identifying a target molecule expressed by prostate, comprising the method of claim 27, further comprising the steps of:
c) obtaining a sample of said prostate; and
d) identifying the target molecule, which is bound by said peptide.

29. A conjugate, comprising a peptide comprising the sequence VSFLEYR (SEQ ID NO: 22) and having at most 100 residues,
wherein said peptide is linked to a moiety and said peptide selectively homes to vasculature of the prostate.

30. The conjugate of claim 29, wherein said moiety is a therapeutic agent.

31. The conjugate of claim 29, wherein said moiety is a detectable agent.

32. The conjugate of claim 29, wherein said peptide has at most 50 residues.

33. The conjugate of claim 32, wherein said peptide has 7 to 13 residues.

34. The conjugate of claim 29, wherein said peptide is cyclic.

35. A conjugate, comprising a peptidomimetic comprising the sequence VSFLEYR (SEQ ID NO:22),
wherein said peptidomimetic is linked to a moiety and said peptidomimetic selectively homes to the vasculature of the prostate.

36. The conjugate of claim 29, wherein said peptide consists of the sequence VSFLEYR (SEQ ID NO:22).

37. A method of treating a prostate pathology in a subject, comprising administering to the subject a conjugate comprising a peptide comprising the sequence VSFLEYR (SEQ ID NO:22) linked to a moiety, wherein said peptide selectively homes to prostate, thereby treating the prostate pathology.

38. An isolated peptide, comprising the sequence RGRWLAL (SEQ ID NO: 279),
wherein said peptide selectively homes to the vasculature of the prostate.

39. The isolated peptide of claim 38, which has at most 100 residues.

40. The isolated peptide of claim 38, which has at most 50 residues.

41. The isolated peptide of claim 40, which has 20 to 50 residues.

42. The isolated peptide of claim 40, which has 7 to 13 residues.

43. The isolated peptide of claim 38, which is cyclic.

44. An isolated peptidomimetic, comprising the sequence RGRWLAL (SEQ ID NO:279),
wherein said peptidomimetic selectively homes to the vasculature of the prostate.

45. The isolated peptide of claim 38, consisting of the sequence RGRWLAL (SEQ ID NO:279).

46. A method of identifying prostate tissue, comprising the steps of:
a) contacting a tissue or organ with the isolated peptide of claim 38; and
b) detecting binding of said peptide to said organ or tissue, thereby identifying the organ or tissue as prostate tissue.

47. A method of identifying a target molecule expressed by prostate, comprising the method of claim 46, further comprising the steps of:

c) obtaining a sample of said prostate; and d) identifying the target molecule, which is bound by said peptide.

48. A conjugate, comprising a peptide comprising the sequence RGRWLAL (SEQ ID NO: 279), wherein said peptide is linked to a moiety and said peptide selectively homes to the vasculature of the prostate.

49. The conjugate of claim 48, wherein said moiety is a therapeutic agent.

50. The conjugate of claim 48, wherein said moiety is a detectable agent.

51. The conjugate of claim 48, wherein said peptide has at most 50 residues.

52. The conjugate of claim 51, wherein said peptide has 7 to 13 residues.

53. The conjugate of claim 48, wherein said peptide is cyclic.

54. A conjugate, comprising a peptidomimetic comprising the sequence RGRWLAL (SEQ ID NO: 279), wherein said peptidomimetic is linked to a moiety and said peptidomimetic selectively homes to the vasculature of the prostate.

55. The conjugate of claim 48, wherein said peptide consists of the sequence RGRWLAL (SEQ ID NO: 279).

56. A method of treating a prostate pathology in a subject, comprising administering the conjugate of claim 48 to the subject, wherein said peptide selectively homes to prostate, thereby treating the prostate pathology.

57. An isolated peptide, comprising an amino acid sequence having, 6 to 100 residues, wherein said peptide selectively homes to the vasculature of the prostate.

58. The isolated peptide of claim 57, which has at most 50 residues.

59. The isolated peptide of claim 58, which has 20 to 50 residues.

60. The isolated peptide of claim 58, which has 7 to 13 residues.

61. An isolated peptide that selectively homes to the vasculature of the prostate, provided that said peptide is not an antibody or antigen-binding fragment thereof.

62. The isolated peptide of claim 61, which has at most 50 residues.

63. The isolated peptide of claim 62, which has 20 to 50 residues.

64. The isolated peptide of claim 62, which has 7 to 13 residues.

65. The isolated peptide of claim 57, which is cyclic.

66. The isolated peptide of claim 57, which is a single-chain peptide.

67. A method of identifying prostate tissue, comprising the steps of:

a) contacting a tissue or organ with the isolated peptide of claim 57; and b) detecting binding of said peptide to said organ or tissue, thereby identifying the organ or tissue as prostate tissue.

68. A method of identifying a target molecule expressed by prostate, comprising the method of claim 67, further comprising the steps of:

c) obtaining a sample of said prostate; and d) identifying the target molecule, which is bound by said peptide.

69. A conjugate, comprising the peptide of claim 57 linked to a moiety.

70. The conjugate of claim 69, wherein said moiety is a therapeutic agent.

71. The conjugate of claim 69, wherein said moiety is a detectable agent.

72. The conjugate of claim 69, wherein said peptide has at most 50 residues.

73. The conjugate of claim 72, wherein said peptide has 7 to 13 residues.

74. The conjugate of claim 69, wherein said peptide is cyclic.

75. The conjugate of claim 69, wherein said peptide is a single-chain peptide.

76. A method of treating a prostate pathology in a subject, comprising administering the conjugate of claim 69 to the subject, wherein said peptide selectively homes to prostate, thereby treating the prostate pathology.

77. The isolated peptide of claim 61, which is cyclic.

78. The isolated peptide of claim 61, which is a single-chain peptide.

79. A method of identifying prostate tissue, comprising the steps of:

a) contacting a tissue or organ with the isolated peptide of claim 61; and b) detecting binding of said peptide to said organ or tissue, thereby identifying the organ or tissue as prostate tissue.

80. A method of identifying a target molecule expressed by prostate, comprising the method of claim 79, further comprising the steps of:

c) obtaining a sample of said prostate; and d) identifying the target molecule, which is bound by said peptide.

81. A conjugate, comprising the peptide of claim 61 linked to a moiety.

82. The conjugate of claim 81, wherein said moiety is a therapeutic agent.

83. The conjugate of claim 81, wherein said moiety is a detectable agent.

84. The conjugate of claim 81, wherein said peptide has at most 50 residues.

85. The conjugate of claim 84, wherein said peptide has 7 to 13 residues.

86. The conjugate of claim 81, wherein said peptide is cyclic.

87. The conjugate of claim 81, wherein said peptide is a single-chain peptide.

88. A method of treating a prostate pathology in a subject, comprising administering the conjugate of claim 81 to the subject, wherein said peptide selectively homes to prostate, thereby treating the prostate pathology.

89. An isolated single-chain peptide that selectively homes to the vasculature of the prostate.

90. The isolated single-chain peptide of claim 89, which has at most 50 residues.

91. The isolated single-chain peptide of claim 90, which has 20 to 50 residues.

92. The isolated single-chain peptide of claim 91, which has 7 to 13 residues.

93. The isolated peptide of claim 89, which is cyclic.

94. A conjugate, comprising the peptide of claim 89 linked to a moiety.

95. The conjugate of claim 94, wherein said moiety is a therapeutic agent.

96. The conjugate of claim 94, wherein said moiety is a detectable agent.

97. The conjugate of claim 94, wherein said peptide has at most 50 residues.

98. The conjugate of claim 97, wherein said peptide has 7 to 13 residues.

99. The conjugate of claim 89, wherein said peptide is cyclic.

100. The isolated peptidomimetic of claim 97, wherein said peptidomimetic is not an antibody or antigen-binding fragment thereof.

101. The conjugate of claim 17, wherein said peptidomimetic is not an antibody or antigen-binding fragment thereof.

102. The isolated peptidomimetic of claim 25, wherein said peptidomimetic is not an antibody or antigen-binding fragment thereof.

103. The conjugate of claim 35, wherein said peptidomimetic is not an antibody or antigen-binding fragment thereof.

104. The isolated peptidomimetic of claim 44, wherein said peptidomimetic is not an antibody or antigen-binding fragment thereof.

105. The conjugate of claim 54, wherein said peptidomimetic is not an antibody or antigen-binding fragment thereof.

* * * * *

UNITED STATES PATENT AND TRADEMARK OFFICE
CERTIFICATE OF CORRECTION

PATENT NO. : 6,232,287 B1
DATED : May 15, 2001
INVENTOR(S) : Ruoslahti et al.

It is certified that error appears in the above-identified patent and that said Letters Patent is hereby corrected as shown below:

Column 1,
Line 5, after "Health" please insert -- and grant number DAMD17-98-1-8562 awarded by the Army --.

Column 2,
Line 38, please delete "-detecting" and replace with -- detecting --.

Column 16,
Line 56, please delete "IIIV-1" and replace with -- HIV-1 --.

Column 26,
Line 28, please delete "means diagnose" and replace with -- means to diagnose --.

Column 33,
Line 32, please delete "20xenrichment" and replace with -- 20x enrichment --.
Line 34, please delete "22xenrichment" and replace with -- 22x enrichment --.
Line 44, please insert -- a carriage return -- after "Tissue".
Line 63, please delete "3xenrichment" and replace with -- 3x enrichment --.
Line 64, please delete "2xenrichment" and replace with -- 2x enrichment --.

Column 34,
Line 27, please insert a carriage return after III.

Column 35,
Line 21, please delete "the lung" and replace with -- lung --.

UNITED STATES PATENT AND TRADEMARK OFFICE
CERTIFICATE OF CORRECTION

PATENT NO. : 6,232,287 B1
DATED : May 15, 2001
INVENTOR(S) : Ruoslahti et al.

It is certified that error appears in the above-identified patent and that said Letters Patent is hereby corrected as shown below:

Column 38,
Line 23, second column of TABLE 9, please delete "WSCHEFNCR" and replace with -- WSCHEFMCR --.

Signed and Sealed this

Sixteenth Day of April, 2002

Attest:

JAMES E. ROGAN
Attesting Officer  Director of the United States Patent and Trademark Office

SEQUENCE LISTING

```
<160> NUMBER OF SEQ ID NOS: 436

<210> SEQ ID NO: 1
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 1

Cys Gly Phe Glu Cys Val Arg Gln Cys Pro Glu Arg Cys
 1               5                  10

<210> SEQ ID NO: 2
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 2

Cys Gly Phe Glu Leu Glu Thr Cys
 1               5

<210> SEQ ID NO: 3
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 3

Cys Val Ala Leu Cys Arg Glu Ala Cys Gly Glu Gly Cys
 1               5                  10
```

```
<210> SEQ ID NO: 4
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 4

Ser Trp Cys Glu Pro Gly Trp Cys Arg
  1               5

<210> SEQ ID NO: 5
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 5

Cys Ser Cys Phe Arg Asp Val Cys Cys
  1               5

<210> SEQ ID NO: 6
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 6

Cys Arg Asp Val Val Ser Val Ile Cys
  1               5

<210> SEQ ID NO: 7
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 7

Leu Ser Pro Pro Tyr Met Trp
  1               5

<210> SEQ ID NO: 8
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 8

Gly Ile Gly Glu Val Glu Val Cys
  1               5

<210> SEQ ID NO: 9
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 9

Tyr Ser Gly Lys Trp Gly Lys
  1               5
```

```
<210> SEQ ID NO: 10
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 10

Glu Val Arg Ser Arg Leu Ser
  1               5

<210> SEQ ID NO: 11
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 11

Arg Val Gly Leu Val Ala Arg
  1               5

<210> SEQ ID NO: 12
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 12

Val Lys Ser Val Cys Arg Thr
  1               5

<210> SEQ ID NO: 13
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 13

Cys Leu Ala Lys Glu Asn Val Val Cys
  1               5

<210> SEQ ID NO: 14
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 14

Cys Gly Glu Phe Lys Val Gly Cys
  1               5

<210> SEQ ID NO: 15
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 15

Cys Thr Leu Arg Asp Arg Asn Cys
  1               5

<210> SEQ ID NO: 16
```

```
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 16

Cys Ile Gly Glu Val Glu Val Cys
 1               5

<210> SEQ ID NO: 17
<211> LENGTH: 23
<212> TYPE: PRT
<213> ORGANISM: Artificial Sequence
<220> FEATURE:
<221> NAME/KEY: SITE
<222> LOCATION: (1)..(10)
<223> OTHER INFORMATION: Xaa may be present or absent
<220> FEATURE:
<221> NAME/KEY: SITE
<222> LOCATION: (14)..(23)
<223> OTHER INFORMATION: Xaa may be present or absent.
<220> FEATURE:
<223> OTHER INFORMATION: Description of Artificial Sequence: Synthetic

<400> SEQUENCE: 17

Xaa Xaa Xaa Xaa Xaa Xaa Xaa Xaa Xaa Xaa Gly Phe Glu Xaa Xaa Xaa
 1               5                  10                  15

Xaa Xaa Xaa Xaa Xaa Xaa Xaa
            20

<210> SEQ ID NO: 18
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 18

Leu Cys Thr Ala Met Thr Glu
 1               5

<210> SEQ ID NO: 19
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 19

Gly Ile Ser Ala Leu Val Leu Ser
 1               5

<210> SEQ ID NO: 20
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 20

Cys Gly Lys Arg Tyr Arg Asn Cys
 1               5

<210> SEQ ID NO: 21
<211> LENGTH: 7
<212> TYPE: PRT
<213> ORGANISM: Artificial Sequence
```

```
<220> FEATURE:
<223> OTHER INFORMATION: Description of Artificial Sequence: Synthetic

<400> SEQUENCE: 21

Ser Met Ser Ile Ala Arg Leu
 1               5

<210> SEQ ID NO: 22
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 22

Val Ser Phe Leu Glu Tyr Arg
 1               5

<210> SEQ ID NO: 23
<211> LENGTH: 9
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: UNSURE
<222> LOCATION: (1)..(2)
<223> OTHER INFORMATION: Unsure
<220> FEATURE:
<221> NAME/KEY: UNSURE
<222> LOCATION: (4)..(7)
<223> OTHER INFORMATION: Unsure
<220> FEATURE:
<221> NAME/KEY: UNSURE
<222> LOCATION: (8)
<223> OTHER INFORMATION: Unsure

<400> SEQUENCE: 23

Xaa Xaa Cys Xaa Xaa Xaa Xaa Cys Xaa
 1               5

<210> SEQ ID NO: 24
<211> LENGTH: 9
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: UNSURE
<222> LOCATION: (2)..(8)
<223> OTHER INFORMATION: Unsure

<400> SEQUENCE: 24

Cys Xaa Xaa Xaa Xaa Xaa Xaa Xaa Cys
 1               5

<210> SEQ ID NO: 25
<211> LENGTH: 13
<212> TYPE: PRT
<213> ORGANISM: Artificial Sequence
<220> FEATURE:
<221> NAME/KEY: UNSURE
<222> LOCATION: (2)..(4)
<223> OTHER INFORMATION: Unsure
<220> FEATURE:
<221> NAME/KEY: UNSURE
<222> LOCATION: (6)..(8)
<223> OTHER INFORMATION: Unsure
<220> FEATURE:
<221> NAME/KEY: UNSURE
<222> LOCATION: (10)..(12)
```

<223> OTHER INFORMATION: Unsure
<220> FEATURE:
<223> OTHER INFORMATION: Description of Artificial Sequence: Synthetic

<400> SEQUENCE: 25

Cys Xaa Xaa Xaa Cys Xaa Xaa Xaa Cys Xaa Xaa Xaa Cys
 1               5                  10

<210> SEQ ID NO: 26
<211> LENGTH: 8
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: UNSURE
<222> LOCATION: (2)..(7)
<223> OTHER INFORMATION: Unsure

<400> SEQUENCE: 26

Cys Xaa Xaa Xaa Xaa Xaa Xaa Cys
 1               5

<210> SEQ ID NO: 27
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 27

Leu Met Leu Pro Arg Ala Asp
 1               5

<210> SEQ ID NO: 28
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 28

Leu Pro Arg Tyr Leu Leu Ser
 1               5

<210> SEQ ID NO: 29
<211> LENGTH: 7
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: UNSURE
<222> LOCATION: (1)..(7)
<223> OTHER INFORMATION: individually selected amino acid

<400> SEQUENCE: 29

Xaa Xaa Xaa Xaa Xaa Xaa Xaa
 1               5

<210> SEQ ID NO: 30
<211> LENGTH: 12
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: UNSURE
<222> LOCATION: (2)..(11)

```
<400> SEQUENCE: 30

Cys Xaa Xaa Xaa Xaa Xaa Xaa Xaa Xaa Xaa Cys
 1               5                  10

<210> SEQ ID NO: 31
<211> LENGTH: 24
<212> TYPE: DNA
<213> ORGANISM: Artificial Sequence
<220> FEATURE:
<221> NAME/KEY: variation
<222> LOCATION: (4)..(21)
<223> OTHER INFORMATION: N is equal molar mixtures of A, C, G and T; K
      is equal molar mixtures of G and T.
<220> FEATURE:
<223> OTHER INFORMATION: Description of Artificial Sequence: Synthetic

<400> SEQUENCE: 31
tgtnnknnkn nknnknnknn ktgt                                         24

<210> SEQ ID NO: 32
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 32

Cys Ile Lys Gly Asn Val Asn Cys
 1               5

<210> SEQ ID NO: 33
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 33

Cys Arg His Glu Ser Ser Ser Cys
 1               5

<210> SEQ ID NO: 34
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 34

Cys Leu Tyr Ile Asp Arg Arg Cys
 1               5

<210> SEQ ID NO: 35
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 35

Cys Tyr Ser Leu Gly Ala Asp Cys
 1               5

<210> SEQ ID NO: 36
<211> LENGTH: 8
<212> TYPE: PRT
```

```
<213> ORGANISM: Artificial Sequence
<220> FEATURE:
<223> OTHER INFORMATION: Description of Artificial Sequence: Synthetic

<400> SEQUENCE: 36

Cys Asn Ser Asp Val Asp Leu Cys
  1               5

<210> SEQ ID NO: 37
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 37

Cys Val Gly Asn Leu Ser Met Cys
  1               5

<210> SEQ ID NO: 38
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 38

Cys Glu Lys Lys Leu Leu Tyr Cys
  1               5

<210> SEQ ID NO: 39
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 39

Cys Lys Gly Gln Arg Asp Phe Cys
  1               5

<210> SEQ ID NO: 40
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 40

Cys Thr Phe Arg Asn Ala Ser Cys
  1               5

<210> SEQ ID NO: 41
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 41

Cys Asn Met Gly Leu Thr Arg Cys
  1               5

<210> SEQ ID NO: 42
<211> LENGTH: 8
<212> TYPE: PRT
<213> ORGANISM: Artificial Sequence
```

```
<220> FEATURE:
<223> OTHER INFORMATION: Description of Artificial Sequence: Synthetic

<400> SEQUENCE: 42

Cys His Glu Gly Tyr Leu Thr Cys
 1               5

<210> SEQ ID NO: 43
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 43

Cys Gly Thr Phe Gly Ala Arg Cys
 1               5

<210> SEQ ID NO: 44
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 44

Cys Arg Ile Ser Ala His Pro Cys
 1               5

<210> SEQ ID NO: 45
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 45

Cys Leu Arg Pro Tyr Leu Asn Cys
 1               5

<210> SEQ ID NO: 46
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 46

Cys Ser Tyr Pro Lys Ile Leu Cys
 1               5

<210> SEQ ID NO: 47
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 47

Cys Met Glu Leu Ser Lys Gln Cys
 1               5

<210> SEQ ID NO: 48
<211> LENGTH: 8
<212> TYPE: PRT
<213> ORGANISM: Artificial Sequence
<220> FEATURE:
```

<223> OTHER INFORMATION: Description of Artificial Sequence: Synthetic

<400> SEQUENCE: 48

Cys Ser Glu Pro Ser Gly Thr Cys
 1               5

<210> SEQ ID NO: 49
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 49

Cys Gly Asn Glu Thr Leu Arg Cys
 1               5

<210> SEQ ID NO: 50
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 50

Cys Thr Leu Ser Asn Arg Phe Cys
 1               5

<210> SEQ ID NO: 51
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 51

Cys Met Gly Ser Glu Tyr Trp Cys
 1               5

<210> SEQ ID NO: 52
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 52

Cys Leu Phe Ser Asp Glu Asn Cys
 1               5

<210> SEQ ID NO: 53
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 53

Cys Ala His Gln His Ile Gln Cys
 1               5

<210> SEQ ID NO: 54
<211> LENGTH: 8
<212> TYPE: PRT
<213> ORGANISM: Artificial Sequence
<220> FEATURE:
<223> OTHER INFORMATION: Description of Artificial Sequence: Synthetic

```
<400> SEQUENCE: 54

Cys Lys Gly Gln Gly Asp Trp Cys
 1               5

<210> SEQ ID NO: 55
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 55

Cys Ala Gln Asn Met Leu Cys Cys
 1               5

<210> SEQ ID NO :56
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 56

Cys Trp Arg Gly Asp Arg Lys Ile Cys
 1               5

<210> SEQ ID NO: 57
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 57

Cys Ile Phe Arg Glu Ala Asn Val Cys
 1               5

<210> SEQ ID NO: 58
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 58

Cys Arg Thr His Gly Tyr Gln Gly Cys
 1               5

<210> SEQ ID NO: 59
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 59

Cys Glu Arg Val Val Gly Ser Ser Cys
 1               5

<210> SEQ ID NO: 60
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 60

Cys Lys Thr Asn His Met Glu Ser Cys
  1               5

<210> SEQ ID NO: 61
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 61

Cys Tyr Glu Glu Lys Ser Gln Ser Cys
  1               5

<210> SEQ ID NO: 62
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 62

Cys Lys Asp Ser Ala Met Thr Ile Cys
  1               5

<210> SEQ ID NO: 63
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 63

Cys Thr Arg Ser Thr Asn Thr Gly Cys
  1               5

<210> SEQ ID NO: 64
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 64

Cys Met Ser Trp Asp Ala Val Ser Cys
  1               5

<210> SEQ ID NO: 65
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 65

Cys Lys Trp Ser Arg Leu His Ser Cys
  1               5

<210> SEQ ID NO: 66
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 66
```

Cys Met Ser Pro Gln Arg Ser Asp Cys
1               5

<210> SEQ ID NO: 67
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 67

Cys Leu His Ser Pro Arg Ser Lys Cys
1               5

<210> SEQ ID NO: 68
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 68

Cys Pro Gln Asp Ile Arg Arg Asn Cys
1               5

<210> SEQ ID NO: 69
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 69

Cys Leu Tyr Thr Lys Glu Gln Arg Cys
1               5

<210> SEQ ID NO: 70
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 70

Cys Gln Thr Arg Asn Phe Ala Gln Cys
1               5

<210> SEQ ID NO: 71
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 71

Cys Thr Gly His Leu Ser Thr Asp Cys
1               5

<210> SEQ ID NO: 72
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 72

```
Cys Gln Asp Leu Asn Ile Met Gln Cys
  1               5
```

<210> SEQ ID NO: 73
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 73

```
Thr Arg Arg Thr Asn Asn Pro Leu Thr
  1               5
```

<210> SEQ ID NO: 74
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 74

```
Cys Gly Tyr Ile Asp Pro Asn Arg Ile Ser Gln Cys
  1               5                  10
```

<210> SEQ ID NO: 75
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 75

```
Cys Thr Val Asn Glu Ala Tyr Lys Thr Arg Met Cys
  1               5                  10
```

<210> SEQ ID NO: 76
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 76

```
Cys Arg Leu Arg Ser Tyr Gly Thr Leu Ser Leu Cys
  1               5                  10
```

<210> SEQ ID NO: 77
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 77

```
Cys Ala Gly Thr Cys Ala Thr Gly Cys Asn Gly Val Cys
  1               5                  10
```

<210> SEQ ID NO: 78
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 78

```
Cys Ala Asp Tyr Asp Leu Ala Leu Gly Leu Met Cys
```

```
<210> SEQ ID NO: 79
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 79

Cys Pro Lys Ala Arg Pro Ala Pro Gln Tyr Lys Cys
 1               5                  10

<210> SEQ ID NO: 80
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 80

Cys Ser Ser His Gln Gly Gly Phe Gln His Gly Cys
 1               5                  10

<210> SEQ ID NO: 81
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 81

Cys Gln Glu Thr Arg Thr Glu Gly Arg Lys Lys Cys
 1               5                  10

<210> SEQ ID NO: 82
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 82

Cys Arg Pro Trp His Asn Gln Ala His Thr Glu Cys
 1               5                  10

<210> SEQ ID NO: 83
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 83

Cys Ser Phe Gly Thr His Asp Thr Glu Pro His Cys
 1               5                  10

<210> SEQ ID NO: 84
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 84

Cys Ser Glu Ala Ala Ser Arg Met Ile Gly Val Cys
 1               5                  10
```

```
<210> SEQ ID NO: 85
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 85

Cys Trp Glu Glu His Pro Ser Ile Lys Trp Trp Cys
 1               5                  10

<210> SEQ ID NO: 86
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 86

Cys Trp Asp Ala Asp Gln Ile Phe Gly Ile Lys Cys
 1               5                  10

<210> SEQ ID NO: 87
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 87

Cys Val Asp Ser Gln Ser Met Lys Gly Leu Val Cys
 1               5                  10

<210> SEQ ID NO: 88
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 88

Cys Arg Leu Gln Thr Met Gly Gln Gly Gln Ser Cys
 1               5                  10

<210> SEQ ID NO: 89
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 89

Cys Arg Pro Ala Gln Arg Asp Ala Gly Thr Ser Cys
 1               5                  10

<210> SEQ ID NO: 90
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 90

Cys Gly Gly Arg Asp Arg Gly Thr Tyr Gly Pro Cys
 1               5                  10
```

```
<210> SEQ ID NO: 91
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 91

Cys Gly Glu Val Ala Ser Asn Glu Arg Ile Gln Cys
 1               5                  10

<210> SEQ ID NO: 92
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 92

Cys Asn Ser Lys Ser Ser Ala Glu Leu Glu Lys Cys
 1               5                  10

<210> SEQ ID NO: 93
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 93

Cys Val Leu Asn Phe Lys Asn Gln Ala Arg Asp Cys
 1               5                  10

<210> SEQ ID NO: 94
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 94

Cys Arg Gly Lys Pro Leu Ala Asn Phe Glu Asp Cys
 1               5                  10

<210> SEQ ID NO: 95
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 95

Cys Glu Gly His Ser Met Arg Gly Tyr Gly Leu Cys
 1               5                  10

<210> SEQ ID NO: 96
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 96

Cys Arg Asp Arg Gly Asp Arg Met Lys Ser Leu Cys
 1               5                  10
```

```
<210> SEQ ID NO: 97
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 97

Cys Asp Asn Thr Cys Thr Tyr Gly Val Asp Asp Cys
 1               5                  10

<210> SEQ ID NO: 98
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 98

Cys Ser Ala His Ser Gln Glu Met Asn Val Asn Cys
 1               5                  10

<210> SEQ ID NO: 99
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 99

Cys Gly Ala Ala Cys Gly Val Gly Cys Arg Gly Arg Cys
 1               5                  10

<210> SEQ ID NO: 100
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 100

Cys Leu Val Gly Cys Arg Leu Ser Cys Gly Gly Glu Cys
 1               5                  10

<210> SEQ ID NO: 101
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 101

Cys Arg Ser Gly Cys Val Glu Gly Cys Gly Gly Arg Cys
 1               5                  10

<210> SEQ ID NO: 102
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 102

Cys Ile Ala Arg Cys Gly Gly Ala Cys Gly Arg His Cys
 1               5                  10

<210> SEQ ID NO: 103
```

```
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 103

Cys Gly Gly Glu Cys Gly Trp Glu Cys Glu Val Ser Cys
 1               5                  10

<210> SEQ ID NO: 104
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 104

Cys Gly Val Gly Cys Pro Gly Leu Cys Gly Gly Ala Cys
 1               5                  10

<210> SEQ ID NO: 105
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 105

Cys Lys Trp Leu Cys Leu Leu Leu Cys Ala Val Ala Cys
 1               5                  10

<210> SEQ ID NO: 106
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 106

Cys Ser Glu Gly Cys Gly Pro Val Cys Trp Pro Glu Cys
 1               5                  10

<210> SEQ ID NO: 107
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 107

Cys Gly Ala Ala Cys Gly Val Gly Cys Gly Gly Arg Cys
 1               5                  10

<210> SEQ ID NO: 108
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 108

Cys Ser Gly Ser Cys Arg Arg Gly Cys Gly Ile Asp Cys
 1               5                  10

<210> SEQ ID NO: 109
<211> LENGTH: 13
```

```
<212> TYPE: PRT
<213> ORGANISM: Artificial Sequence
<220> FEATURE:
<223> OTHER INFORMATION: Description of Artificial Sequence: Synthetic

<400> SEQUENCE: 109

Cys Gly Ala Ser Cys Ala Leu Gly Cys Arg Ala Tyr Cys
 1               5                  10

<210> SEQ ID NO: 110
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 110

Cys Asp Thr Ser Cys Glu Asn Asn Cys Gln Gly Pro Cys
 1               5                  10

<210> SEQ ID NO: 111
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 111

Cys Ser Arg Gln Cys Arg Gly Ala Cys Gly Gln Pro Cys
 1               5                  10

<210> SEQ ID NO: 112
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 112

Cys Tyr Trp Trp Cys Asp Gly Val Cys Ala Leu Gln Cys
 1               5                  10

<210> SEQ ID NO: 113
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 113

Cys Ala Gly Gly Cys Ala Val Arg Cys Gly Gly Thr Cys
 1               5                  10

<210> SEQ ID NO: 114
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 114

Cys Gly Gly Ala Cys Gly Gly Val Cys Thr Gly Gly Cys
 1               5                  10

<210> SEQ ID NO: 115
<211> LENGTH: 13
<212> TYPE: PRT
```

```
<213> ORGANISM: Artificial Sequence
<220> FEATURE:
<223> OTHER INFORMATION: Description of Artificial Sequence: Synthetic

<400> SEQUENCE: 115

Cys Gly Arg Pro Cys Val Gly Glu Cys Arg Met Gly Cys
 1               5                  10

<210> SEQ ID NO: 116
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 116

Cys Leu Val Gly Cys Glu Val Gly Cys Ser Pro Ala Cys
 1               5                  10

<210> SEQ ID NO: 117
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 117

Cys Pro Arg Thr Cys Gly Ala Ala Cys Ala Ser Pro Cys
 1               5                  10

<210> SEQ ID NO: 118
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 118

Cys Arg Gly Asp Cys Gly Ile Gly Cys Arg Arg Leu Cys
 1               5                  10

<210> SEQ ID NO: 119
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 119

Glu Ile Cys Gln Leu Gly Ser Cys Thr
 1               5

<210> SEQ ID NO: 120
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 120

Trp Arg Cys Glu Gly Phe Asn Cys Gln
 1               5

<210> SEQ ID NO: 121
<211> LENGTH: 9
<212> TYPE: PRT
<213> ORGANISM: Artificial Sequence
```

```
<220> FEATURE:
<223> OTHER INFORMATION: Description of Artificial Sequence: Synthetic

<400> SEQUENCE: 121

Arg Lys Cys Leu Arg Pro Asp Cys Gly
 1               5

<210> SEQ ID NO: 122
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 122

Leu Ala Cys Phe Val Thr Gly Cys Leu
 1               5

<210> SEQ ID NO: 123
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 123

Gly Leu Cys Asn Gly Ala Thr Cys Met
 1               5

<210> SEQ ID NO: 124
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 124

Asp Met Cys Trp Leu Ile Gly Cys Gly
 1               5

<210> SEQ ID NO: 125
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 125

Ser Gly Cys Arg Thr Met Val Cys Val
 1               5

<210> SEQ ID NO: 126
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 126

Gln Arg Cys Pro Arg Ser Phe Cys Leu
 1               5

<210> SEQ ID NO: 127
<211> LENGTH: 9
<212> TYPE: PRT
<213> ORGANISM: Artificial Sequence
<220> FEATURE:
```

<223> OTHER INFORMATION: Description of Artificial Sequence: Synthetic

<400> SEQUENCE: 127

Leu Ser Cys Ala Pro Val Ile Cys Gly
 1               5

<210> SEQ ID NO: 128
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 128

Arg Glu Cys Thr Asn Glu Ile Cys Tyr
 1               5

<210> SEQ ID NO: 129
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 129

Asn Glu Cys Leu Met Ile Ser Cys Arg
 1               5

<210> SEQ ID NO: 130
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 130

Ser Cys Val Phe Cys Asp Trp Leu Ser
 1               5

<210> SEQ ID NO: 131
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 131

Trp Ala Cys Glu Glu Leu Ser Cys Phe
 1               5

<210> SEQ ID NO: 132
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 132

Gln Asn Cys Pro Val Thr Arg Cys Val
 1               5

<210> SEQ ID NO: 133
<211> LENGTH: 9
<212> TYPE: PRT
<213> ORGANISM: Artificial Sequence
<220> FEATURE:
<223> OTHER INFORMATION: Description of Artificial Sequence: Synthetic

```
<400> SEQUENCE: 133

Cys Ala Thr Leu Thr Asn Asp Glu Cys
  1               5

<210> SEQ ID NO: 134
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 134

Cys Asp Asn Arg Glu Met Ser Cys
  1               5

<210> SEQ ID NO: 135
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 135

Cys Phe Met Asp His Ser Asn Cys
  1               5

<210> SEQ ID NO: 136
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 136

Cys Gly Glu Tyr Gly Arg Glu Cys
  1               5

<210> SEQ ID NO: 137
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 137

Cys His Met Lys Arg Asp Arg Thr Cys
  1               5

<210> SEQ ID NO: 138
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 138

Cys Lys Lys Arg Leu Leu Asn Val Cys
  1               5

<210> SEQ ID NO: 139
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 139

Cys Leu Asp Tyr His Pro Lys Cys
  1               5

<210> SEQ ID NO: 140
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 140

Cys Met Thr Gly Arg Val Thr Cys
  1               5

<210> SEQ ID NO: 141
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 141

Cys Asn Lys Ile Val Arg Arg Cys
  1               5

<210> SEQ ID NO: 142
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 142

Cys Pro Asp Leu Leu Val Ala Cys
  1               5

<210> SEQ ID NO: 143
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 143

Cys Ser Asp Thr Gln Ser Ile Gly Cys
  1               5

<210> SEQ ID NO: 144
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 144

Cys Ser Lys Ala Tyr Asp Leu Ala Cys
  1               5

<210> SEQ ID NO: 145
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 145
```

Cys Ser Lys Lys Gly Pro Ser Tyr Cys
1               5

<210> SEQ ID NO: 146
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 146

Cys Thr Leu Lys His Thr Ala Met Cys
1               5

<210> SEQ ID NO: 147
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 147

Cys Thr Gln His Ile Ala Asn Cys
1               5

<210> SEQ ID NO: 148
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 148

Cys Thr Thr Glu Ile Asp Tyr Cys
1               5

<210> SEQ ID NO: 149
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 149

Cys Val Gly Arg Ser Gly Glu Leu Cys
1               5

<210> SEQ ID NO: 150
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 150

Tyr Ala Gly Phe Phe Leu Val
1               5

<210> SEQ ID NO: 151
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 151

```
Arg Ser Gly Ala Arg Ser Ser
  1               5

<210> SEQ ID NO: 152
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 152

Cys Val Glu Ser Thr Val Ala
  1               5

<210> SEQ ID NO: 153
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 153

Ser Arg Arg Gln Pro Leu Ser
  1               5

<210> SEQ ID NO: 154
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 154

Ser Lys Val Trp Leu Leu Leu
  1               5

<210> SEQ ID NO: 155
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 155

Gln Val Arg Arg Val Pro Glu
  1               5

<210> SEQ ID NO: 156
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 156

Tyr Ser Gly Lys Trp Gly Trp
  1               5

<210> SEQ ID NO: 157
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 157

Met Val Gln Ser Val Gly
```

<210> SEQ ID NO: 158
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 158

Leu Arg Ala Val Gly Arg Ala
 1               5

<210> SEQ ID NO: 159
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 159

Met Ser Pro Gln Leu Ala Thr
 1               5

<210> SEQ ID NO: 160
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 160

Gly Ala Val Leu Pro Gly Glu
 1               5

<210> SEQ ID NO: 161
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 161

Trp Ile Glu Glu Ala Glu Arg
 1               5

<210> SEQ ID NO: 162
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 162

Leu Val Ser Glu Gln Leu Arg
 1               5

<210> SEQ ID NO: 163
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 163

Arg Gly Asp Arg Pro Pro Tyr
 1               5

```
<210> SEQ ID NO: 164
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 164

Val Arg Arg Gly Ser Pro Gln
 1               5

<210> SEQ ID NO: 165
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 165

Arg Val Arg Gly Pro Glu Arg
 1               5

<210> SEQ ID NO: 166
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 166

Gly Ile Ser Ala Val Leu Ser
 1               5

<210> SEQ ID NO: 167
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 167

Gly Gly Arg Gly Ser Trp Glu
 1               5

<210> SEQ ID NO: 168
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 168

Gly Val Ser Ala Ser Asp Trp
 1               5

<210> SEQ ID NO: 169
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 169

Phe Arg Val Arg Gly Ser Pro
 1               5
```

```
<210> SEQ ID NO: 170
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 170

Ser Arg Leu Ser Gly Gly Thr
 1               5

<210> SEQ ID NO: 171
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 171

Trp Glu Leu Val Ala Arg Ser
 1               5

<210> SEQ ID NO: 172
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 172

Met Arg Arg Asp Glu Gln Arg
 1               5

<210> SEQ ID NO: 173
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 173

Gly Cys Arg Cys Trp Ala
 1               5

<210> SEQ ID NO: 174
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 174

Cys Tyr Ala Asp Cys Glu Gly Thr Cys Gly Met Val Cys
 1               5                  10

<210> SEQ ID NO: 175
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 175

Cys Trp Asn Ile Cys Pro Gly Gly Cys Arg Ala Leu Cys
 1               5                  10
```

<210> SEQ ID NO: 176
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 176

Gly Pro Gly Cys Glu Glu Glu Cys Gln Pro Ala Cys
 1               5                  10

<210> SEQ ID NO: 177
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 177

Cys Lys Gly Thr Cys Val Leu Gly Cys Ser Glu Glu Cys
 1               5                  10

<210> SEQ ID NO: 178
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 178

Cys Ser Thr Leu Cys Gly Leu Arg Cys Met Gly Thr Cys
 1               5                  10

<210> SEQ ID NO: 179
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 179

Cys Met Pro Arg Cys Gly Val Asn Cys Lys Trp Ala Cys
 1               5                  10

<210> SEQ ID NO: 180
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 180

Cys Val Gly Ala Cys Asp Leu Lys Cys Thr Gly Gly Cys
 1               5                  10

<210> SEQ ID NO: 181
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 181

Cys Ser Ser Gly Cys Ser Lys Asn Cys Leu Glu Met Cys
 1               5                  10

<210> SEQ ID NO: 182

```
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 182

Cys Gly Arg Pro Cys Arg Gly Gly Cys Ala Ala Ser Cys
 1               5                  10

<210> SEQ ID NO: 183
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 183

Cys Gln Gly Gly Cys Gly Val Ser Cys Pro Ile Phe Cys
 1               5                  10

<210> SEQ ID NO: 184
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 184

Cys Ala Val Arg Cys Asp Gly Ser Cys Val Pro Glu Cys
 1               5                  10

<210> SEQ ID NO: 185
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 185

Cys Gly Phe Gly Cys Ser Gly Ser Cys Gln Met Gln Cys
 1               5                  10

<210> SEQ ID NO: 186
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 186

Cys Arg Val Val Cys Ala Asp Gly Cys Arg Phe Ile Cys
 1               5                  10

<210> SEQ ID NO: 187
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 187

Cys Thr Met Gly Cys Thr Ala Gly Cys Ala Phe Ala Cys
 1               5                  10

<210> SEQ ID NO: 188
<211> LENGTH: 13
```

```
<212> TYPE: PRT
<213> ORGANISM: Artificial Sequence
<220> FEATURE:
<223> OTHER INFORMATION: Description of Artificial Sequence: Synthetic

<400> SEQUENCE: 188

Cys Glu Gly Lys Cys Gly Leu Thr Cys Glu Cys Thr Cys
 1               5                  10

<210> SEQ ID NO: 189
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 189

Cys Asn Gln Gly Cys Ser Gly Ser Cys Asp Val Met Cys
 1               5                  10

<210> SEQ ID NO: 190
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 190

Cys Ala Ser Gly Cys Ser Glu Ser Cys Tyr Val Gly Cys
 1               5                  10

<210> SEQ ID NO: 191
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 191

Cys Gly Gly Gly Cys Gln Trp Gly Cys Ala Gly Glu Cys
 1               5                  10

<210> SEQ ID NO: 192
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 192

Cys Ser Val Arg Cys Lys Ser Val Cys Ile Gly Leu Cys
 1               5                  10

<210> SEQ ID NO: 193
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 193

Cys Pro Ser Asn Cys Val Ala Leu Cys Thr Ser Gly Cys
 1               5                  10

<210> SEQ ID NO: 194
<211> LENGTH: 13
<212> TYPE: PRT
```

```
<213> ORGANISM: Artificial Sequence
<220> FEATURE:
<223> OTHER INFORMATION: Description of Artificial Sequence: Synthetic

<400> SEQUENCE: 194

Cys Val Glu Gly Cys Ser Ser Gly Cys Gly Pro Gly Cys
 1               5                  10

<210> SEQ ID NO: 195
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 195

Cys Arg Val Val Cys Ala Asp Gly Cys Arg Leu Ile Cys
 1               5                  10

<210> SEQ ID NO: 196
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 196

Gly Ser Thr Leu Cys Gly Leu Arg Cys Met Gly Thr Cys
 1               5                  10

<210> SEQ ID NO: 197
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 197

Cys Phe Thr Phe Cys Glu Tyr His Cys Gln Leu Thr Cys
 1               5                  10

<210> SEQ ID NO: 198
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 198

Cys Arg Arg Ile Trp Tyr Ala Val Cys
 1               5

<210> SEQ ID NO: 199
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 199

Cys Ser Ala Tyr Thr Thr Ser Pro Cys
 1               5

<210> SEQ ID NO: 200
<211> LENGTH: 8
<212> TYPE: PRT
<213> ORGANISM: Artificial Sequence
```

```
<220> FEATURE:
<223> OTHER INFORMATION: Description of Artificial Sequence: Synthetic

<400> SEQUENCE: 200

Cys Thr Asp Lys Ser Trp Pro Cys
 1               5

<210> SEQ ID NO: 201
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 201

Cys Thr Asp Asn Arg Val Gly Ser
 1               5

<210> SEQ ID NO: 202
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 202

Cys Thr Ile Ala Asp Phe Pro Cys
 1               5

<210> SEQ ID NO: 203
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 203

Cys Thr Ser Asp Ile Ser Trp Trp Asp Tyr Lys Cys
 1               5                   10

<210> SEQ ID NO: 204
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 204

Cys Thr Val Asp Asn Glu Leu Cys
 1               5

<210> SEQ ID NO: 205
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 205

Cys Val Gly Asp Cys Ile Gly Ser Cys Trp Met Phe Cys
 1               5                   10

<210> SEQ ID NO: 206
<211> LENGTH: 8
<212> TYPE: PRT
<213> ORGANISM: Artificial Sequence
<220> FEATURE:
```

<223> OTHER INFORMATION: Description of Artificial Sequence: Synthetic

<400> SEQUENCE: 206

Cys Val Lys Phe Thr Tyr Asp Cys
 1               5

<210> SEQ ID NO: 207
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 207

Cys Val Ser Gly His Leu Asn Cys
 1               5

<210> SEQ ID NO: 208
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 208

Cys Tyr Gly Glu Ser Gln Gln Met Cys
 1               5

<210> SEQ ID NO: 209
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 209

Cys Tyr Thr Gly Glu Thr Trp Thr Cys
 1               5

<210> SEQ ID NO: 210
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 210

Cys Ala Val Ser Ile Pro Arg Cys
 1               5

<210> SEQ ID NO: 211
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 211

Cys Asp Cys Arg Gly Asp Cys Phe Cys
 1               5

<210> SEQ ID NO: 212
<211> LENGTH: 13
<212> TYPE: PRT
<213> ORGANISM: Artificial Sequence
<220> FEATURE:
<223> OTHER INFORMATION: Description of Artificial Sequence: Synthetic

```
<400> SEQUENCE: 212

Cys Asp Ser Leu Cys Gly Gly Ala Cys Ala Ala Arg Cys
  1               5                  10

<210> SEQ ID NO: 213
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 213

Cys Glu Arg Ser Gln Ser Lys Gly Val His His Cys
  1               5                  10

<210> SEQ ID NO: 214
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 214

Cys Phe Lys Ser Thr Leu Leu Cys
  1               5

<210> SEQ ID NO: 215
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 215

Cys Phe Trp His Asn Arg Ala Cys
  1               5

<210> SEQ ID NO: 216
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 216

Cys Gly Asp Val Cys Pro Ser Glu Cys Pro Gly Trp Cys
  1               5                  10

<210> SEQ ID NO: 217
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 217

Cys Gly Leu Asp Cys Leu Gly Asp Cys Ser Gly Ala Cys
  1               5                  10

<210> SEQ ID NO: 218
<211> LENGTH: 13
<212> TYPE: PRT
<213> ORGANISM: Artificial Sequence
<220> FEATURE:
<223> OTHER INFORMATION: Description of Artificial Sequence: Synthetic
```

-continued

```
<400> SEQUENCE: 218

Cys Gly Pro Gly Tyr Gln Ala Gln Cys Ser Leu Arg Cys
  1               5                  10

<210> SEQ ID NO: 219
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 219

Cys Gly Ser His Cys Gly Gln Leu Cys Lys Ser Leu Cys
  1               5                  10

<210> SEQ ID NO: 220
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 220

Cys His Met Gly Cys Val Ser Pro Cys Ala Tyr Val Cys
  1               5                  10

<210> SEQ ID NO: 221
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 221

Cys Ile Leu Ser Tyr Asp Asn Pro Cys
  1               5

<210> SEQ ID NO: 222
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 222

Cys Ile Ser Arg Pro Tyr Phe Cys
  1               5

<210> SEQ ID NO: 223
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 223

Cys Lys Glu Arg Leu Glu Tyr Thr Arg Gly Val Cys
  1               5                  10

<210> SEQ ID NO: 224
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 224
```

Cys Lys Glu Arg Pro Ser Asn Gly Leu Ser Ala Cys
 1               5                  10

<210> SEQ ID NO: 225
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 225

Cys Lys Pro Phe Arg Thr Glu Cys
 1               5

<210> SEQ ID NO: 226
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 226

Cys Lys Ser Gly Cys Gly Val Ala Cys Arg His Met Cys
 1               5                  10

<210> SEQ ID NO: 227
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 227

Cys Leu Lys Pro Gly Gly Gln Glu Cys
 1               5

<210> SEQ ID NO: 228
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 228

Cys Met Asp Ser Gln Ser Ser Cys
 1               5

<210> SEQ ID NO: 229
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 229

Cys Met Asn Ile Leu Ser Gly Cys
 1               5

<210> SEQ ID NO: 230
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 230

```
Cys Asn Ile Pro Val Thr Thr Pro Ile Phe Gly Cys
 1               5                  10
```

<210> SEQ ID NO: 231
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 231

```
Cys Asn Gln Arg Thr Asn Arg Glu Ser Gly Asn Cys
 1               5                  10
```

<210> SEQ ID NO: 232
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 232

```
Cys Asn Arg Lys Asn Ser Asn Glu Gln Arg Ala Cys
 1               5                  10
```

<210> SEQ ID NO: 233
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 233

```
Cys Asn Arg Met Glu Met Pro Cys
 1               5
```

<210> SEQ ID NO: 234
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 234

```
Cys Gln Ile Arg Pro Ile Asp Lys Cys
 1               5
```

<210> SEQ ID NO: 235
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 235

```
Cys Ala Ile Asp Ile Gly Gly Ala Cys
 1               5
```

<210> SEQ ID NO: 236
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 236

```
Cys Gly Arg Phe Asp Thr Ala Pro Gln Arg Gly Cys
```

```
              1               5                   10
```

<210> SEQ ID NO: 237
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 237

```
Cys Lys Arg Ala Asn Arg Leu Ser Cys
  1               5
```

<210> SEQ ID NO: 238
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 238

```
Cys Leu Leu Asn Tyr Thr Tyr Cys
  1               5
```

<210> SEQ ID NO: 239
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 239

```
Cys Leu Asn Gly Leu Val Ser Met Cys
  1               5
```

<210> SEQ ID NO: 240
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 240

```
Cys Met Ser Leu Gly Asn Asn Cys
  1               5
```

<210> SEQ ID NO: 241
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 241

```
Cys Asn Arg Asn Arg Met Thr Pro Cys
  1               5
```

<210> SEQ ID NO: 242
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 242

```
Cys Gln Ala Ser Ala Ser Asp His Cys
  1               5
```

```
<210> SEQ ID NO: 243
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 243

Cys Gln Leu Ile Asn Ser Ser Pro Cys
  1               5

<210> SEQ ID NO: 244
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 244

Cys Gln Arg Val Asn Ser Val Glu Asn Ala Ser Cys
  1               5                  10

<210> SEQ ID NO: 245
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 245

Cys Arg Lys Glu His Tyr Pro Cys
  1               5

<210> SEQ ID NO: 246
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 246

Cys Arg Arg His Met Glu Arg Cys
  1               5

<210> SEQ ID NO: 247
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 247

Cys Ser Gly Arg Pro Phe Lys Tyr Cys
  1               5

<210> SEQ ID NO: 248
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 248

Cys Thr His Leu Val Thr Leu Cys
  1               5
```

```
<210> SEQ ID NO: 249
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 249

Cys Thr Ser Ser Pro Ala Tyr Asn Cys
  1               5

<210> SEQ ID NO: 250
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 250

Cys Val Thr Ser Asn Leu Arg Val Cys
  1               5

<210> SEQ ID NO: 251
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 251

Cys Trp Asp Ser Gly Ser His Ile Cys
  1               5

<210> SEQ ID NO: 252
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 252

Cys Glu Arg Ser His Gly Arg Leu Cys
  1               5

<210> SEQ ID NO: 253
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 253

Cys Gly Asn Leu Leu Thr Arg Arg Cys
  1               5

<210> SEQ ID NO: 254
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 254

Cys Ile Asn Cys Leu Ser Gln Cys
  1               5
```

```
<210> SEQ ID NO: 255
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 255

Cys Leu Arg His Asp Phe Tyr Val Cys
  1               5

<210> SEQ ID NO: 256
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 256

Cys Asn Ser Arg Ser Glu Asn Cys
  1               5

<210> SEQ ID NO: 257
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 257

Cys Arg Tyr Lys Gly Pro Ser Cys
  1               5

<210> SEQ ID NO: 258
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 258

Cys Ser His His Asp Thr Asn Cys
  1               5

<210> SEQ ID NO: 259
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 259

Cys Ser Arg Trp Tyr Thr Thr Cys
  1               5

<210> SEQ ID NO: 260
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 260

Cys Tyr Ala Gly Ser Pro Leu Cys
  1               5

<210> SEQ ID NO: 261
```

```
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 261

Cys Gln Thr Thr Ser Trp Asn Cys
  1               5

<210> SEQ ID NO: 262
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 262

Cys Gln Trp Ser Met Asn Val Cys
  1               5

<210> SEQ ID NO: 263
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 263

Cys Arg Ala Arg Ile Arg Ala Glu Asp Ile Ser Cys
  1               5                  10

<210> SEQ ID NO: 264
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 264

Cys Arg Arg Glu Tyr Ser Ala Cys
  1               5

<210> SEQ ID NO: 265
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 265

Glu Val Gln Ser Ala Lys Trp
  1               5

<210> SEQ ID NO: 266
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 266

Lys Arg Val Tyr Val Leu Gly
  1               5

<210> SEQ ID NO: 267
<211> LENGTH: 7
```

```
<212> TYPE: PRT
<213> ORGANISM: Artificial Sequence
<220> FEATURE:
<223> OTHER INFORMATION: Description of Artificial Sequence: Synthetic

<400> SEQUENCE: 267

Gly Arg Leu Ser Val Gln Val
  1               5

<210> SEQ ID NO: 268
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 268

Trp Lys Pro Ala Ser Leu Ser
  1               5

<210> SEQ ID NO: 269
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 269

Phe Ala Val Arg Val Val Gly
  1               5

<210> SEQ ID NO: 270
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 270

Leu Val Arg Pro Leu Glu Gly
  1               5

<210> SEQ ID NO: 271
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 271

Gly Phe Tyr Arg Met Leu Gly
  1               5

<210> SEQ ID NO: 272
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 272

Glu Gly Arg Pro Met Val Tyr
  1               5

<210> SEQ ID NO: 273
<211> LENGTH: 7
<212> TYPE: PRT
```

```
<213> ORGANISM: Artificial Sequence
<220> FEATURE:
<223> OTHER INFORMATION: Description of Artificial Sequence: Synthetic

<400> SEQUENCE: 273

Gly Ser Arg Ser Leu Gly Ala
  1               5

<210> SEQ ID NO: 274
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 274

Arg Val Trp Gln Gly Asp Val
  1               5

<210> SEQ ID NO: 275
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 275

Gly Asp Glu Leu Leu Ala
  1               5

<210> SEQ ID NO: 276
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 276

Phe Val Trp Leu Val Gly Ser
  1               5

<210> SEQ ID NO: 277
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 277

Gly Ser Glu Pro Met Phe Arg
  1               5

<210> SEQ ID NO: 278
<211> LENGTH: 5
<212> TYPE: PRT
<213> ORGANISM: Artificial Sequence
<220> FEATURE:
<223> OTHER INFORMATION: Description of Artificial Sequence: Synthetic

<400> SEQUENCE: 278

Trp His Gln Pro Leu
  1               5

<210> SEQ ID NO: 279
<211> LENGTH: 7
<212> TYPE: PRT
<213> ORGANISM: Artificial Sequence
```

```
<220> FEATURE:
<223> OTHER INFORMATION: Description of Artificial Sequence: Synthetic

<400> SEQUENCE: 279

Arg Gly Arg Trp Leu Ala Leu
 1               5

<210> SEQ ID NO: 280
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 280

Gln Val Glu Glu Phe Pro Cys
 1               5

<210> SEQ ID NO: 281
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 281

Leu Trp Leu Ser Gly Asn Trp
 1               5

<210> SEQ ID NO: 282
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 282

Gly Pro Met Leu Ser Val Met
 1               5

<210> SEQ ID NO: 283
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 283

Trp Thr Phe Leu Glu Arg Leu
 1               5

<210> SEQ ID NO: 284
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 284

Val Leu Pro Gly Gly Gln Trp
 1               5

<210> SEQ ID NO: 285
<211> LENGTH: 6
<212> TYPE: PRT
<213> ORGANISM: Artificial Sequence
<220> FEATURE:
```

<223> OTHER INFORMATION: Description of Artificial Sequence: Synthetic

<400> SEQUENCE: 285

Arg Glu Val Lys Glu Ser
 1               5

<210> SEQ ID NO: 286
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 286

Arg Thr Pro Ala Ala Val Met
 1               5

<210> SEQ ID NO: 287
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 287

Gly Glu Trp Leu Gly Glu Cys
 1               5

<210> SEQ ID NO: 288
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 288

Pro Asn Pro Leu Met Pro Leu
 1               5

<210> SEQ ID NO: 289
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 289

Ser Leu Trp Tyr Leu Gly Ala
 1               5

<210> SEQ ID NO: 290
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 290

Tyr Val Gly Gly Trp Glu Leu
 1               5

<210> SEQ ID NO: 291
<211> LENGTH: 7
<212> TYPE: PRT
<213> ORGANISM: Artificial Sequence
<220> FEATURE:
<223> OTHER INFORMATION: Description of Artificial Sequence: Synthetic

```
<400> SEQUENCE: 291

Ala Val Lys Asp Tyr Phe Arg
 1               5

<210> SEQ ID NO: 292
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 292

Gly Val Arg Thr Ser Ile Trp
 1               5

<210> SEQ ID NO: 293
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 293

Arg Pro Val Gly Met Arg Lys
 1               5

<210> SEQ ID NO: 294
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 294

Arg Val Arg Leu Val Asn Leu
 1               5

<210> SEQ ID NO: 295
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 295

Phe Phe Ala Ala Val Arg Ser
 1               5

<210> SEQ ID NO: 296
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 296

Lys Leu Val Asn Ser Ser Trp
 1               5

<210> SEQ ID NO: 297
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 297

Leu Cys Glu Arg Val Trp Arg
  1               5

<210> SEQ ID NO: 298
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 298

Phe Gly Ser Gln Ala Phe Val
  1               5

<210> SEQ ID NO: 299
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 299

Trp Leu Glu Arg Pro Glu Tyr
  1               5

<210> SEQ ID NO: 300
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 300

Gly Gly Asp Val Met Trp Arg
  1               5

<210> SEQ ID NO: 301
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 301

Val Arg Ala Arg Leu Met Ser
  1               5

<210> SEQ ID NO: 302
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 302

Thr Leu Arg Glu Ser Gly Pro
  1               5

<210> SEQ ID NO: 303
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 303
```

```
Trp Gly Cys Lys Leu Arg Phe Cys Ser
  1               5
```

<210> SEQ ID NO: 304
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 304

```
Met Glu Cys Ile Lys Tyr Ser Cys Leu
  1               5
```

<210> SEQ ID NO: 305
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 305

```
Gly Ile Cys Ala Thr Val Lys Cys Ser
  1               5
```

<210> SEQ ID NO: 306
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 306

```
Pro Arg Cys Gln Leu Trp Ala Cys Thr
  1               5
```

<210> SEQ ID NO: 307
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 307

```
Thr Thr Cys Met Ser Gln Leu Cys Leu
  1               5
```

<210> SEQ ID NO: 308
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 308

```
Ser His Cys Pro Met Ala Ser Leu Cys
  1               5
```

<210> SEQ ID NO: 309
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 309

Gly Cys Val Arg Arg Leu Leu Cys Asn
1               5

<210> SEQ ID NO: 310
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 310

Thr Ser Cys Arg Leu Phe Ser Cys Ala
1               5

<210> SEQ ID NO: 311
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 311

Lys Tyr Cys Thr Pro Val Glu Cys Leu
1               5

<210> SEQ ID NO: 312
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 312

Arg Gly Cys Asn Gly Ser Arg Cys Ser
1               5

<210> SEQ ID NO: 313
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 313

Met Cys Pro Gln Arg Asn Cys Leu
1               5

<210> SEQ ID NO: 314
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 314

Pro Glu Cys Glu Gly Val Ser Cys Ile
1               5

<210> SEQ ID NO: 315
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 315

Ala Gly Cys Ser Val Thr Val Cys Gly

<210> SEQ ID NO: 316
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 316

Ile Pro Cys Tyr Trp Glu Ser Cys Arg
 1               5

<210> SEQ ID NO: 317
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 317

Gly Ser Cys Ser Met Phe Pro Cys Ser
 1               5

<210> SEQ ID NO: 318
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 318

Gln Asp Cys Val Lys Arg Pro Cys Val
 1               5

<210> SEQ ID NO: 319
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 319

Ser Glu Cys Ala Tyr Arg Ala Cys Ser
 1               5

<210> SEQ ID NO: 320
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 320

Trp Ser Cys Ala Arg Pro Leu Cys Gly
 1               5

<210> SEQ ID NO: 321
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 321

Ser Leu Cys Gly Ser Asp Gly Cys Arg
 1               5

```
<210> SEQ ID NO: 322
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 322

Arg Leu Cys Pro Ser Ser Pro Cys Thr
  1               5

<210> SEQ ID NO: 323
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 323

Met Arg Cys Gly Phe Ser Gly Cys Thr
  1               5

<210> SEQ ID NO: 324
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 324

Arg Tyr Cys Tyr Pro Asp Gly Cys Leu
  1               5

<210> SEQ ID NO: 325
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 325

Ser Thr Cys Gly Asn Trp Thr Cys Arg
  1               5

<210> SEQ ID NO: 326
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 326

Leu Pro Cys Thr Gly Ala Ser Cys Pro
  1               5

<210> SEQ ID NO: 327
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 327

Cys Ser Cys Thr Gly Gln Leu Cys Arg
  1               5
```

```
<210> SEQ ID NO: 328
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 328

Leu Glu Cys Arg Arg Trp Arg Cys Asp
 1               5

<210> SEQ ID NO: 329
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 329

Gly Leu Cys Gln Ile Asp Glu Cys Arg
 1               5

<210> SEQ ID NO: 330
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 330

Thr Ala Cys Lys Val Ala Ala Cys His
 1               5

<210> SEQ ID NO: 331
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 331

Asp Arg Cys Leu Asp Ile Trp Cys Leu
 1               5

<210> SEQ ID NO: 332
<211> LENGTH: 9
<212> TYPE: PRT
<213> ORGANISM: Artificial Sequence
<220> FEATURE:
<221> NAME/KEY: UNSURE
<222> LOCATION: (1)..(3)
<223> OTHER INFORMATION: Unsure
<220> FEATURE:
<223> OTHER INFORMATION: Description of Artificial Sequence: Synthetic

<400> SEQUENCE: 332

Xaa Xaa Xaa Gln Gly Ser Pro Cys Leu
 1               5

<210> SEQ ID NO: 333
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 333
```

```
Pro Leu Cys Met Ala Thr Arg Cys Ala
 1               5
```

<210> SEQ ID NO: 334
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 334

```
Arg Asp Cys Ser His Arg Ser Cys Glu
 1               5
```

<210> SEQ ID NO: 335
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 335

```
Asn Pro Cys Leu Arg Ala Ala Cys Ile
 1               5
```

<210> SEQ ID NO: 336
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 336

```
Pro Thr Cys Ala Tyr Gly Trp Cys Ala
 1               5
```

<210> SEQ ID NO: 337
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 337

```
Leu Glu Cys Val Ala Asn Leu Cys Thr
 1               5
```

<210> SEQ ID NO: 338
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 338

```
Arg Lys Cys Gly Glu Glu Val Cys Thr
 1               5
```

<210> SEQ ID NO: 339
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 339

```
Glu Pro Cys Thr Trp Asn Ala Cys Leu
```

<210> SEQ ID NO: 340
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 340

Leu Val Cys Pro Gly Thr Ala Cys Val
 1               5

<210> SEQ ID NO: 341
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 341

Leu Tyr Cys Leu Asp Ala Ser Cys Leu
 1               5

<210> SEQ ID NO: 342
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 342

Glu Arg Cys Pro Met Ala Lys Cys Tyr
 1               5

<210> SEQ ID NO: 343
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 343

Leu Val Cys Gln Gly Ser Pro Cys Leu
 1               5

<210> SEQ ID NO: 344
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 344

Gln Gln Cys Gln Asp Pro Tyr Cys Leu
 1               5

<210> SEQ ID NO: 345
<211> LENGTH: 9
<212> TYPE: PRT
<213> ORGANISM: Artificial Sequence
<220> FEATURE:
<221> NAME/KEY: UNSURE
<222> LOCATION: (2)
<223> OTHER INFORMATION: Unsure
<220> FEATURE:
<221> NAME/KEY: UNSURE
<222> LOCATION: (4)

-continued

```
<223> OTHER INFORMATION: Unsure
<220> FEATURE:
<223> OTHER INFORMATION: Description of Artificial Sequence: Synthetic

<400> SEQUENCE: 345

Asp Xaa Cys Xaa Asp Ile Trp Cys Leu
 1               5

<210> SEQ ID NO: 346
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 346

Gln Pro Cys Arg Ser Met Val Cys Ala
 1               5

<210> SEQ ID NO: 347
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 347

Lys Thr Cys Val Gly Val Arg Val
 1               5

<210> SEQ ID NO: 348
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 348

Trp Ser Cys His Glu Phe Met Cys Arg
 1               5

<210> SEQ ID NO: 349
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 349

Cys Ser Lys Leu Met Met Thr Cys
 1               5

<210> SEQ ID NO: 350
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 350

Leu Thr Cys Trp Asp Trp Ser Cys Arg
 1               5

<210> SEQ ID NO: 351
<211> LENGTH: 9
<212> TYPE: PRT
<213> ORGANISM: Artificial Sequence
```

```
<220> FEATURE:
<223> OTHER INFORMATION: Description of Artificial Sequence: Synthetic

<400> SEQUENCE: 351

Ser Leu Cys Arg Leu Ser Thr Cys Ser
 1               5

<210> SEQ ID NO: 352
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 352

Lys Thr Cys Ala Gly Ser Ser Cys Ile
 1               5

<210> SEQ ID NO: 353
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 353

Val Ile Cys Thr Gly Arg Gln Cys Gly
 1               5

<210> SEQ ID NO: 354
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 354

Asn Pro Cys Phe Gly Leu Leu Val
 1               5

<210> SEQ ID NO: 355
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 355

Ser Leu Cys Thr Ala Phe Asn Cys His
 1               5

<210> SEQ ID NO: 356
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 356

Arg Thr Cys Thr Pro Ser Arg Cys Met
 1               5

<210> SEQ ID NO: 357
<211> LENGTH: 9
<212> TYPE: PRT
<213> ORGANISM: Artificial Sequence
<220> FEATURE:
```

<223> OTHER INFORMATION: Description of Artificial Sequence: Synthetic

<400> SEQUENCE: 357

Gln Ser Cys Leu Trp Arg Ile Cys Ile
 1               5

<210> SEQ ID NO: 358
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 358

Gln Tyr Cys Trp Ser Lys Gly Cys Arg
 1               5

<210> SEQ ID NO: 359
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 359

Leu Gly Cys Phe Pro Ser Trp Cys Gly
 1               5

<210> SEQ ID NO: 360
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 360

Val Thr Cys Ser Ser Glu Trp Cys Leu
 1               5

<210> SEQ ID NO: 361
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 361

Arg Leu Cys Ser Trp Gly Gly Cys Ala
 1               5

<210> SEQ ID NO: 362
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 362

Ser Thr Cys Ile Ser Val His Cys Ser
 1               5

<210> SEQ ID NO: 363
<211> LENGTH: 9
<212> TYPE: PRT
<213> ORGANISM: Artificial Sequence
<220> FEATURE:
<223> OTHER INFORMATION: Description of Artificial Sequence: Synthetic

```
<400> SEQUENCE: 363

Glu Val Cys Leu Val Leu Ser Cys Gln
  1               5

<210> SEQ ID NO: 364
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 364

Ile Ala Cys Asp Gly Tyr Leu Cys Gly
  1               5

<210> SEQ ID NO: 365
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 365

Arg Asp Cys Val Lys Asn Leu Cys Arg
  1               5

<210> SEQ ID NO: 366
<211> LENGTH: 9
<212> TYPE: PRT
<213> ORGANISM: Artificial Sequence
<220> FEATURE:
<221> NAME/KEY: UNSURE
<222> LOCATION: (1)
<223> OTHER INFORMATION: Unsure
<220> FEATURE:
<223> OTHER INFORMATION: Description of Artificial Sequence: Synthetic

<400> SEQUENCE: 366

Xaa Gly Cys Tyr Gln Lys Arg Cys Thr
  1               5

<210> SEQ ID NO: 367
<211> LENGTH: 9
<212> TYPE: PRT
<213> ORGANISM: Artificial Sequence
<220> FEATURE:
<221> NAME/KEY: UNSURE
<222> LOCATION: (5)
<223> OTHER INFORMATION: Unsure
<220> FEATURE:
<223> OTHER INFORMATION: Description of Artificial Sequence: Synthetic

<400> SEQUENCE: 367

Leu Gly Cys Phe Xaa Ser Trp Cys Gly
  1               5

<210> SEQ ID NO: 368
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 368

Ile Arg Cys Trp Gly Gly Arg Cys Ser
  1               5
```

<210> SEQ ID NO: 369
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 369

Ile Pro Cys Ser Leu Leu Gly Cys Ala
 1               5

<210> SEQ ID NO: 370
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 370

Ala Gly Cys Val Gln Ser Gln Cys Tyr
 1               5

<210> SEQ ID NO: 371
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 371

Pro Arg Cys Trp Glu Arg Val Cys Ser
 1               5

<210> SEQ ID NO: 372
<211> LENGTH: 9
<212> TYPE: PRT
<213> ORGANISM: Artificial Sequence
<220> FEATURE:
<221> NAME/KEY: UNSURE
<222> LOCATION: (9)
<220> FEATURE:
<223> OTHER INFORMATION: Description of Artificial Sequence: Synthetic

<400> SEQUENCE: 372

Lys Ala Cys Phe Gly Ala Asp Cys Xaa
 1               5

<210> SEQ ID NO: 373
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 373

Thr Leu Cys Pro Leu Val Ala Cys Glu
 1               5

<210> SEQ ID NO: 374
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 374

Ser Ala Cys Trp Leu Ser Asn Cys Ala

```
<210> SEQ ID NO: 375
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 375

Ser Glu Cys Tyr Thr Gly Ser Cys Pro
 1               5

<210> SEQ ID NO: 376
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 376

Gly Leu Cys Gln Glu His Arg Cys Trp
 1               5

<210> SEQ ID NO: 377
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 377

Val Glu Cys Gly Phe Ser Ala Val Phe
 1               5

<210> SEQ ID NO: 378
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 378

Glu Asp Cys Arg Glu Trp Gly Cys Arg
 1               5

<210> SEQ ID NO: 379
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 379

His Trp Cys Arg Leu Leu Ala Cys Arg
 1               5

<210> SEQ ID NO: 380
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 380

His Lys Gly Gln Val Tyr Ser
 1               5
```

```
<210> SEQ ID NO: 381
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 381

Phe Ser Asp Val His Phe Trp
  1               5

<210> SEQ ID NO: 382
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 382

Arg Gly Ile Phe Val Ser Ser
  1               5

<210> SEQ ID NO: 383
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 383

Pro Lys Val Lys Leu Ser Glu
  1               5

<210> SEQ ID NO: 384
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 384

Leu Arg Phe Trp Gln Glu Ser
  1               5

<210> SEQ ID NO: 385
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 385

Ile Trp Thr Val Val Gly Gln
  1               5

<210> SEQ ID NO: 386
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 386

Asp Lys Val Gly Leu Ser Val
  1               5
```

```
<210> SEQ ID NO: 387
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 387

Ser Glu Thr Trp Arg Gln Phe
 1               5

<210> SEQ ID NO: 388
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 388

Leu Asp Gly Met Ile Val Lys
 1               5

<210> SEQ ID NO: 389
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 389

Arg Tyr Pro Leu Ala Gly Gly
 1               5

<210> SEQ ID NO: 390
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 390

Phe Thr Asp Gly Glu Asp Lys
 1               5

<210> SEQ ID NO: 391
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 391

Arg Ser Thr Glu His Met Ser
 1               5

<210> SEQ ID NO: 392
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 392

Ser Gly Arg Arg His Glu Leu
 1               5
```

```
<210> SEQ ID NO: 393
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 393

Ser Ser Ser Arg Val Arg Ser
 1               5

<210> SEQ ID NO: 394
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 394

Tyr His Arg Ser Val Gly Arg
 1               5

<210> SEQ ID NO: 395
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 395

Pro Leu Leu Arg Pro Pro His
 1               5

<210> SEQ ID NO: 396
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 396

Ser Asp Lys Leu Gly Phe Val
 1               5

<210> SEQ ID NO: 397
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 397

Ala Gly Ser Arg Thr Asn Arg
 1               5

<210> SEQ ID NO: 398
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 398

Ile Thr Gln Leu His Lys Thr
 1               5

<210> SEQ ID NO: 399
```

```
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 399

Ala Arg Cys Leu Val Tyr Arg
 1               5

<210> SEQ ID NO: 400
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 400

Gly Tyr Val Ala Val Met Thr
 1               5

<210> SEQ ID NO: 401
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 401

Gly Leu Gln Val Lys Trp Val
 1               5

<210> SEQ ID NO: 402
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 402

Ile Phe Thr Pro Gly Trp Leu
 1               5

<210> SEQ ID NO: 403
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 403

Lys Gln Thr Ser Arg Phe Leu
 1               5

<210> SEQ ID NO: 404
<211> LENGTH: 7
<212> TYPE: PRT
<213> ORGANISM: Artificial Sequence
<220> FEATURE:
<221> NAME/KEY: SITE
<222> LOCATION: (2)
<223> OTHER INFORMATION: Tyrosine or Phenylalanine
<220> FEATURE:
<223> OTHER INFORMATION: Description of Artificial Sequence: Synthetic

<400> SEQUENCE: 404

Arg Xaa Leu Leu Ala Gly Gly
 1               5
```

```
<210> SEQ ID NO: 405
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 405

Ala Arg Arg Gly Trp Thr Leu
 1               5

<210> SEQ ID NO: 406
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 406

Ser Arg Arg Phe Val Gly Gly
 1               5

<210> SEQ ID NO: 407
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 407

Gln Leu Thr Gly Gly Cys Leu
 1               5

<210> SEQ ID NO: 408
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 408

Ala Leu Glu Arg Arg Ser Leu
 1               5

<210> SEQ ID NO: 409
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 409

Lys Ala Tyr Phe Arg Trp Arg
 1               5

<210> SEQ ID NO: 410
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 410

Arg Trp Leu Ala Trp Thr Val
 1               5
```

```
<210> SEQ ID NO: 411
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 411

Val Gly Ser Phe Ile Tyr Ser
 1               5

<210> SEQ ID NO: 412
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 412

Leu Ser Leu Leu Gly Ile Ala
 1               5

<210> SEQ ID NO: 413
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 413

Leu Ser Thr Val Leu Trp Phe
 1               5

<210> SEQ ID NO: 414
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 414

Ser Leu Ala Met Arg Asp Ser
 1               5

<210> SEQ ID NO: 415
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 415

Gly Arg Ser Ser Leu Ala Cys
 1               5

<210> SEQ ID NO: 416
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 416

Ser Glu Leu Leu Gly Asp Ala
 1               5
```

```
<210> SEQ ID NO: 417
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 417

Cys Gly Gly Ala Gly Ala Arg
 1               5

<210> SEQ ID NO: 418
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 418

Trp Arg Gln Asn Met Pro Leu
 1               5

<210> SEQ ID NO: 419
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 419

Asp Phe Leu Arg Cys Arg Val
 1               5

<210> SEQ ID NO: 420
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 420

Gln Ala Gly Leu Arg Cys His
 1               5

<210> SEQ ID NO: 421
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 421

Arg Ala Leu Tyr Asp Ala Leu
 1               5

<210> SEQ ID NO: 422
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 422

Trp Val Ser Val Leu Gly Phe
 1               5

<210> SEQ ID NO: 423
```

```
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 423

Gly Met Ala Val Ser Ser Trp
 1               5

<210> SEQ ID NO: 424
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 424

Ser Trp Phe Phe Leu Val Ala
 1               5

<210> SEQ ID NO: 425
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 425

Trp Gln Ser Val Val Arg Val
 1               5

<210> SEQ ID NO: 426
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 426

Cys Gly Asn Gly His Ser Cys
 1               5

<210> SEQ ID NO: 427
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 427

Ala Glu Met Glu Gly Arg Asp
 1               5

<210> SEQ ID NO: 428
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 428

Ser Leu Arg Pro Asp Asn Gly
 1               5

<210> SEQ ID NO: 429
<211> LENGTH: 7
```

```
<212> TYPE: PRT
<213> ORGANISM: Artificial Sequence
<220> FEATURE:
<223> OTHER INFORMATION: Description of Artificial Sequence: Synthetic

<400> SEQUENCE: 429

Pro Ala Met Gly Leu Ile Arg
  1               5

<210> SEQ ID NO: 430
<211> LENGTH: 4
<212> TYPE: PRT
<213> ORGANISM: Artificial Sequence
<220> FEATURE:
<223> OTHER INFORMATION: Description of Artificial Sequence: Synthetic

<400> SEQUENCE: 430

Leu Ala Gly Gly
  1

<210> SEQ ID NO: 431
<211> LENGTH: 23
<212> TYPE: PRT
<213> ORGANISM: Artificial Sequence
<220> FEATURE:
<221> NAME/KEY: SITE
<222> LOCATION: (1)
<223> OTHER INFORMATION: 1 to 10 independently selected amino acids
<220> FEATURE:
<221> NAME/KEY: SITE
<222> LOCATION: (14)..(23)
<223> OTHER INFORMATION: 1 to 10 independently selected amino acids
<220> FEATURE:
<223> OTHER INFORMATION: Description of Artificial Sequence: Synthetic

<400> SEQUENCE: 431

Xaa Xaa Xaa Xaa Xaa Xaa Xaa Xaa Xaa Xaa Leu Pro Arg Xaa Xaa Xaa
  1               5                  10                  15

Xaa Xaa Xaa Xaa Xaa Xaa Xaa
             20

<210> SEQ ID NO: 432
<211> LENGTH: 24
<212> TYPE: PRT
<213> ORGANISM: Artificial Sequence
<220> FEATURE:
<221> NAME/KEY: SITE
<222> LOCATION: (1)..(10)
<223> OTHER INFORMATION: 1 to 10 independently selected amino acids
<220> FEATURE:
<221> NAME/KEY: SITE
<222> LOCATION: (15)..(25)
<223> OTHER INFORMATION: 0 to 10 independently selected amino acids
<220> FEATURE:
<223> OTHER INFORMATION: Description of Artificial Sequence: Synthetic

<400> SEQUENCE: 432

Xaa Xaa Xaa Xaa Xaa Xaa Xaa Xaa Xaa Xaa Leu Ala Gly Gly Xaa Xaa
  1               5                  10                  15

Xaa Xaa Xaa Xaa Xaa Xaa Xaa Xaa
             20

<210> SEQ ID NO: 433
<211> LENGTH: 15
<212> TYPE: PRT
<213> ORGANISM: Artificial Sequence
<220> FEATURE:
<221> NAME/KEY: SITE
<222> LOCATION: (6)..(15)
```

```
<223> OTHER INFORMATION: 1 to 10 independently selected amino acids
<220> FEATURE:
<223> OTHER INFORMATION: Description of Artificial Sequence: Synthetic

<400> SEQUENCE: 433

Tyr Ser Gly Lys Trp Xaa Xaa Xaa Xaa Xaa Xaa Xaa Xaa Xaa Xaa
  1               5                   10                  15

<210> SEQ ID NO: 434
<211> LENGTH: 23
<212> TYPE: PRT
<213> ORGANISM: Artificial Sequence
<220> FEATURE:
<221> NAME/KEY: SITE
<222> LOCATION: (1)..(10)
<223> OTHER INFORMATION: 1 to 10 independently selected amino acids
<220> FEATURE:
<221> NAME/KEY: SITE
<222> LOCATION: (14)..(23)
<223> OTHER INFORMATION: 1 to 10 independently selected amino acids
<220> FEATURE:
<223> OTHER INFORMATION: Description of Artificial Sequence: Synthetic

<400> SEQUENCE: 434

Xaa Xaa Xaa Xaa Xaa Xaa Xaa Xaa Xaa Xaa Arg Gly Ser Xaa Xaa Xaa
  1               5                   10                  15

Xaa Xaa Xaa Xaa Xaa Xaa Xaa
                20

<210> SEQ ID NO: 435
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 435

Cys Cys Phe Thr Asn Phe Asp Cys Tyr Leu Gly Cys
  1               5                   10

<210> SEQ ID NO: 436
<211> LENGTH: 23
<212> TYPE: PRT
<213> ORGANISM: Artificial Sequence
<220> FEATURE:
<221> NAME/KEY: UNSURE
<222> LOCATION: (1)..(10)
<223> OTHER INFORMATION: 1 to 10 independently selected amino acids
<220> FEATURE:
<221> NAME/KEY: UNSURE
<222> LOCATION: (14)..(23)
<223> OTHER INFORMATION: 1 to 10 independently selected amino acids
<220> FEATURE:
<223> OTHER INFORMATION: Description of Artificial Sequence: Synthetic

<400> SEQUENCE: 436

Xaa Xaa Xaa Xaa Xaa Xaa Xaa Xaa Xaa Xaa Arg Asp Val Xaa Xaa Xaa
  1               5                   10                  15

Xaa Xaa Xaa Xaa Xaa Xaa Xaa
                20
```